US009873710B2

(12) United States Patent
Smaill et al.

(10) Patent No.: US 9,873,710 B2
(45) Date of Patent: *Jan. 23, 2018

(54) PRODRUGS AND METHODS OF USE THEREOF

(71) Applicant: Health Innovation Ventures B.V., Maastricht (NL)

(72) Inventors: Jeffrey Bruce Smaill, Auckland (NZ); Adam Vorn Patterson, Waiheke Island (NZ); Amir Ashoorzadeh, Auckland (NZ); Christopher Paul Guise, Auckland (NZ); Alexandra Marie Mowday, Auckland (NZ); David Francis Ackerley, Wellington (NZ); Elsie May Williams, Wellington (NZ); Janine Naomi Copp, Nelson (NZ)

(73) Assignee: Health Innovation Ventures B.V., Maastricht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/339,041

(22) Filed: Oct. 31, 2016

(65) Prior Publication Data

US 2017/0044191 A1 Feb. 16, 2017

Related U.S. Application Data

(63) Continuation of application No. 14/423,359, filed as application No. PCT/NZ2013/000150 on Aug. 22, 2013, now Pat. No. 9,505,791.

(30) Foreign Application Priority Data

Aug. 23, 2012 (NZ) ........................................ 602004

(51) Int. Cl.
| | |
|---|---|
| *C07F 9/09* | (2006.01) |
| *C07C 255/58* | (2006.01) |
| *C07C 309/66* | (2006.01) |
| *C07C 317/48* | (2006.01) |
| *C07D 295/13* | (2006.01) |
| *C07D 295/192* | (2006.01) |
| *C07C 309/69* | (2006.01) |
| *C07C 317/36* | (2006.01) |
| *C07D 295/104* | (2006.01) |

(52) U.S. Cl.
CPC .............. *C07F 9/09* (2013.01); *C07C 255/58* (2013.01); *C07C 309/66* (2013.01); *C07C 309/69* (2013.01); *C07C 317/36* (2013.01); *C07C 317/48* (2013.01); *C07D 295/104* (2013.01); *C07D 295/13* (2013.01); *C07D 295/192* (2013.01); *C07F 9/091* (2013.01)

(58) Field of Classification Search
CPC ...................................................... C07F 9/09
USPC .............................. 544/106, 107; 514/237.8
See application file for complete search history.

(56) References Cited

U.S. PATENT DOCUMENTS

| | | |
|---|---|---|
| 6,310,237 B1 | 10/2001 | Feng et al. |
| 9,505,791 B2 | 11/2016 | Smaill et al. |

FOREIGN PATENT DOCUMENTS

| | | |
|---|---|---|
| WO | 88/007378 A1 | 10/1988 |
| WO | 1993/011099 A1 | 6/1993 |
| WO | 2004/033415 A1 | 4/2004 |
| WO | 2005/042471 A1 | 5/2005 |
| WO | 2008/030112 A1 | 3/2008 |
| WO | 2010/044685 A1 | 4/2010 |
| WO | 2012/008860 A2 | 1/2012 |

OTHER PUBLICATIONS

International Search Report, International Patent Application No. PCT/NZ2013/000150, dated Nov. 6, 2013, 5 pages.
International Preliminary Report on Patentability, International Patent Application No. PCT/NZ2013/000150, dated Feb. 24, 2015, 7 pages.
European Extended Search Report, European Patent Application No. 13831349.9, dated May 25, 2016, 10 pages.
Anlezark, G.M., et al., "Bioactivation of Dinitrobenzamide Mustards by an *E. coli* B Nitroreductase." Biochemical Pharmacology, 1995, vol. 50, issue No. 5, pp. 609-618.

*Primary Examiner* — Taofiq A Solola
(74) *Attorney, Agent, or Firm* — Fitch Even Tabin & Flannery LLP

(57) ABSTRACT

The invention relates to compounds of use as targeted cytotoxic agents and methods of use thereof. In particular, the invention relates to prodrugs that are substantially resistant to human AKR1C3 enzyme metabolism, methods of cell ablation using said compounds and methods of treatment of cancer and other hyperproliferative disorders using said compounds.

23 Claims, 34 Drawing Sheets

Figure 3.1
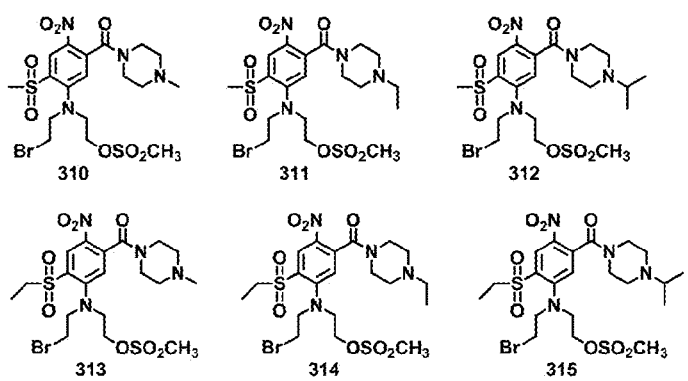
Figure 4
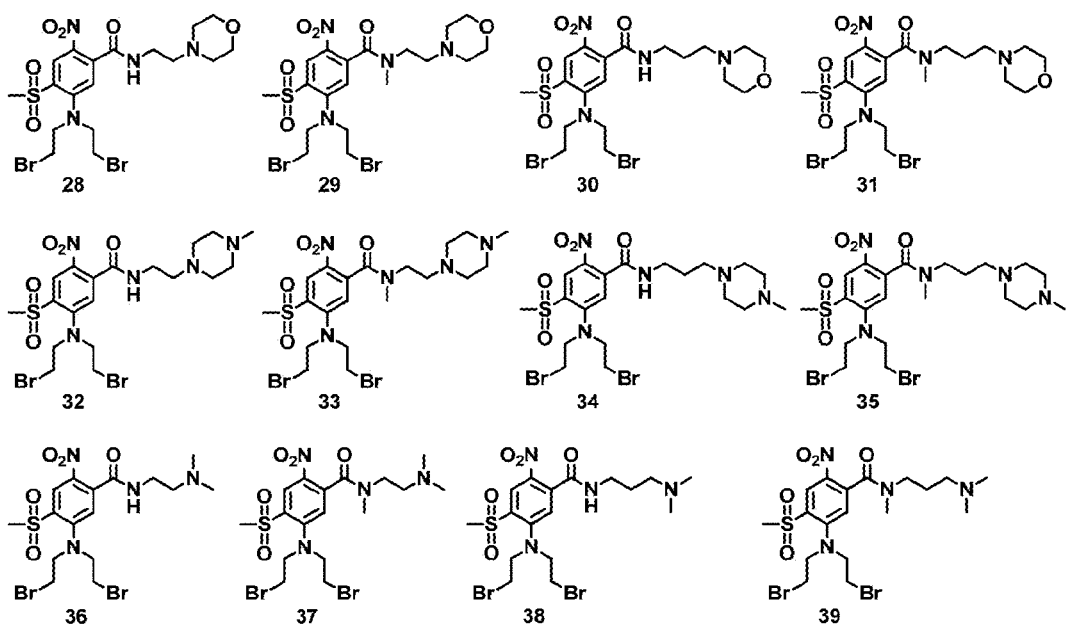

Figure 5
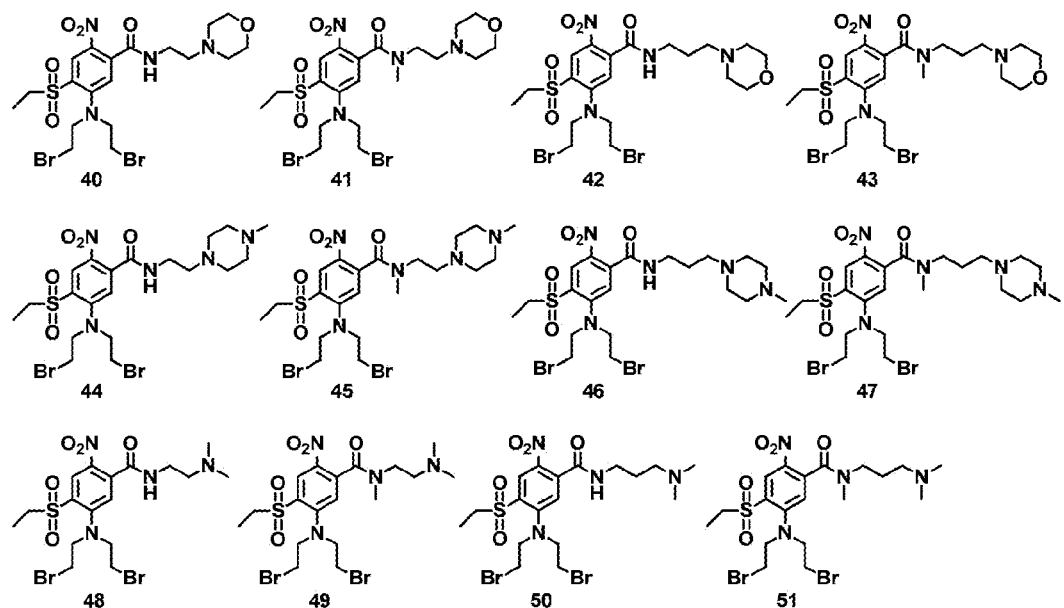
Figure 5.1
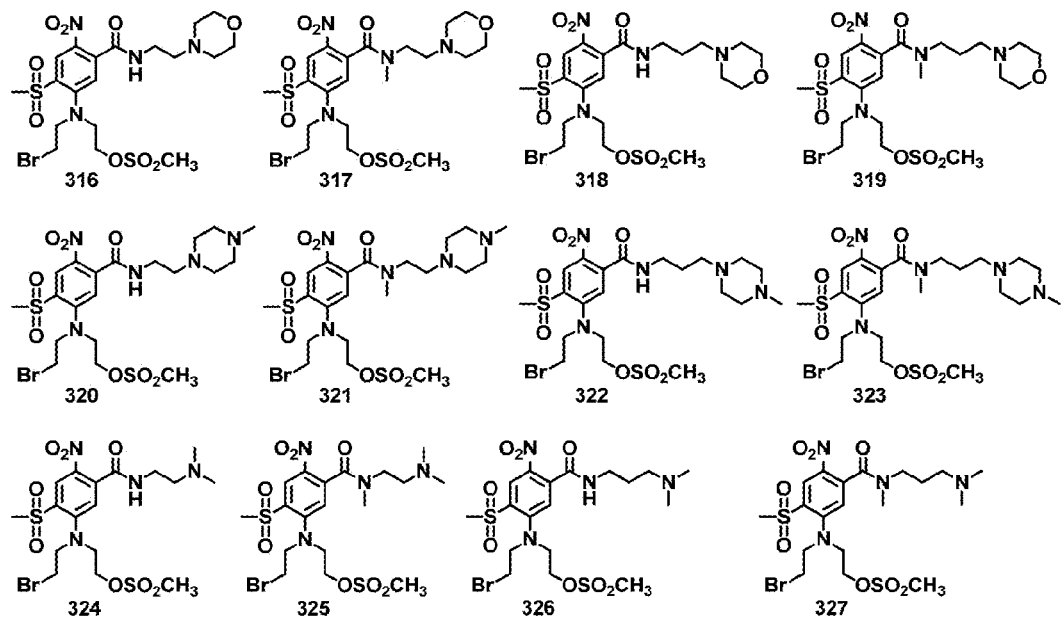

Figure 5.2
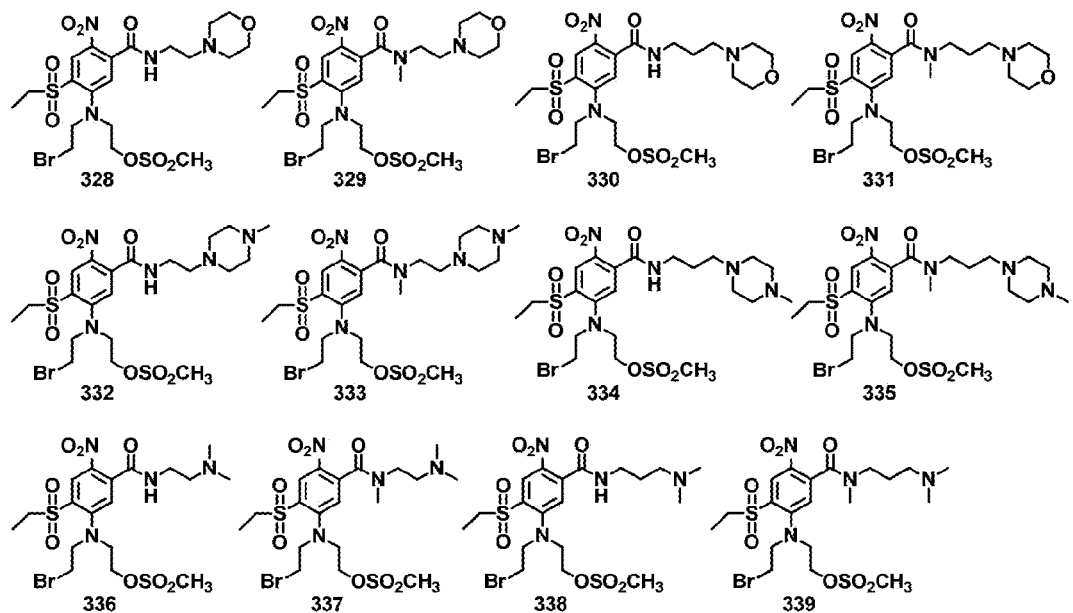
Figure 6
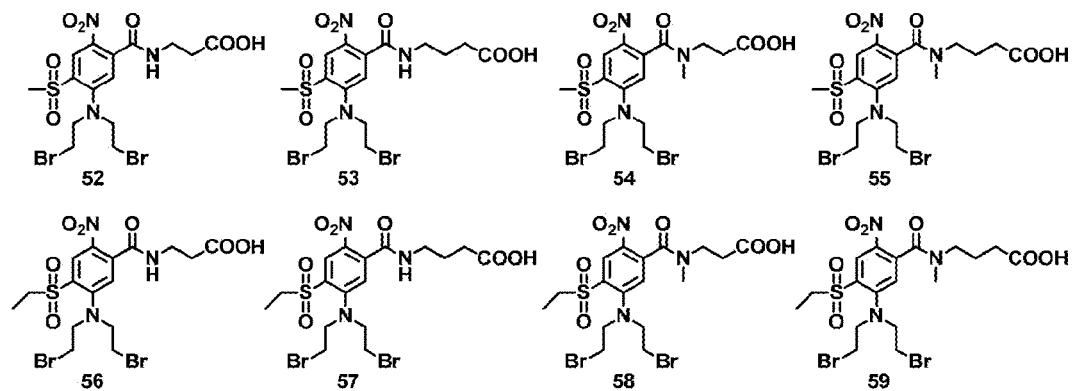

Figure 6.1
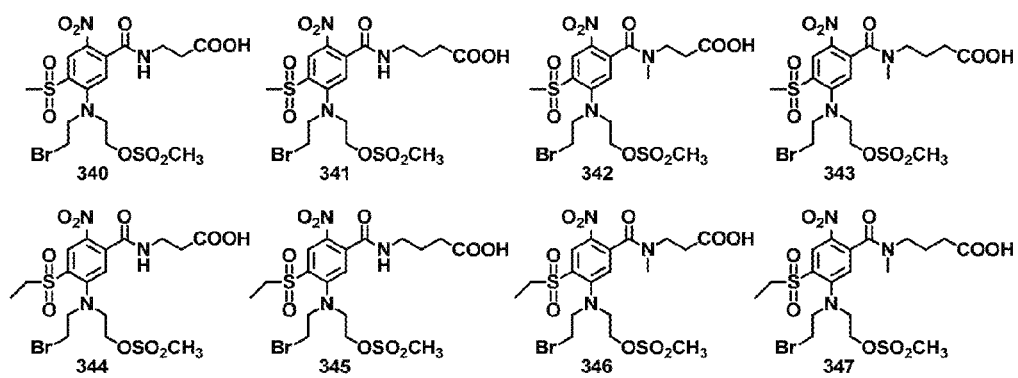

Figure 7
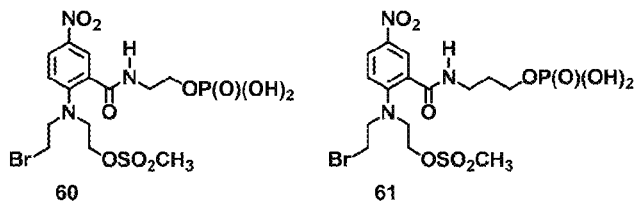
Figure 7.1
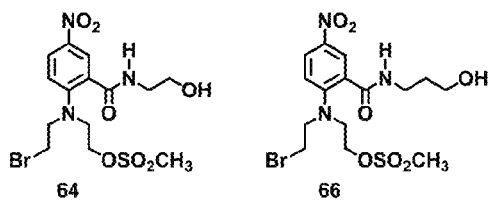
Figure 7.2
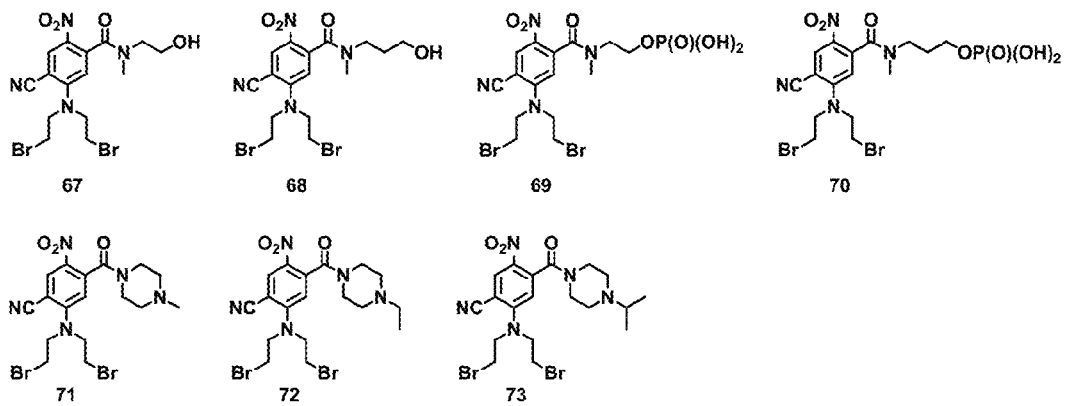

Figure 7.2.1
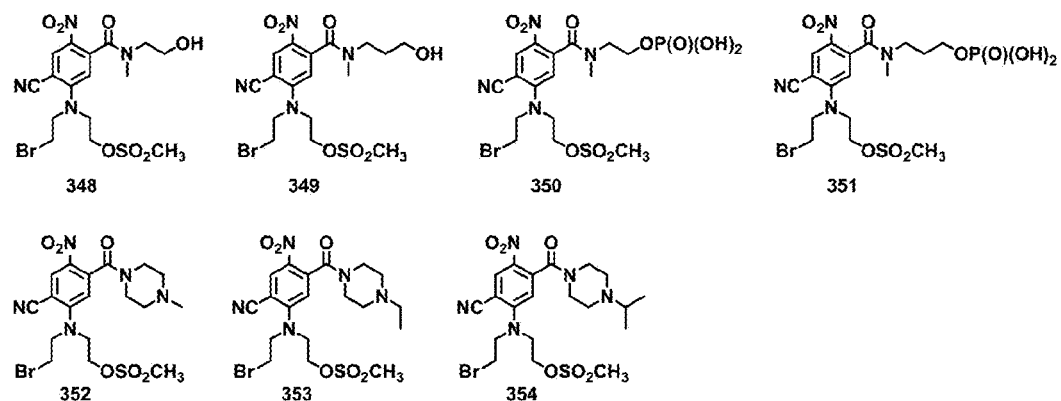
Figure 7.3
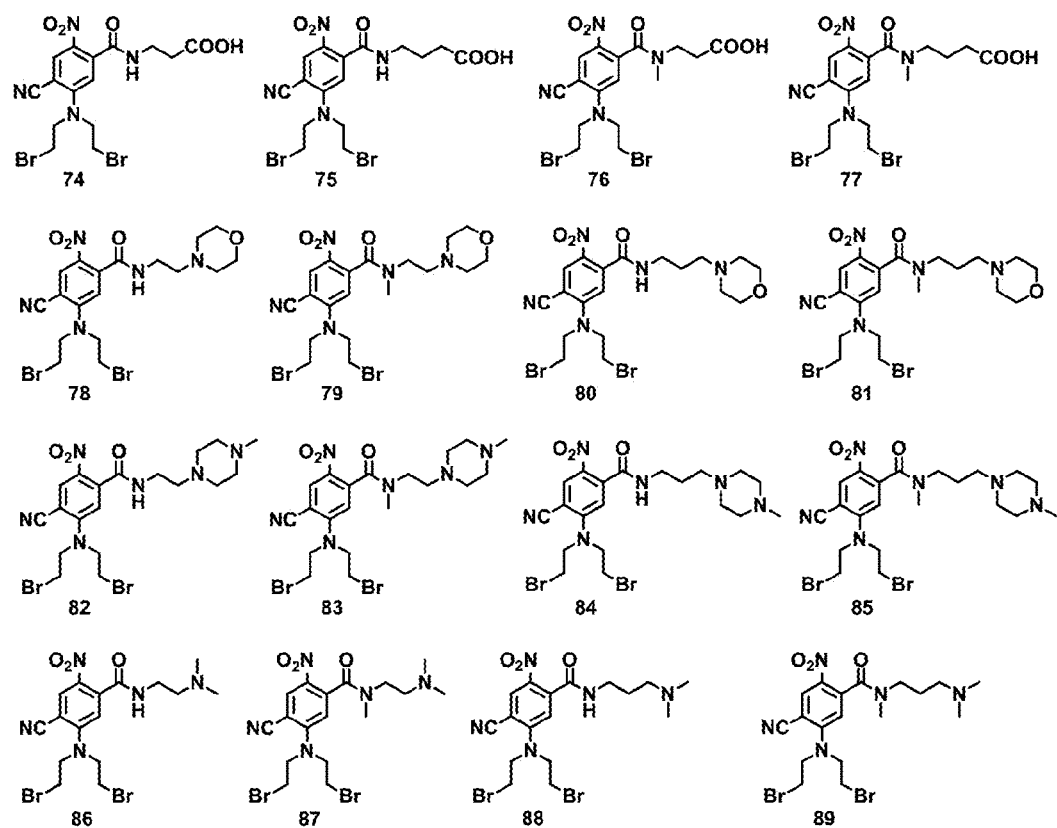

Figure 7.4
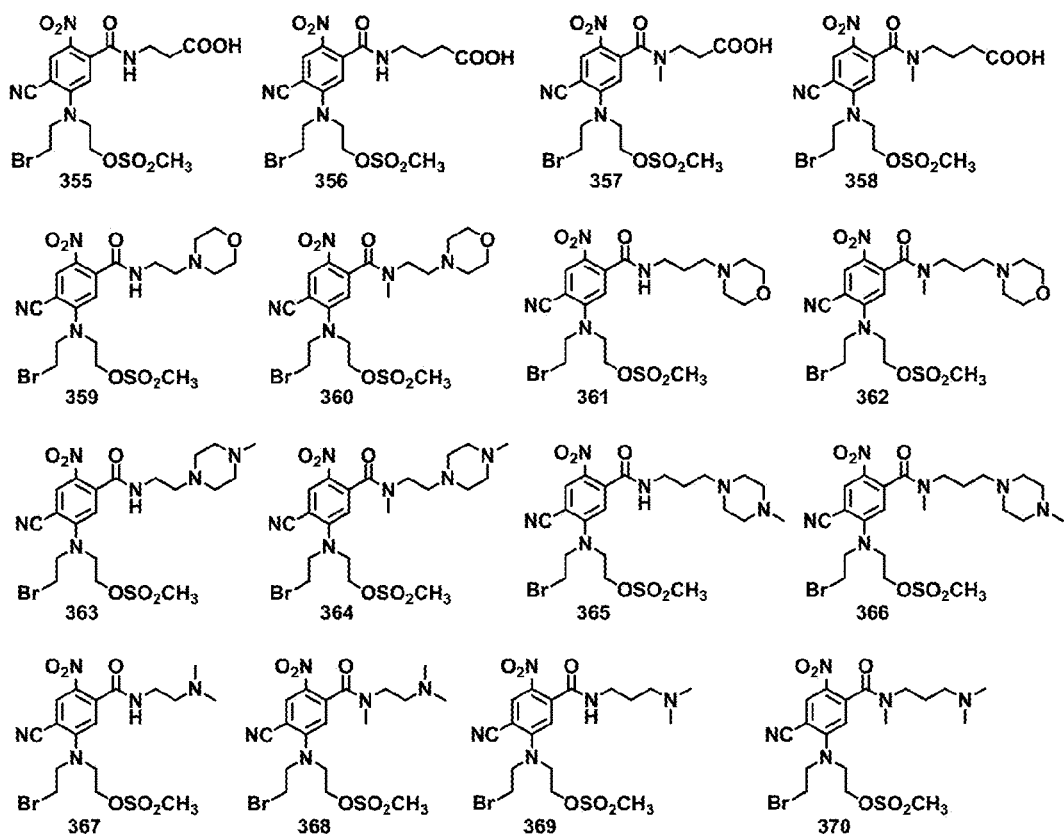

Figure 9.1
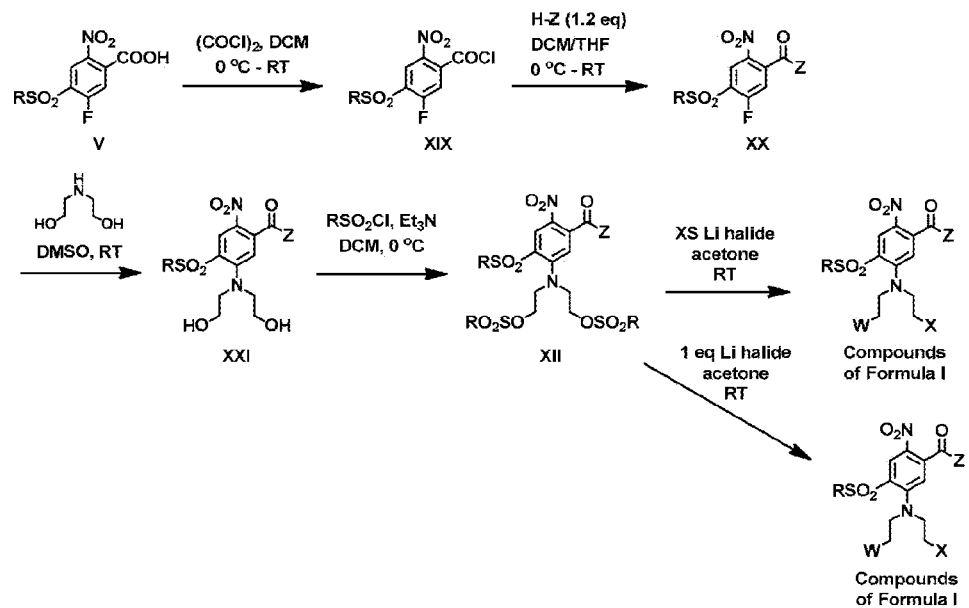
Figure 9.1.1
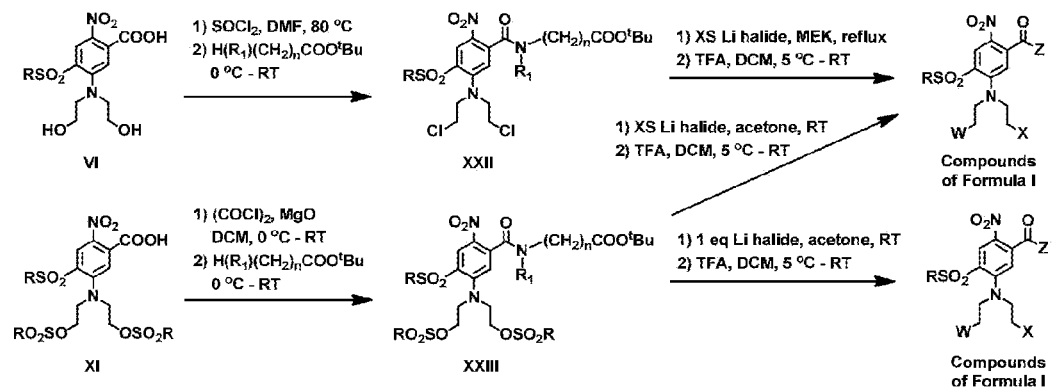

Figure 9.1.2
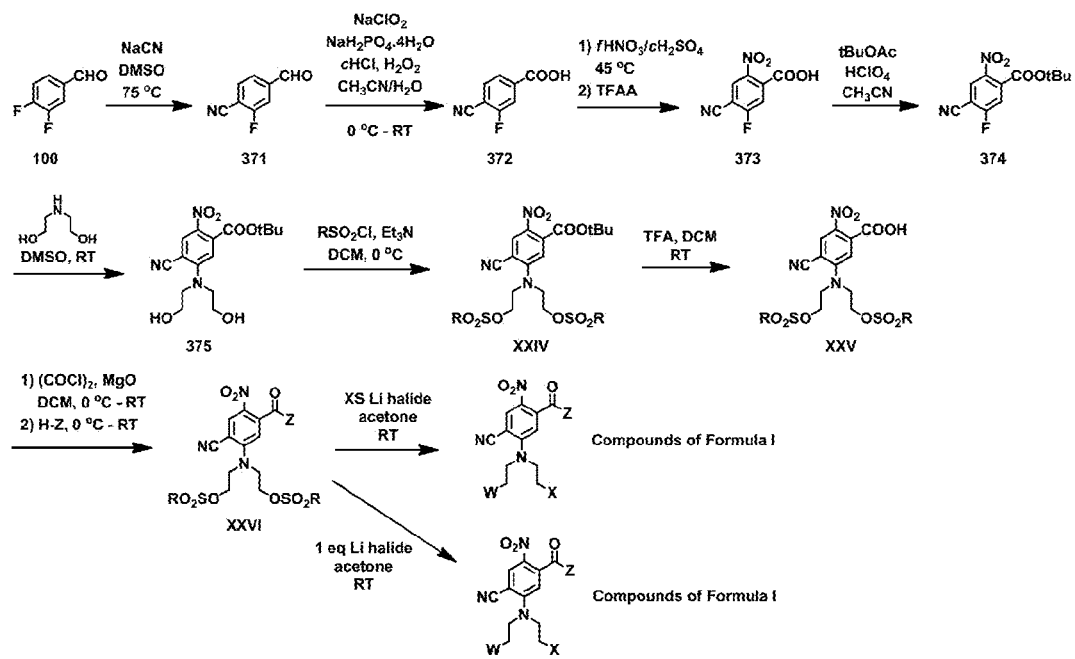
Figure 9.1.3
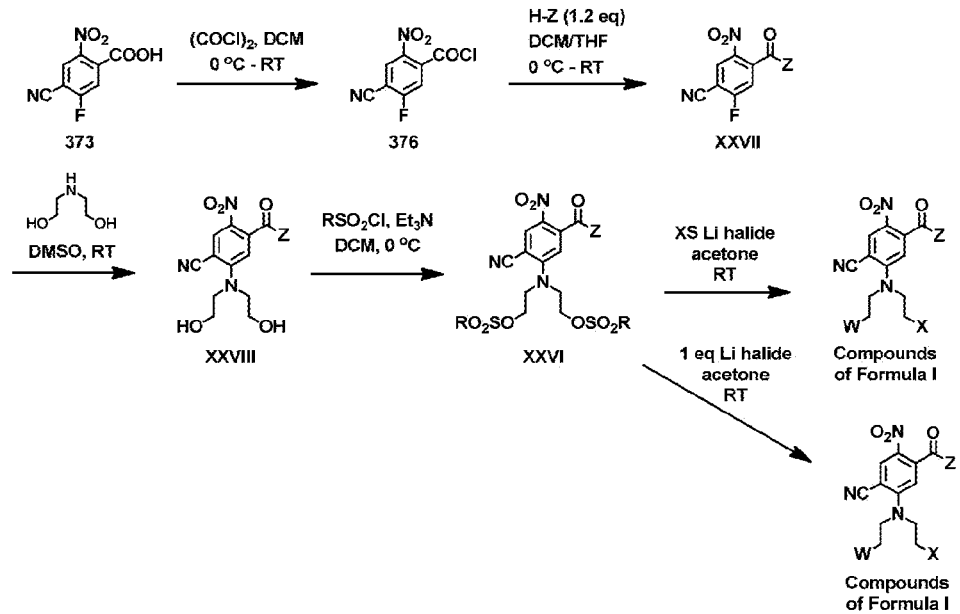

Figure 9.1.4
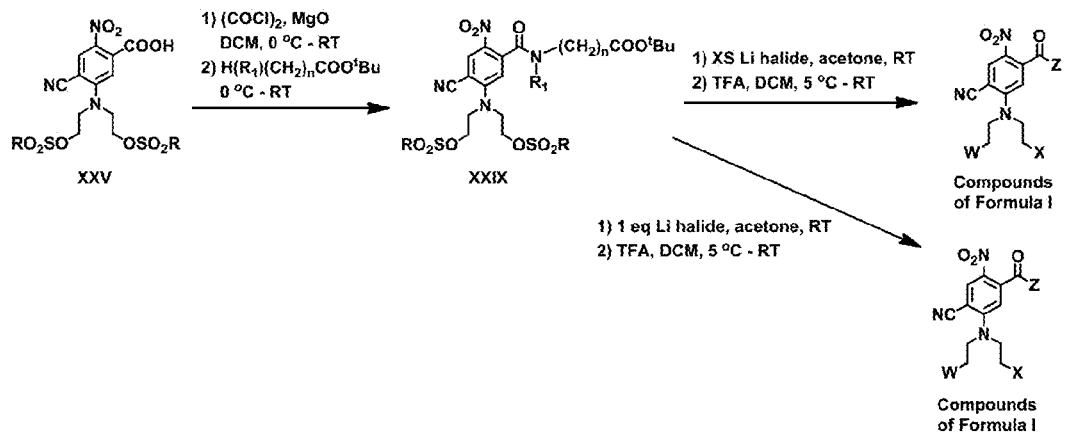
Figure 9.2
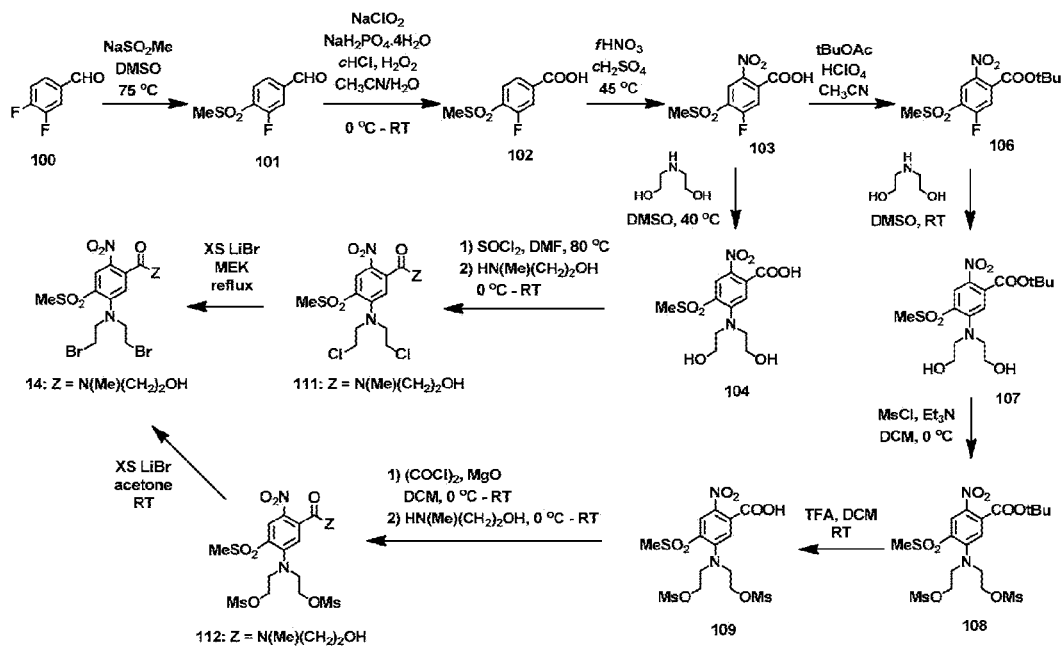

Figure 9.3
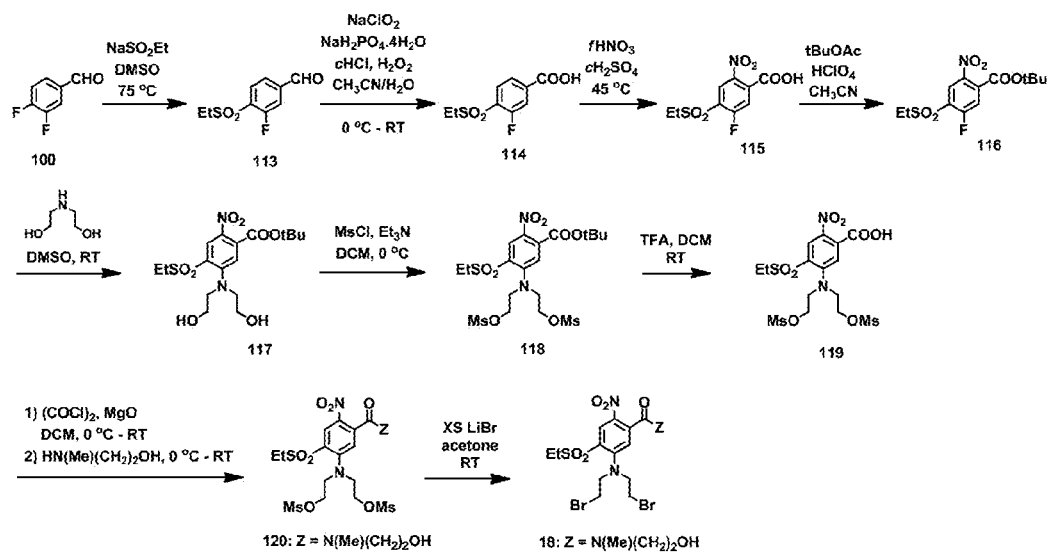
Figure 9.4
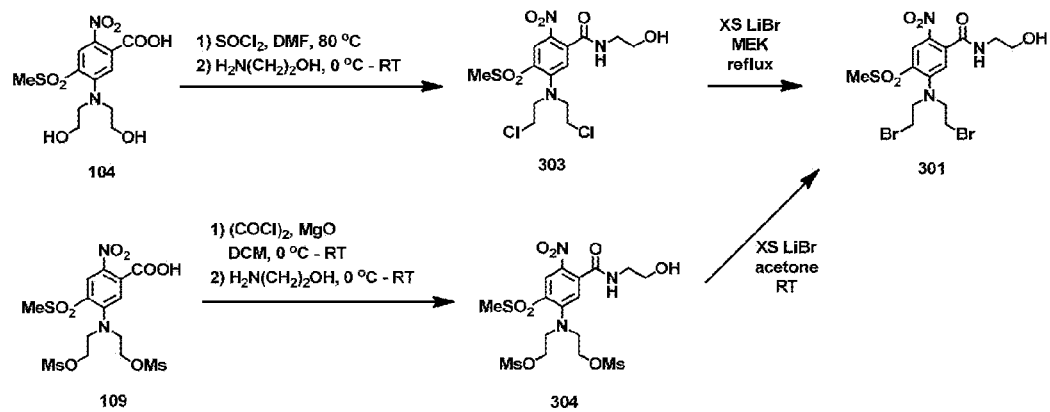

| Compound | Solubility (mM) |
|----------|-----------------|
| 4        | 0.068 [a]       |
| 10       | >95 [b]         |
| 11       | >95 [b]         |
| 23       | 36 [c]          |
| 300      | >95 [b]         |

Figure 17
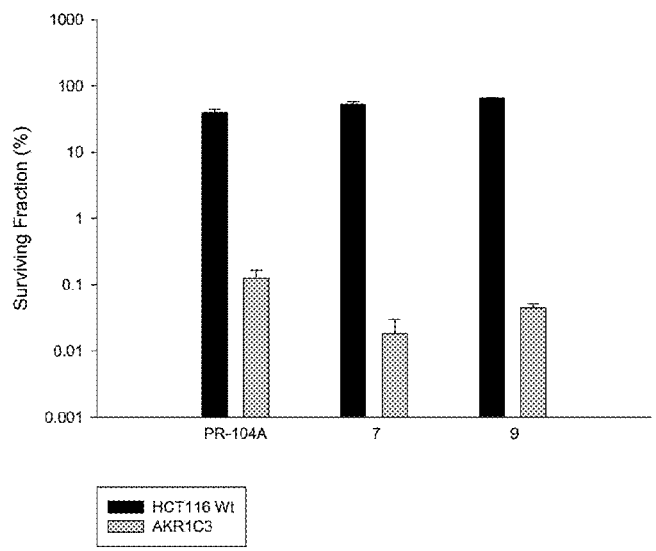
Figure 17.1
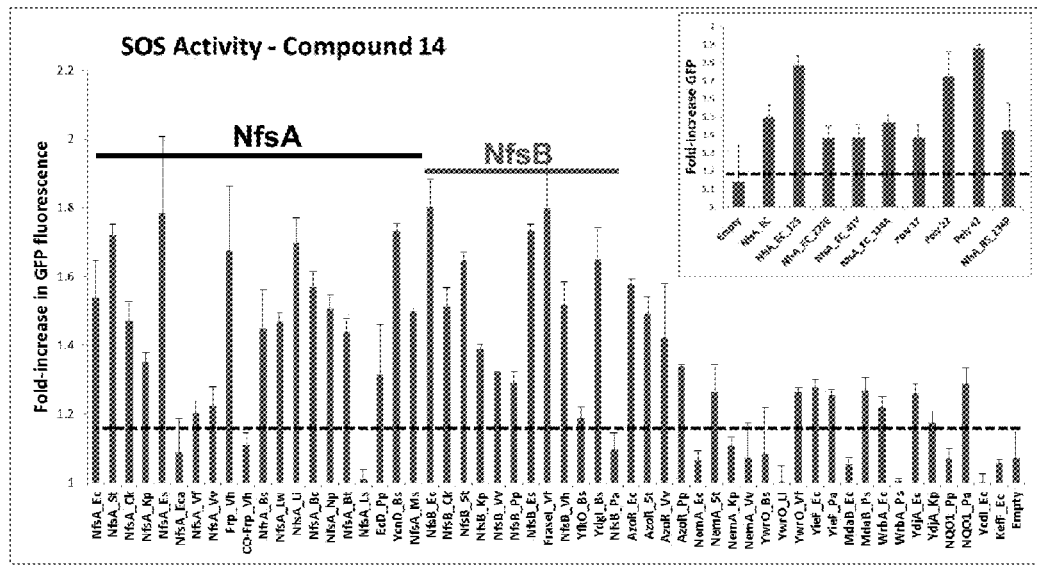

Figure 17.2
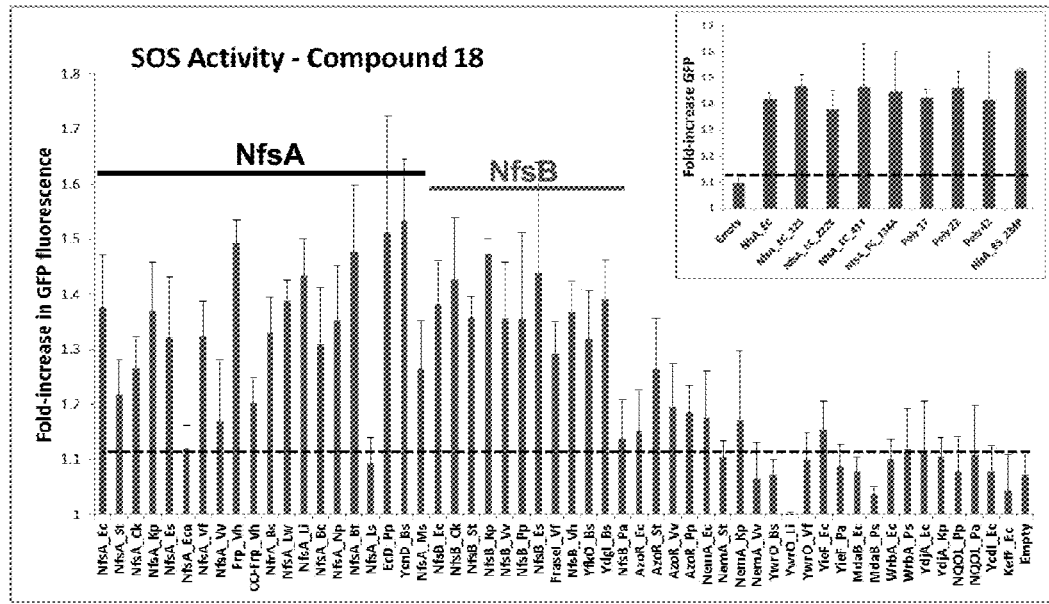
Figure 17.3
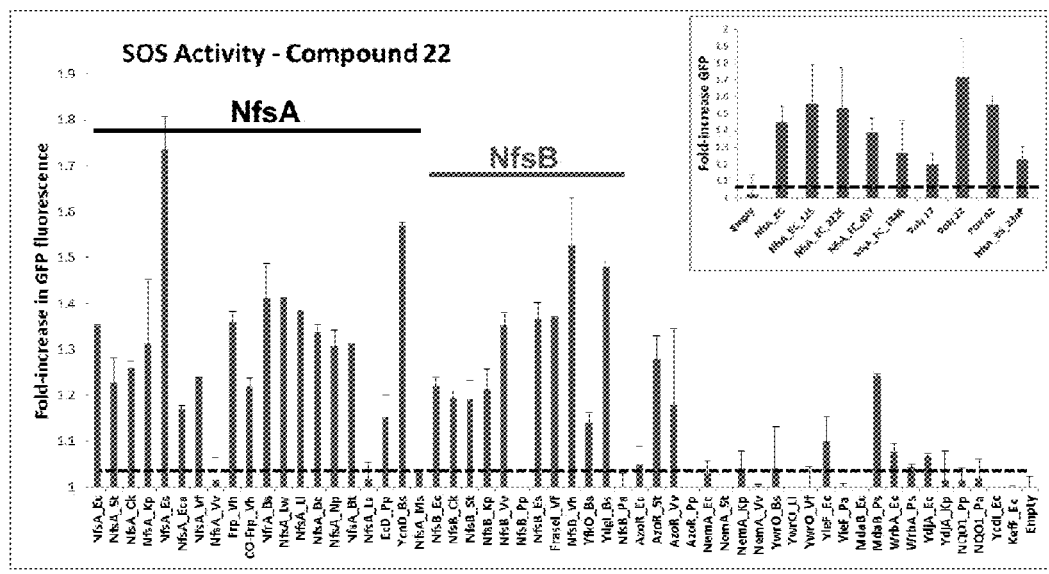

Figure 17.4
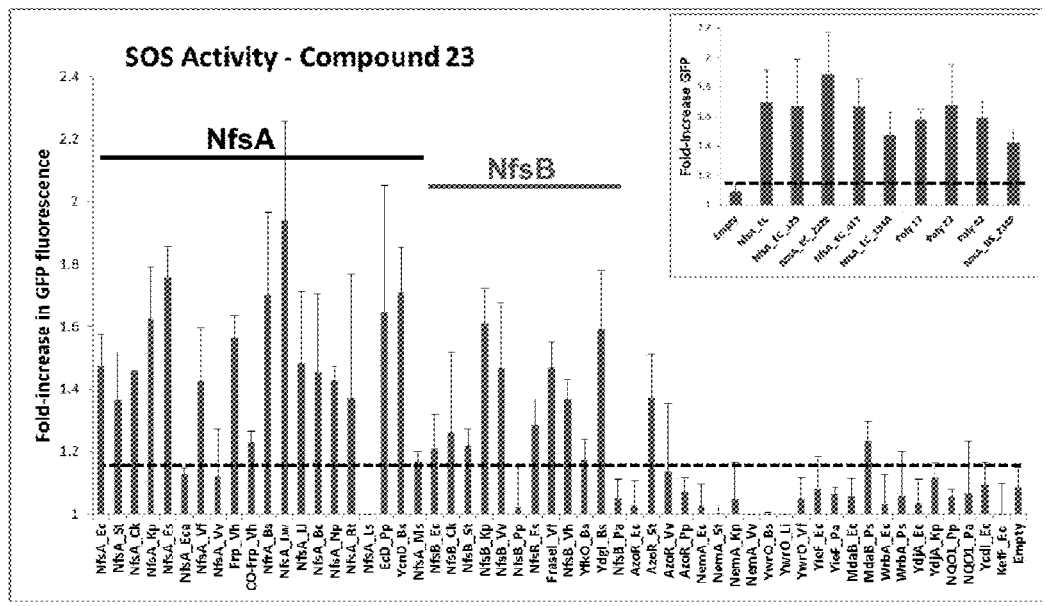
Figure 17.5
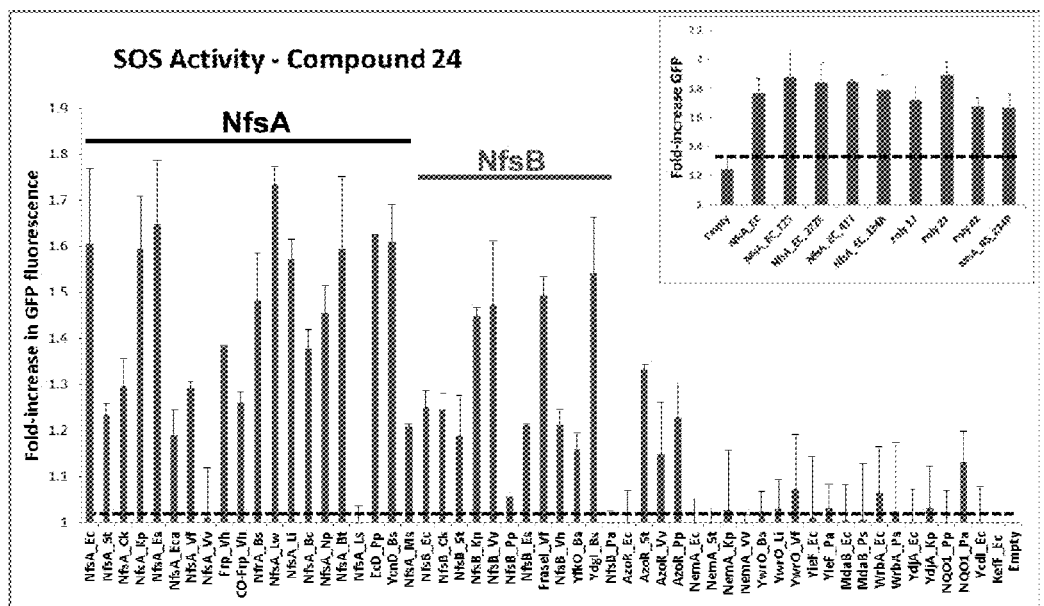

Figure 17.6
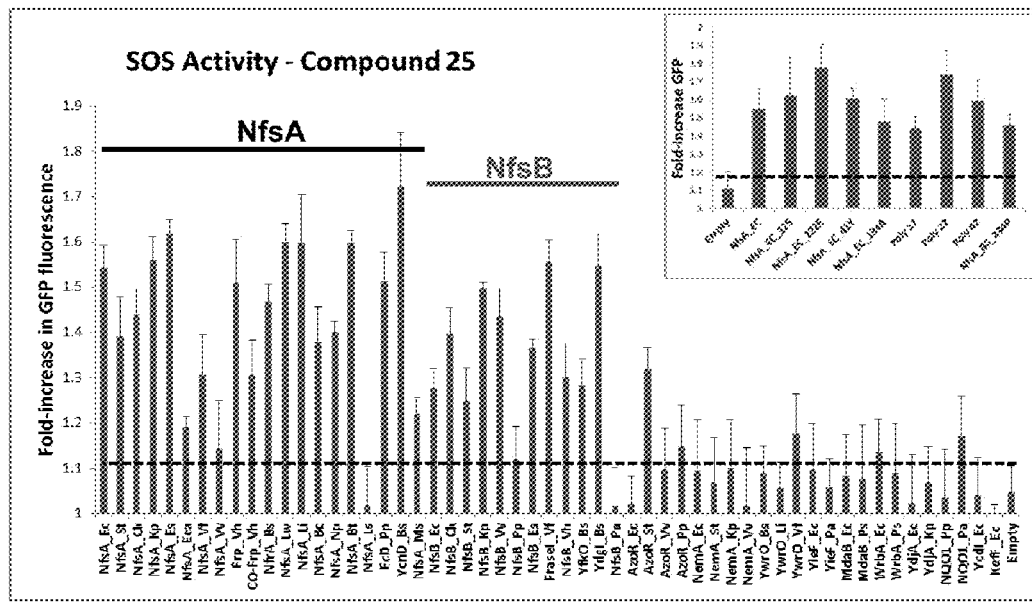
Figure 17.7
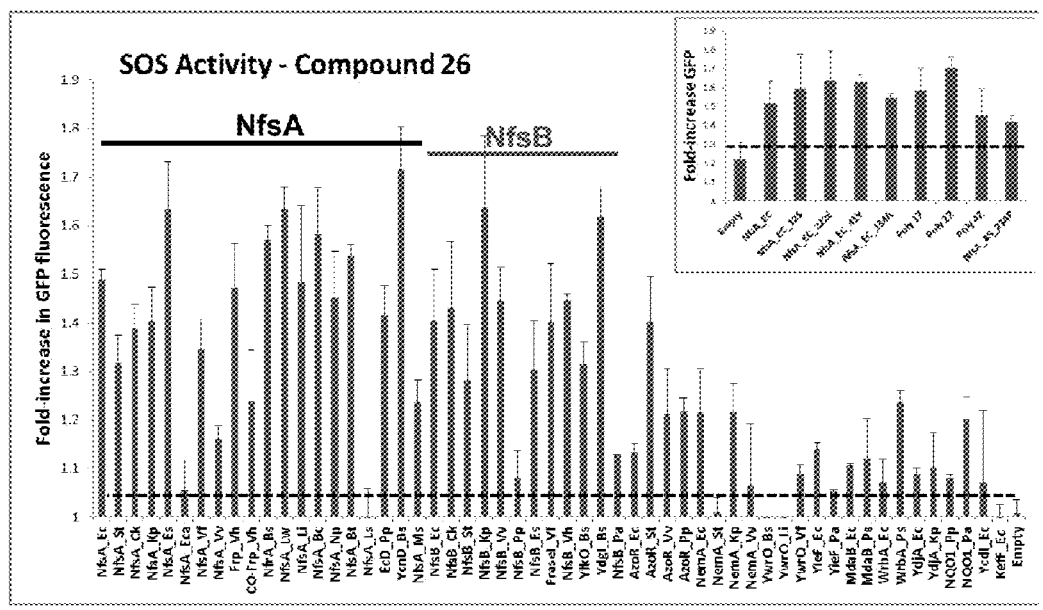

Figure 17.8
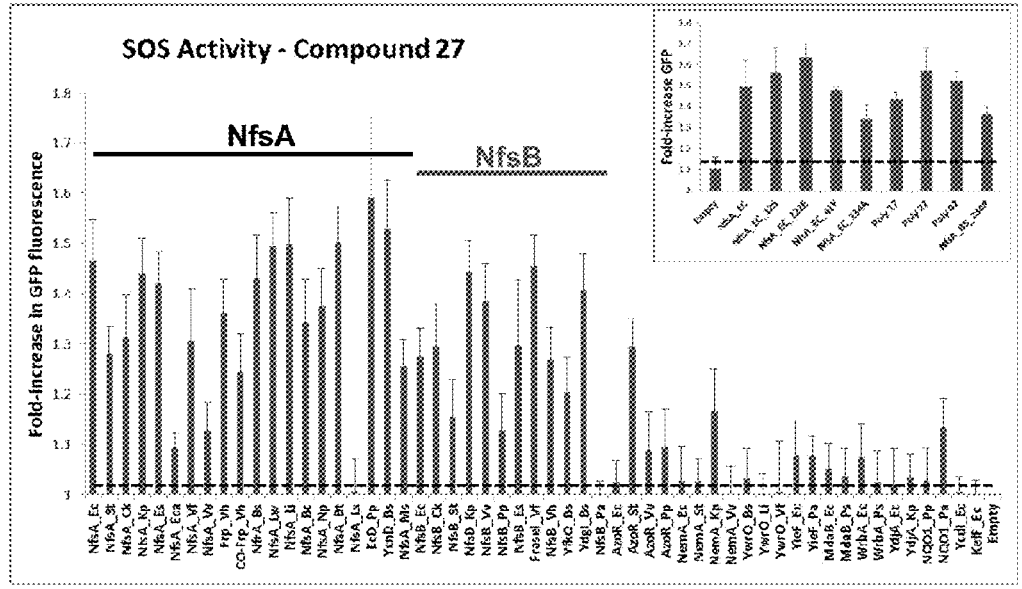
Figure 17.9
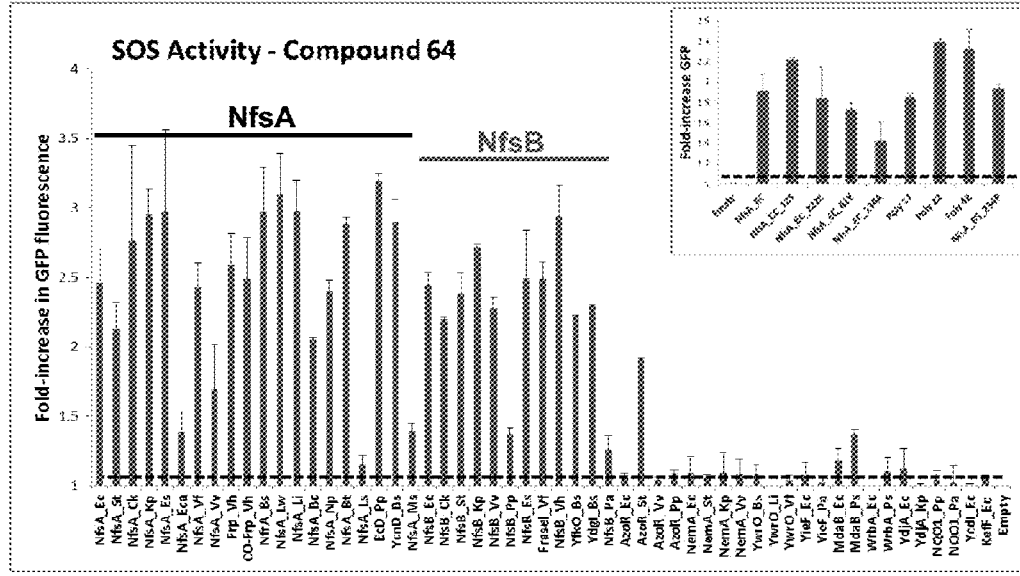

Figure 17.10
| Compound | $K_m$ (μM) | $k_{cat}$ (s$^{-1}$) | $k_{cat}/K_m$ (mM$^{-1}$ s$^{-1}$) |
|---|---|---|---|
| 14 | 160 ± 36 | 5.1 ± 0.3 | 33 |
| 18 | 210 ± 38 | 5.5 ± 0.3 | 27 |
| 22 | 400 ± 46 | 3.8 ± 0.2 | 9 |
| 23 | 280 ± 40 | 3.8 ± 0.2 | 14 |
| 24 | 590 ± 83 | 4.4 ± 0.3 | 7 |
| 25 | 240 ± 22 | 3.6 ± 0.1 | 15 |
| 26 | 380 ± 72 | 4.3 ± 0.4 | 11 |
| 27 | 820 ± 115 | 5.8 ± 0.5 | 7 |
| 64 | 810 ± 135 | 21.9 ± 2.7 | 27 |
Figure 17.11
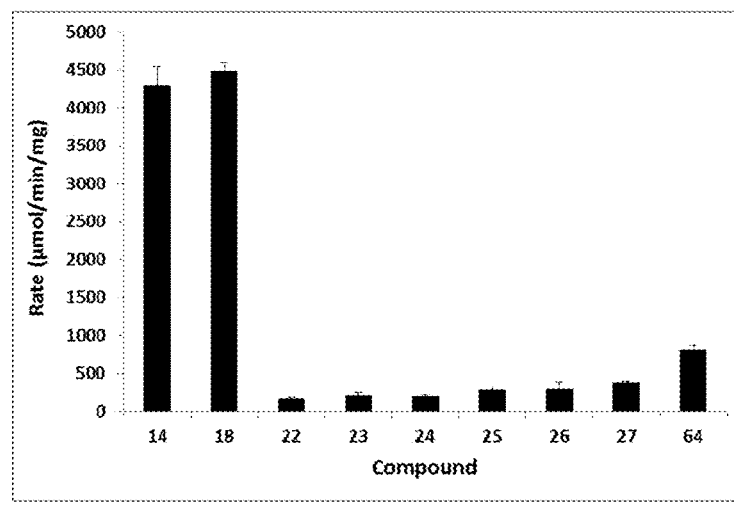

Figure 18
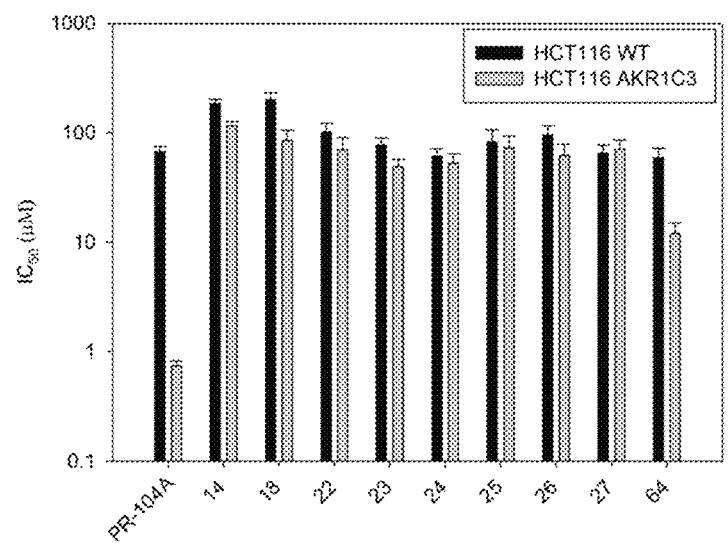
Figure 18.1
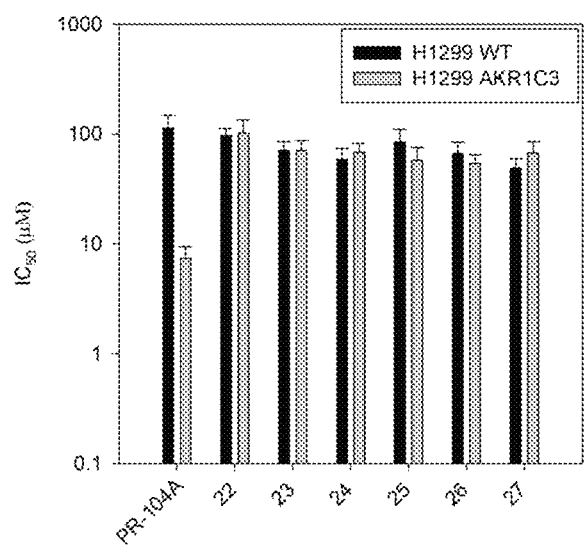

Figure 19.1

| Definitions of Formula 1f | | | | clogP [a] | AKR1C3-Negative [b] |
|---|---|---|---|---|---|
| W / X | R | R₁ | n | | |
| Br / Br | Me | H | 2 | 0.90 | Yes |
| Br / Br | Me | Me | 2 | 1.46 | Yes |
| Br / Br | Et | Me | 2 | 1.99 | Yes |
| Br / Br | Pr | Me | 2 | 2.55 | No |
| Br / Br | Me | Pr | 2 | 2.55 | No |
| Br / Br | Me | i-Pr | 2 | 2.55 | No |
| Br / Br | Et | Et | 2 | 2.55 | No |

Figure 20
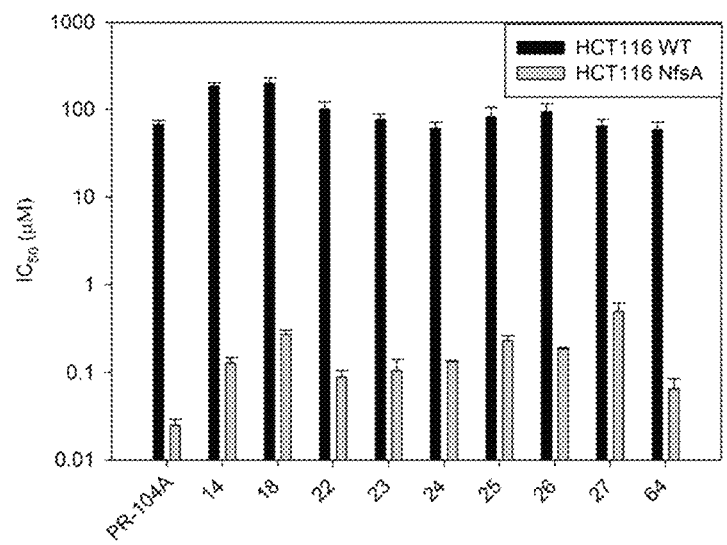
Figure 20.1
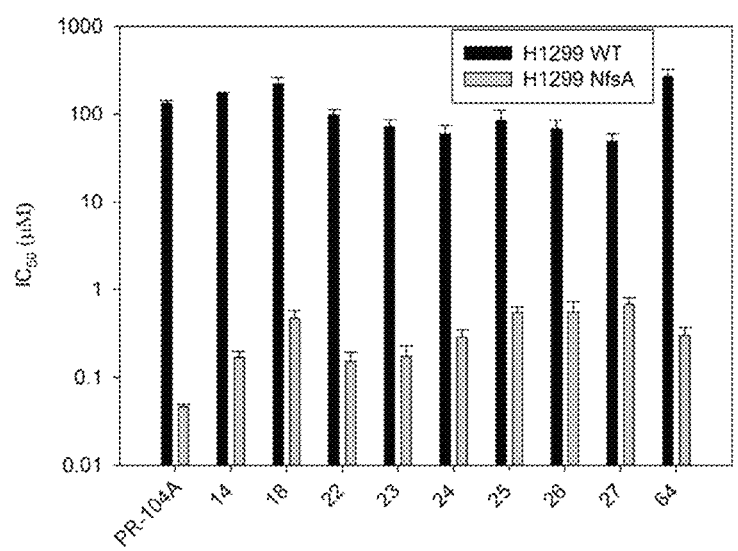

Figure 22.1
| Treatment | Dose (µmol/kg) | Median time to RTV4 (Days) | TGD (%) |
|---|---|---|---|
| Control | - | 12 | - |
| PR-104 | 388 | 20 | 67 |
| 60 | 1330 | 34 | 183 |
| 10 | 1000 | 32 | 167 |
| 22 | 422 | 30 | 150 |
Figure 22.2
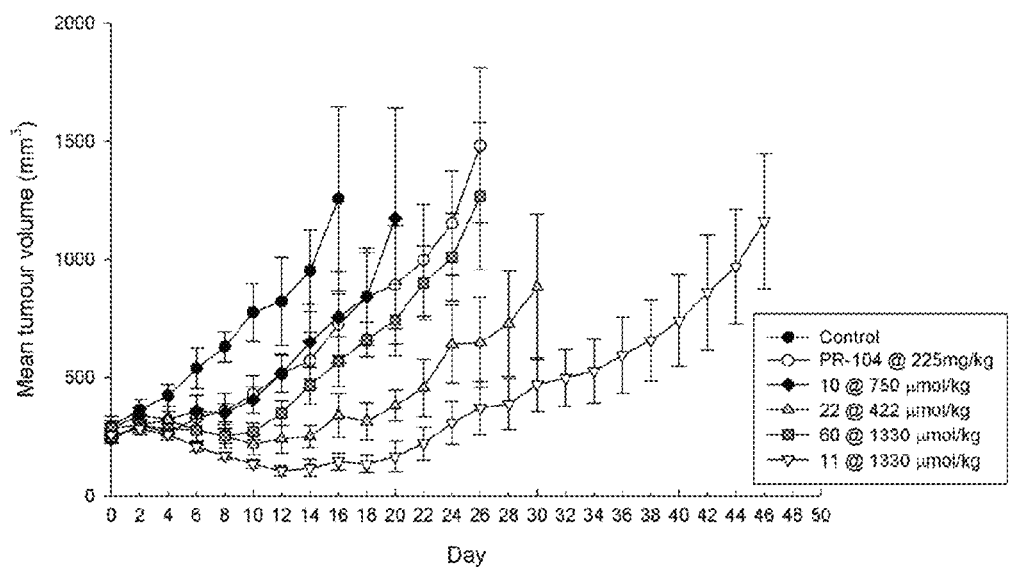

Figure 22.3
| Treatment | Dose (µmol/kg) | Median time to RTV4 (Days) | TGD (%) |
|---|---|---|---|
| Control | - | 18 | - |
| PR-104 | 388 | 24 | 33 |
| 10 | 750 | 28 | 56 |
| 22 | 422 | 44 | 144 |
| 60 | 1330 | 32 | 78 |
| 11 | 1330 | 46 | 156 |
Figure 22.4
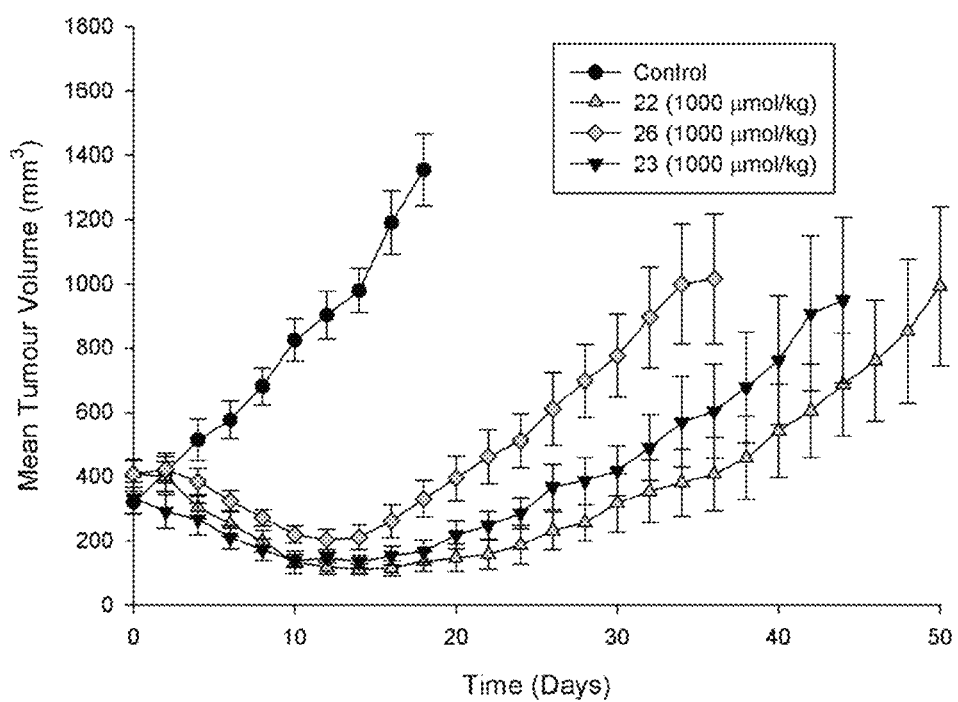

Figure 22.5

| Treatment | Dose (μmol/kg) | Median time to RTV4 (Days) | TGD (%) |
|---|---|---|---|
| Control | - | 18 | - |
| 22 | 1000 | 66 | 267 |
| 26 | 1000 | 48 | 167 |
| 23 | 1000 | 48 | 167 |

PRODRUGS AND METHODS OF USE THEREOF

CROSS REFERENCE TO RELATED APPLICATIONS

This is a continuation of U.S. application Ser. No. 14/423,359, filed on Feb. 23, 2015 as the U.S. national phase of PCT/NZ2013/000150, filed on Aug. 22, 2013, which claims the benefit of New Zealand Application No. 602004, filed Aug. 23, 2012, all of which are incorporated by reference herein in their entireties.

FIELD OF THE INVENTION

The invention relates to compounds of use as targeted cytotoxic agents and methods of use thereof. In particular embodiments, the invention relates to nitrobenzamide mustards, nitrobenzamide mustard alcohols and their corresponding phosphate esters.

BACKGROUND OF THE INVENTION

The use of tumour-selective prodrugs (relatively inactive compounds that can be selectively converted to more active compounds in vivo) is a valuable concept in cancer therapy (see for example, Denny, Eur. J: Med. Chem. (2001) 36,577). For example a prodrug may be converted into an anti-tumour agent under the influence of an enzyme that is linkable to a monoclonal antibody that will bind to a tumour associated antigen. The combination of such a prodrug with such an enzyme/monoclonal antibody conjugate represents a very powerful clinical agent. This approach to cancer therapy, often referred to as "antibody directed enzyme prodrug therapy"(ADEPT), is disclosed in international publication WO/1988/007378.

A further therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug within the tumour cells (Huber et al., Proc. Natl. Acad. Sci. USA (1991) 88, 8039). Alternatively, non-viral methods for the delivery of genes have been used. Such methods include calcium phosphate co-precipitation, microinjection, liposomes, direct DNA uptake, and receptor mediated DNA-transfer. These are reviewed in Morgan & French, Annu. Rev. Biochem., 1993, 62; 191. The term "GDEPT" (gene-directed enzyme prodrug therapy) is used to include both viral and non-viral delivery systems (Denny et al U.S. Pat. No. 6,310,237). One example of a non-viral delivery system being the tumour colonising bacteria *Clostridia*, utilised in an approach termed clostridia-directed enzyme prodrug therapy (CD-EPT).

Many nitroaromatic compounds can be reduced by both mammalian and bacterial flavoprotein enzymes, which effect stepwise addition of up to six electrons. The major enzymatic metabolite is usually the 4-electron reduced species (hydroxylamine). A number of nitrophenyl mustards and nitrophenylaziridines have been reported as prodrugs for use in gene-directed enzyme prodrug therapy (GDEPT) in conjunction with nitroreductase enzymes. In particular, CB 1954 [5-(aziridin-1-yl)-2,4-dinitrobenzamide] (compound 1, scheme 1) is reported to be a substrate for the aerobic bacterial nitroreductase NTR (nfsB gene product) isolated from *E. coli* (Boland et al., Biochem. Pharmacol. 1991, 41, 867-875; Anlezark et al., Biochem. Pharmacol, 15, 1992, 44, 2289-2295; Parkinson et al., J. Med. Chem. 2000, 43, 3624). This compound has been used as a prodrug in both ADEPT (Knox et al., Biochem. Pharmacol., 1995, 49, 1641-1647) and GDEPT (Bridgewater et al., Eur. J. Cancer, 1995, 31A, 2362-2370; Bailey et al., Gene Ther., 1996, 3, 1143-1150; Bailey and Hart, Gene Ther., 1997, 4, 80-81; Green et al., Cancer Gene Ther., 1997, 4, 229-238) applications, including a clinical trial (Chung-Faye et al., Clin. Cancer Res., 2001, 7, 2662-2668). Similarly, the dinitrophenyl mustard SN 23862 (compound 2, scheme 1) is also a substrate for *E. coli* NfsB, and shows selective toxicity towards cell lines that express the enzyme. It is activated by nitro group reduction (Palmer et al., J. Med. Chem., 1995, 38, 1229; Kestell et al., Cancer Chemother. Pharmacol., 2000, 46, 365-374). The 4-SO$_2$Me derivative (compound 3, scheme 1) was also a substrate (Atwell et al., Anti-Cancer Drug Des., 1996, 11, 553), as was the dibromo mustard analogue (compound 4, scheme 1) (Atwell et al., J. Med. Chem., 2007, 50, 1197-1212). Prodrugs 1-4 (scheme 1) have poor aqueous solubility. For example, to determine the efficacy of prodrug 4 in xenograft-bearing nude mice, it was administered in either neat DMSO or DMSO/polyethylene glycol/water (Atwell et al., J. Med. Chem., 2007, 50, 1197-1212) resulting in a large variations in maximum tolerated dose.

Scheme 1

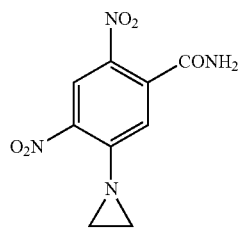

1

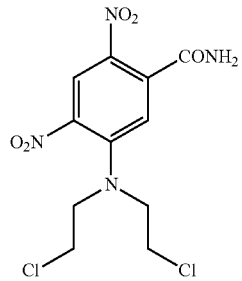

2

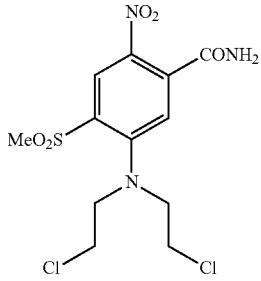

3

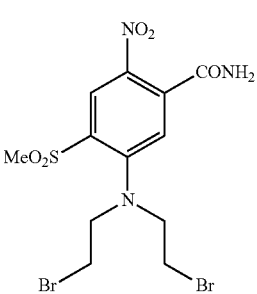

4

Some phosphate analogues of mustards have been described, for the purpose of solubilising the compounds. The best known is estramustine phosphate, which has been shown to bind to tubulin binding domains on various microtubule-associated proteins (Moraga et al., Biochim. Biophys. Acta, 1992, 1 121, 97-103), and which has been shown to be active in advanced breast cancer (Keren-Rosenberg et al., Semin. Oncol., 1997, 24(Suppl. 3), 26-29), but has not been shown to be activated by NTR.

Dinitrobenzamide mustards bearing alcohol side chains pendant at a carboxamide (—CONH—) group and their phosphate derivatives are described as bioreductive drugs for GDEPT applications (WO/2008/030112 and WO/2005/042471). Central to the disclosure are prodrugs that provide cell ablation with substantially minimal bystander effect, a term used to describe the back diffusion of cytotoxic metabolites from bacterial nitroreductase-expressing target cells to ablate bacterial nitroreductase naive cells. No bystander efficiency data is provided.

The ability to sterilise neighbouring cells otherwise unable to activate the targeted cytotoxic agent is of central importance to the activity of the agents in combination with nitroreductase enzymes. Gene/enzyme delivery technologies utilised in approaches such as GDEPT, VDEPT, CDEPT and ADEPT are inherently heterogeneous, necessitating efficient redistribution of activated cytotoxic metabolites to inhibit a larger population of neighbouring cells. Thus the bystander effect is an important mechanism to compensate for this anticipated heterogeneity by generating cytotoxic metabolites that diffuse locally to ablate neighbouring vector-naïve cells.

In addition to activation by exogenous oxygen-independent two-electron nitroreductases it is desirable to design nitroaromatic prodrugs, bearing a nitro substituent of an appropriate electron affinity that it is able to be reduced by endogenous human one-electron reductases to produce a nitro radical anion that can be readily back-oxidised by molecular oxygen. In well-oxygenated tissues in the body the parent prodrug is re-formed in a futile redox cycle, however in the presence of pathological hypoxia found in human solid tumours, net reduction to hydroxylamine and amine cytotoxic metabolites is able to occur providing tumour-selective cell killing. Such compounds are termed hypoxia-activated prodrugs (HAP) or hypoxia-selective cytotoxins (HSC).

The Phase II clinical candidate PR-104 is a 3,5-dinitrobenzamide water-soluble phosphate pre-prodrug that, following hydrolysis by systemic phosphatases, releases the 'hypoxia-activated' and 'bacterial nitroreductase-activated' prodrug PR-104A. Metabolism of PR-104A by endogenous human one-electron reductases in hypoxic cells of a tumour or by exogenous oxygen-independent two-electron nitroreductases, such as bacterial nitroreductases genetically engineered to be expressed in a tumour, produces the DNA crosslinking mustard cytotoxic metabolites PR-104H and PR-104M (Scheme 2) (Patterson et al., *Clin Can Res* 2007, 13:3922-32).

Scheme 2

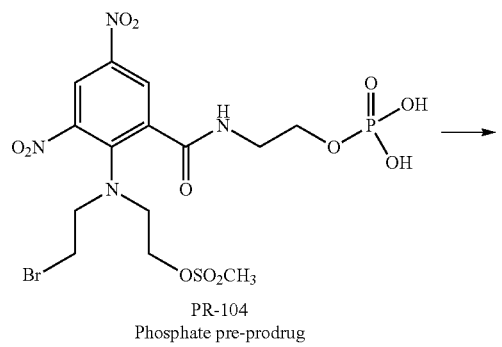

PR-104
Phosphate pre-prodrug

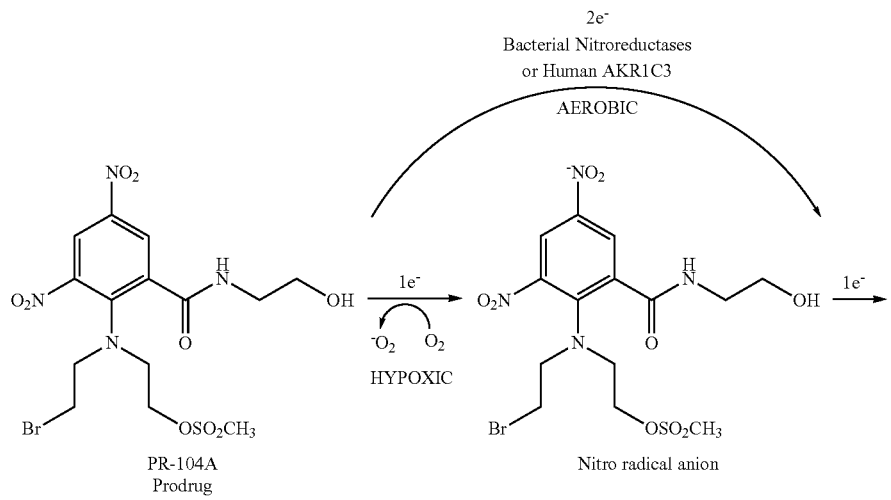

PR-104A
Prodrug

Nitro radical anion

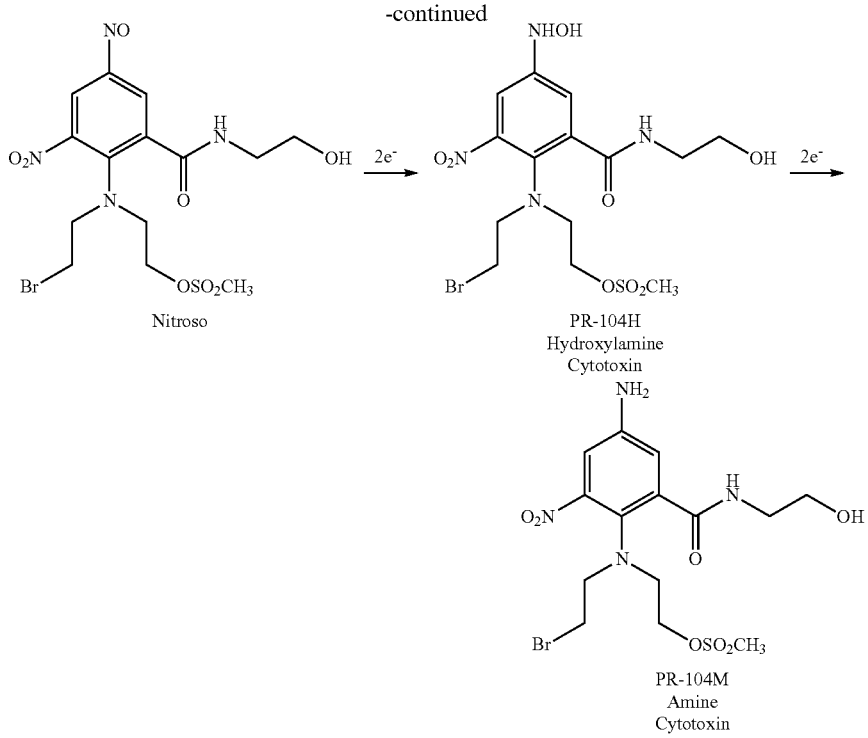

PR-104H
Hydroxylamine
Cytotoxin

PR-104M
Amine
Cytotoxin

Unexpectedly PR-104A is also subject to 2e-reduction by an endogenous human reductase called aldo-ketoreductase 1C3 (AKR1C3). This aerobic pathway yields identical cytotoxic metabolites. Expression of AKR1C3 in human CD34$^+$ myeloid progenitor cells may result in a lack of selectivity of PR-104 for solid tumours versus normal bone marrow, compromising PR-104's therapeutic index. It is desirable therefore to eliminate this off-mechanism aerobic activation of PR-104 by AKR1C3.

It is an object of the present invention to provide one or more prodrugs that are substantially free of activation by human AKR1C3 enzyme, or at least to provide the public with a useful choice.

SUMMARY OF THE INVENTION

In a first aspect of the invention there is provided a compound of Formula (I)

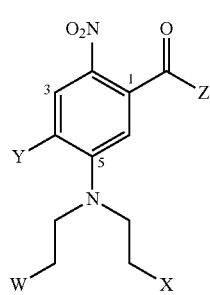

(I)

wherein W represents Cl, Br, I, OSO$_2$R,
X represents Cl, Br, I, OSO$_2$R,
Y represents H, CN, SO$_2$R,
each R independently represents a lower C$_{1-6}$ alkyl group,
Z is selected from any of the radicals of Formula (Ia)

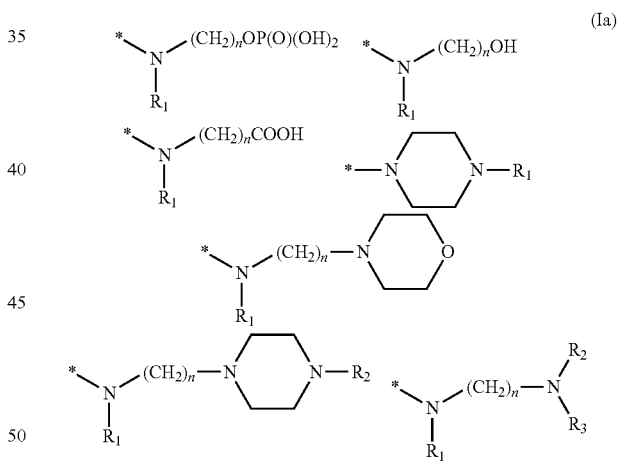

(Ia)

where
R$_1$ represents H, or a lower C$_{1-6}$ alkyl group;
R2 and R3 may independently represent H, or a lower C1-6 alkyl group, or
R2 and R3 together may be linked to form a substituted or unsubstituted heterocyclic ring comprising 5 or 6 members;
n represents 2 to 6;
* represents a point of attachment to Formula I;
or a pharmaceutically acceptable salt of said compound.

In a particular embodiment of the first aspect, the invention provides a compound of Formula (Ib)

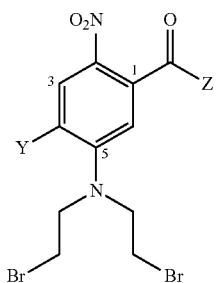

(Ib)

wherein Y represents H, CN, SO$_2$R,
R represents a methyl or ethyl group,
Z is selected from any of the radicals of Formula (Ic)

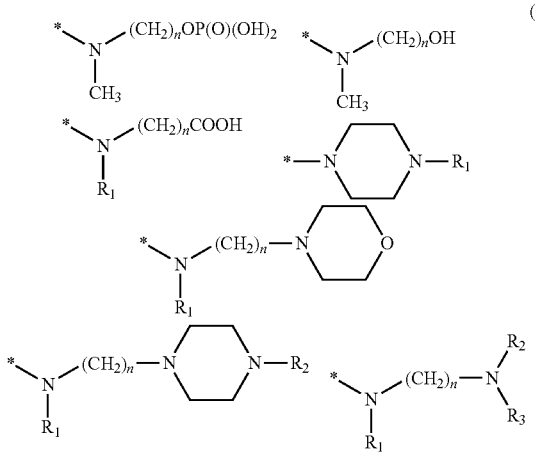

(Ic)

where
R$_1$ represents H, or a lower C$_{1-6}$ alkyl group;
R$_2$ and R$_3$ may independently represent H, or a lower C1-6 alkyl group, or
R$_2$ and R$_3$ together may be linked to form a substituted or unsubstituted heterocyclic ring comprising 5 or 6 members;
n represents 2 to 6;
* represents a point of attachment to Formula Ib;
or a pharmaceutically acceptable salt of said compound.

In one embodiment the compound of Formula (I) comprises a compound represented by formula (Id),

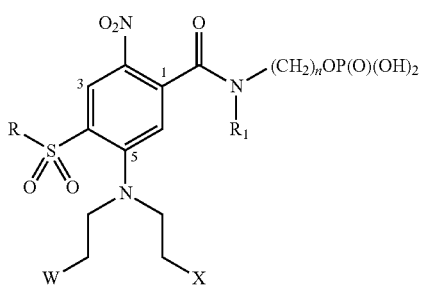

(Id)

wherein n represents 2 to 6,
W represents Cl, Br, I, OSO$_2$R,
X represents Cl, Br, I, OSO$_2$R,
each R independently represents a lower C$_{1-6}$ alkyl group, and
R$_1$ represents H, or a lower C$_{1-6}$ alkyl group.

In another embodiment W is bromine or iodine.
In another embodiment X is bromine or OSO$_2$Me.
In another embodiment R is methyl or ethyl.
In another embodiment R$_1$ is hydrogen, methyl or ethyl.
In another embodiment n represents 2 or 3 In a particular embodiment, the compound of Formula (I) comprises a compound represented by formula (Ie),

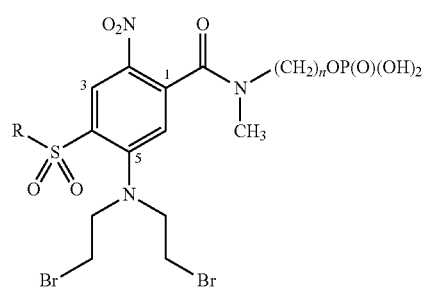

(Ie)

wherein n represents 2 to 6, and
R represents methyl or ethyl.

In another embodiment the compound of Formula (I) is selected from:
2-(5-(bis(2-bromoethyl)amino)-N-methyl-4-(methylsulfonyl)-2-nitrobenzamido)ethyl dihydrogen phosphate (compound 10),
2-(5-(bis(2-bromoethyl)amino)-4-(ethylsulfonyl)-N-methyl-2-nitrobenzamido)ethyl dihydrogen phosphate (compound 11),
3-(5-(bis(2-bromoethyl)amino)-N-methyl-4-(methylsulfonyl)-2-nitrobenzamido)propyl dihydrogen phosphate (compound 12),
3-(5-(bis(2-bromoethyl)amino)-4-(ethylsulfonyl)-N-methyl-2-nitrobenzamido)propyl dihydrogen phosphate (compound 13),
2-(5-(bis(2-bromoethyl)amino)-4-cyano-N-methyl-2-nitrobenzamido)ethyl dihydrogen phosphate (compound 69),
3-(5-(bis(2-bromoethyl)amino)-4-cyano-N-methyl-2-nitrobenzamido)propyl dihydrogen phosphate (compound 70),
2-(5-(bis(2-bromoethyl)amino)-4-(methylsulfonyl)-2-nitrobenzamido)ethyl dihydrogen phosphate (compound 300),
3-(5-(bis(2-bromoethyl)amino)-4-(methylsulfonyl)-2-nitrobenzamido)propyl dihydrogen phosphate (compound 308),
3-(5-(bis(2-bromoethyl)amino)-4-(ethylsulfonyl)-2-nitrobenzamido)propyl dihydrogen phosphate (compound 309),
2-((2-bromoethyl)(2-cyano-5-(methyl(2-(phosphonooxy)ethyl)carbamoyl)-4-nitrophenyl)amino)ethyl methanesulfonate (compound 350), and
2-((2-bromoethyl)(2-cyano-5-(methyl(3-(phosphonooxy)propyl)carbamoyl)-4-nitrophenyl)amino)ethyl methanesulfonate (compound 351).

In another embodiment the compound of Formula (I) is selected from a compound represented by formula (If),

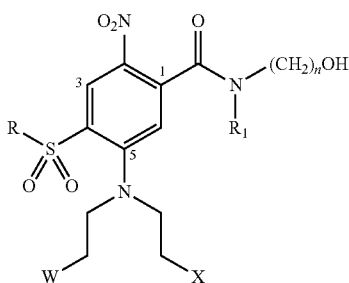

(If)

wherein n represents 2 to 6,
W represents Cl, Br, I, OSO$_2$R,
X represents Cl, Br, I, OSO$_2$R,
each R independently represents a lower C$_{1-6}$ alkyl group, and
R$_1$ represents H, or a lower C$_{1-6}$ alkyl group.

In another embodiment W is bromine or iodine.
In another embodiment X is bromine or OSO$_2$Me.
In another embodiment R is methyl or ethyl.
In another embodiment R$_1$ is hydrogen, methyl or ethyl.
In another embodiment n represents 2 or 3

In particular embodiment, the compound of Formula (I) is selected from a compound represented by formula (Ig),

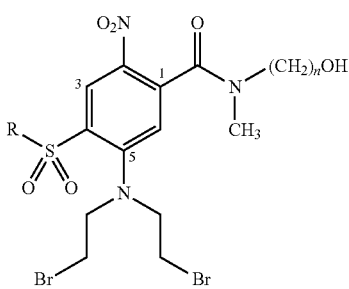

(Ig)

wherein n represents 2 to 6,
R represents methyl or ethyl.

In another embodiment the compound of Formula (I) is selected from:
5-(bis(2-bromoethyl)amino)-N-(2-hydroxyethyl)-N-methyl-4-(methylsulfonyl)-2-nitrobenzamide (compound 14),
5-(bis(2-bromoethyl)amino)-N-(3-hydroxypropyl)-N-methyl-4-(methylsulfonyl)-2-nitrobenzamide (compound 17),
5-(bis(2-bromoethyl)amino)-4-(ethylsulfonyl)-N-(2-hydroxyethyl)-N-methyl-2-nitrobenzamide (compound 18),
5-(bis(2-bromoethyl)amino)-4-cyano-N-(2-hydroxyethyl)-N-methyl-2-nitrobenzamide (compound 67),
5-(bis(2-bromoethyl)amino)-4-cyano-N-(3-hydroxypropyl)-N-methyl-2-nitrobenzamide (compound 68),
5-(bis(2-bromoethyl)amino)-N-(2-hydroxyethyl)-4-(methylsulfonyl)-2-nitrobenzamide (compound 301),
5-(bis(2-bromoethyl)amino)-4-(ethylsulfonyl)-N-(3-hydroxypropyl)-N-methyl-2-nitrobenzamide (compound 305),
5-(bis(2-bromoethyl)amino)-N-(3-hydroxypropyl)-4-(methylsulfonyl)-2-nitrobenzamide (compound 306),
5-(bis(2-bromoethyl)amino)-4-(ethylsulfonyl)-N-(3-hydroxypropyl)-2-nitrobenzamide (compound 307),
2-((2-bromoethyl)(2-cyano-5-((2-hydroxyethyl)(methyl)carbamoyl)-4-nitrophenyl)amino)ethyl methanesulfonate (compound 348), and
2-((2-bromoethyl)(2-cyano-5-((3-hydroxypropyl)(methyl)carbamoyl)-4-nitrophenyl)amino)ethyl methanesulfonate (compound 349).

In another embodiment the compound of Formula (I) is selected from a compound represented by formula (Ih)

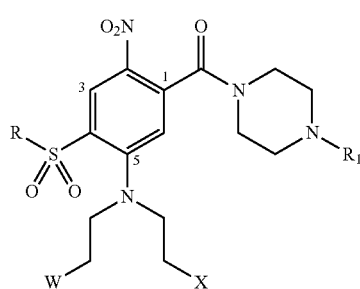

(Ih)

wherein W represents Cl, Br, I, OSO$_2$R,
X represents Cl, Br, I, OSO$_2$R,
each R independently represents a lower C$_{1-6}$alkyl group,
R$_1$ represents H, or a lower C$_{1-6}$alkyl group.

In another embodiment W is bromine or iodine.
In another embodiment X is bromine or OSO$_2$Me.
In another embodiment R is methyl or ethyl.
In another embodiment R$_1$ is methyl, ethyl, propyl or iso-propyl.

In another embodiment the compound of Formula (I) is selected from a compound represented by formula (Ii),

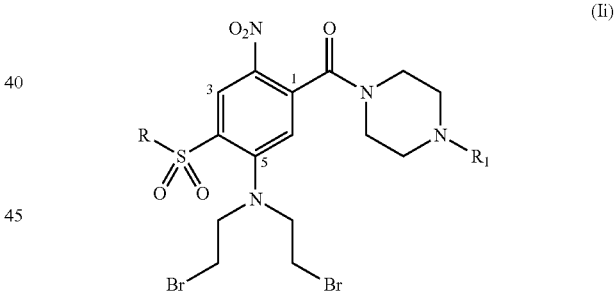

(Ii)

wherein R represents a lower C$_{1-6}$alkyl group,
R$_1$ represents H, or a lower C$_{1-6}$ alkyl group.

In another embodiment R is methyl or ethyl.
In another embodiment R$_1$ is methyl or ethyl.

In another embodiment the compound of Formula (I) defined above is selected from:
(5-(bis(2-bromoethyl)amino)-4-(methylsulfonyl)-2-nitrophenyl)(4-methylpiperazin-1-yl)methanone (compound 22),
(5-(bis(2-bromoethyl)amino)-4-(methylsulfonyl)-2-nitrophenyl)(4-ethylpiperazin-1-yl)methanone (compound 23),
(5-(bis(2-bromoethyl)amino)-4-(methylsulfonyl)-2-nitrophenyl)(4-isopropylpiperazin-1-yl)methanone (compound 24),
(5-(bis(2-bromoethyl)amino)-4-(ethylsulfonyl)-2-nitrophenyl)(4-methylpiperazin-1-yl)methanone (compound 25),
(5-(bis(2-bromoethyl)amino)-4-(ethylsulfonyl)-2-nitrophenyl)(4-ethylpiperazin-1-yl)methanone (compound 26), (5-(bis(2-bromoethyl)amino)-4-(ethylsulfonyl)-2-nitrophenyl)(4-isopropylpiperazin-1-yl)methanone (compound 27), 5-(bis(2-bromoethyl)amino)-4-(methylsulfonyl)-N-(2-morpholinoethyl)-2-nitrobenzamide (compound 28), 5-(bis(2-bromoethyl)amino)-N-methyl-4-(methylsulfonyl)-N-(2-morpholinoethyl)-2-nitrobenzamide (compound 29), 5-(bis(2-bromoethyl)amino)-4-(methylsulfonyl)-N-(3-morpholinopropyl)-2-nitrobenzamide (compound 30), 5-(bis(2-bromoethyl)amino)-N-methyl-4-(methylsulfonyl)-N-(3-morpholinopropyl)-2-nitrobenzamide (compound 31), 5-(bis(2-bromoethyl)amino)-N-(2-(4-methylpiperazin-1-yl)ethyl)-4-(methylsulfonyl)-2-nitrobenzamide (compound 32), 5-(bis(2-bromoethyl)amino)-N-methyl-N-(2-(4-methylpiperazin-1-yl)ethyl)-4-(methylsulfonyl)-2nitrobenzamide (compound 33), 5-(bis(2-bromoethyl)amino)-N-(3-(4-methylpiperazin-1-yl)propyl)-4-(methylsulfonyl)-2-nitrobenzamide (compound 34), 5-(bis(2-bromoethyl)amino)-N-methyl-N-(3-(4-methylpiperazin-1-yl)propyl)-4-(methylsulfonyl)-2-nitrobenzamide (compound 35), 5-(bis(2-bromoethyl)amino)-N-(2-(dimethylamino)ethyl)-4-(methylsulfonyl)-2-nitrobenzamide (compound 36), 5-(bis(2-bromoethyl)amino)-N-(2-(dimethylamino)ethyl)-N-methyl-4-(methylsulfonyl)-2-nitrobenzamide (compound 37), 5-(bis(2-bromoethyl)amino)-N-(3-(dimethylamino)propyl)-4-(methylsulfonyl)-2-nitrobenzamide (compound 38), 5-(bis(2-bromoethyl)amino)-N-(3-(dimethylamino)propyl)-N-methyl-4-(methylsulfonyl)-2-nitrobenzamide (compound 39), 5-(bis(2-bromoethyl)amino)-4-(ethylsulfonyl)-N-(2-morpholinoethyl)-2-nitrobenzamide (compound 40), 5-(bis(2-bromoethyl)amino)-4-(ethylsulfonyl)-N-methyl-N-(2-morpholinoethyl)-2-nitrobenzamide (compound 41), 5-(bis(2-bromoethyl)amino)-4-(ethylsulfonyl)-N-(3-morpholinopropyl)-2-nitrobenzamide (compound 42), 5-(bis(2-bromoethyl)amino)-4-(ethylsulfonyl)-N-methyl-N-(3-morpholinopropyl)-2-nitrobenzamide (compound 43), 5-(bis(2-bromoethyl)amino)-4-(ethylsulfonyl)-N-(2-(4-methylpiperazin-1-yl)ethyl)-2-nitrobenzamide (compound 44), 5-(bis(2-bromoethyl)amino)-4-(ethylsulfonyl)-N-methyl-N-(2-(4-methylpiperazin-1-yl)ethyl)-2-nitrobenzamide (compound 45), 5-(bis(2-bromoethyl)amino)-4-(ethylsulfonyl)-N-(3-(4-methylpiperazin-1-yl)propyl)-2-nitrobenzamide (compound 46), 5-(bis(2-bromoethyl)amino)-4-(ethylsulfonyl)-N-methyl-N-(3-(4-methylpiperazin-1-yl)propyl)-2-nitrobenzamide (compound 47), 5-(bis(2-bromoethyl)amino)-N-(2-(dimethylamino)ethyl)-4-(ethylsulfonyl)-2-nitrobenzamide (compound 48), 5-(bis(2-bromoethyl)amino)-N-(2-(dimethylamino)ethyl)-4-(ethylsulfonyl)-N-methyl-2-nitrobenzamide (compound 49), 5-(bis(2-bromoethyl)amino)-N-(3-(dimethylamino)propyl)-4-(ethylsulfonyl)-2-nitrobenzamide (compound 50), 5-(bis(2-bromoethyl)amino)-N-(3-(dimethylamino)propyl)-4-(ethylsulfonyl)-N-methyl-2-nitrobenzamide (compound 51), 3-(5-(bis(2-bromoethyl)amino)-4-(methylsulfonyl)-2-nitrobenzamido)propanoic acid (compound 52), 4-(5-(bis(2-bromoethyl)amino)-4-(methylsulfonyl)-2-nitrobenzamido)butanoic acid (compound 53), 3-(5-(bis(2-bromoethyl)amino)-N-methyl-4-(methylsulfonyl)-2-nitrobenzamido)propanoic acid (compound 54), 4-(5-(bis(2-bromoethyl)amino)-N-methyl-4-(methylsulfonyl)-2-nitrobenzamido)butanoic acid (compound 55), 3-(5-(bis(2-bromoethyl)amino)-4-(ethylsulfonyl)-2-nitrobenzamido)propanoic acid (compound 56), 4-(5-(bis(2-bromoethyl)amino)-4-(ethylsulfonyl)-2-nitrobenzamido)butanoic acid (compound 57), 3-(5-(bis(2-bromoethyl)amino)-4-(ethylsulfonyl)-N-methyl-2-nitrobenzamido)propanoic acid (compound 58), 4-(5-(bis(2-bromoethyl)amino)-4-(ethylsulfonyl)-N-methyl-2-nitrobenzamido)butanoic acid (compound 59)

2-(bis(2-bromoethyl)amino)-4-(4-methylpiperazine-1-carbonyl)-5-nitrobenzonitrile (compound 71), 2-(bis(2-bromoethyl)amino)-4-(4-ethylpiperazine-1-carbonyl)-5-nitrobenzonitrile (compound 72), 2-(bis(2-bromoethyl)amino)-4-(4-isopropylpiperazine-1-carbonyl)-5-nitrobenzonitrile (compound 73), 3-(5-(bis(2-bromoethyl)amino)-4-cyano-2-nitrobenzamido)propanoic acid (compound 74), 4-(5-(bis(2-bromoethyl)amino)-4-cyano-2-nitrobenzamido)butanoic acid (compound 75), 3-(5-(bis(2-bromoethyl)amino)-4-cyano-N-methyl-2-nitrobenzamido)propanoic acid (compound 76), 4-(5-(bis(2-bromoethyl)amino)-4-cyano-N-methyl-2-nitrobenzamido)butanoic acid (compound 77), 5-(bis(2-bromoethyl)amino)-4-cyano-N-(2-morpholinoethyl)-2-nitrobenzamide (compound 78), 5-(bis(2-bromoethyl)amino)-4-cyano-N-methyl-N-(2-morpholinoethyl)-2-nitrobenzamide (compound 79), 5-(bis(2-bromoethyl)amino)-4-cyano-N-(3-morpholinopropyl)-2-nitrobenzamide (compound 80), 5-(bis(2-bromoethyl)amino)-4-cyano-N-methyl-N-(3-morpholinopropyl)-2-nitrobenzamide (compound 81), 5-(bis(2-bromoethyl)amino)-4-cyano-N-(2-(4-methylpiperazin-1-yl)ethyl)-2-nitrobenzamide (compound 82), 5-(bis(2-bromoethyl)amino)-4-cyano-N-methyl-N-(2-(4-methylpiperazin-1-yl)ethyl)-2-nitrobenzamide (compound 83), 5-(bis(2-bromoethyl)amino)-4-cyano-N-(3-(4-methylpiperazin-1-yl)propyl)-2-nitrobenzamide (compound 84), 5-(bis(2-bromoethyl)amino)-4-cyano-N-methyl-N-(3-(4-methylpiperazin-1-yl)propyl)-2-nitrobenzamide (compound 85), 5-(bis(2-bromoethyl)amino)-4-cyano-N-(2-(dimethylamino)ethyl)-2-nitrobenzamide (compound 86), 5-(bis(2-bromoethyl)amino)-4-cyano-N-(2-(dimethylamino)ethyl)-N-methyl-2-nitrobenzamide (compound 87), 5-(bis(2-bromoethyl)amino)-4-cyano-N-(3-(dimethylamino)propyl)-2-nitrobenzamide (compound 88), 5-(bis(2-bromoethyl)amino)-4-cyano-N-(3-(dimethylamino)propyl)-N-methyl-2-nitrobenzamide (compound 89), 2-((2-bromoethyl)(5-(4-methylpiperazine-1-carbonyl)-2-(methylsulfonyl)-4-nitrophenyl)amino)ethyl methanesulfonate (compound 310), 2-((2-bromoethyl)(5-(4-ethylpiperazine-1-carbonyl)-2-(methylsulfonyl)-4-nitrophenyl)amino)ethyl methanesulfonate (compound 311), 2-((2-bromoethyl)(5-(4-isopropylpiperazine-1-carbonyl)-2-(methylsulfonyl)-4-nitrophenyl)amino)ethyl methanesulfonate (compound 312), 2-((2-bromoethyl)(2-(ethylsulfonyl)-5-(4-methylpiperazine-1-carbonyl)-4-nitrophenyl)amino)ethyl methanesulfonate (compound 313), 2-((2-bromoethyl)(5-(4-ethylpiperazine-1-carbonyl)-2-(ethylsulfonyl)-4-nitrophenyl)amino)ethyl methanesulfonate (compound 314), 2-((2-bromoethyl)(2-(ethylsulfonyl)-5-(4-isopropylpiperazine-1-carbonyl)-4-nitrophenyl)amino)ethyl methanesulfonate (compound 315), 2-((2-bromoethyl)(2-(methylsulfonyl)-5-((2-morpholinoethyl)carbamoyl)-4-nitrophenyl)amino)ethyl methanesulfonate (compound 316), 2-((2-bromoethyl)(5-(methyl(2-morpholinoethyl)carbamoyl)-2-(methylsulfonyl)-4-nitrophenyl)amino)ethyl methanesulfonate (compound 317), 2-((2-bromoethyl)(2-(methylsulfonyl)-5-((3-morpholinopropyl)carbamoyl)-4-nitrophenyl)amino)ethyl methanesulfonate (compound 318), 2-((2-bromoethyl)(5-(methyl(3-morpholinopropyl)carbamoyl)-2-(methylsulfonyl)-4-nitrophenyl)amino)ethyl methanesulfonate (compound 319), 2-((2-bromoethyl)(5-((2-(4-methylpiperazin-1-yl)ethyl)carbamoyl)-2-(methylsulfonyl)-4-nitrophenyl)amino)ethyl methanesulfonate (compound 320), 2-((2-bromoethyl)(5-(methyl(2-(4-methylpiperazin-1-yl)ethyl)carbamoyl)-2-(methylsulfonyl)-4-nitrophenyl)amino)ethyl methanesulfonate (compound 321), 2-((2-bromoethyl)(5-((3-(4-methylpiperazin-1-yl)propyl)carbamoyl)-2-(methylsulfonyl)-4-nitrophenyl)amino)ethyl methanesulfonate (compound 322), 2-((2-bromoethyl)(5-(methyl(3-(4-methylpiperazin-1-yl)propyl)carbamoyl)-2-(methylsulfonyl)-4-nitrophenyl)amino)ethyl methanesulfonate (compound 323), 2-((2-bromoethyl)(5-((2-(dimethylamino)ethyl)carbamoyl)-2-(methylsulfonyl)-4-nitrophenyl)amino)ethyl methanesulfonate (compound 324), 2-((2-bromoethyl)(5-((2-(dimethylamino)ethyl)(methyl)carbamoyl)-2-(methylsulfonyl)-4-nitrophenyl)amino)ethyl methanesulfonate (compound 325), 2-((2-bromoethyl)(5-((3-(dimethylamino)propyl)carbamoyl)-2-(methylsulfonyl)-4-nitrophenyl)amino)ethyl methanesulfonate (compound 326), 2-((2-bromoethyl)(5-((3-(dimethylamino)propyl)(methyl)carbamoyl)-2-(methylsulfonyl)-4-nitrophenyl)amino)ethyl methanesulfonate (compound 327), 2-((2-bromoethyl)(2-(ethylsulfonyl)-5-((2-morpholinoethyl)carbamoyl)-4-nitrophenyl)amino)ethyl methanesulfonate (compound 328), 2-((2-bromoethyl)(2-(ethylsulfonyl)-5-(methyl(2-morpholinoethyl)carbamoyl)-4-nitrophenyl)amino)ethyl methanesulfonate (compound 329), 2-((2-bromoethyl)(2-(ethylsulfonyl)-5-((3-morpholinopropyl)carbamoyl)-4-nitrophenyl)amino)ethyl methanesulfonate (compound 330), 2-((2-bromoethyl)(2-(ethylsulfonyl)-5-(methyl(3-morpholinopropyl)carbamoyl)-4-nitrophenyl)amino)ethyl methanesulfonate (compound 331), 2-((2-bromoethyl)(2-(ethylsulfonyl)-5-((2-(4-methylpiperazin-1-yl)ethyl)carbamoyl)-4-nitrophenyl)amino)ethyl methanesulfonate (compound 332), 2-((2-bromoethyl)(2-(ethylsulfonyl)-5-(methyl(2-(4-methylpiperazin-1-yl)ethyl)carbamoyl)-4-nitrophenyl)amino)ethyl methanesulfonate (compound 333), 2-((2-bromoethyl)(2-(ethylsulfonyl)-5-((3-(4-methylpiperazin-1-yl)propyl)carbamoyl)-4-nitrophenyl)amino)ethyl methanesulfonate (compound 334), 2-((2-bromoethyl)(2-(ethylsulfonyl)-5-(methyl(3-(4-methylpiperazin-1-yl)propyl)carbamoyl)-4-nitrophenyl)amino)ethyl methanesulfonate (compound 335), 2-((2-bromoethyl)(5-((2-(dimethylamino)ethyl)carbamoyl)-2-(ethylsulfonyl)-4-nitrophenyl)amino)ethyl methanesulfonate (compound 336), 2-((2-bromoethyl)(5-((2-(dimethylamino)ethyl)(methyl)carbamoyl)-2-(ethylsulfonyl)-4-nitrophenyl)amino)ethyl methanesulfonate (compound 337), 2-((2-bromoethyl)(5-((3-(dimethylamino)propyl)carbamoyl)-2-(ethylsulfonyl)-4-nitrophenyl)amino)ethyl methanesulfonate (compound 338), 2-((2-bromoethyl)(5-((3-(dimethylamino)propyl)(methyl)carbamoyl)-2-(ethylsulfonyl)-4-nitrophenyl)amino)ethyl methanesulfonate (compound 339), 3-(5-((2-bromoethyl)(2-((methylsulfonyl)oxy)ethyl)amino)-4-(methylsulfonyl)-2-nitrobenzamido)propanoic acid (compound 340), 4-(5-((2-bromoethyl)(2-((methylsulfonyl)oxy)ethyl)amino)-4-(methylsulfonyl)-2-nitrobenzamido)butanoic acid (compound 341), 3-(5-((2-bromoethyl)(2-((methylsulfonyl)oxy)ethyl)amino)-N-methyl-4-(methylsulfonyl)-2-nitrobenzamido)propanoic acid (compound 342), 4-(5-((2-bromoethyl)(2-((methylsulfonyl)oxy)ethyl)amino)-N-methyl-4-(methylsulfonyl)-2-nitrobenzamido)butanoic acid (compound 343), 3-(5-((2-bromoethyl)(2-((methylsulfonyl)oxy)ethyl)amino)-4-(ethylsulfonyl)-2-nitrobenzamido)propanoic acid (compound 344), 4-(5-((2-bromoethyl)(2-((methylsulfonyl)oxy)ethyl)amino)-4-(ethylsulfonyl)-2-nitrobenzamido)butanoic acid (compound 345), 3-(5-((2-bromoethyl)(2-((methylsulfonyl)oxy)ethyl)amino)-4-(ethylsulfonyl)-N-methyl-2-nitrobenzamido)propanoic acid (compound 346), 4-(5-((2-bromoethyl)(2-((methylsulfonyl)oxy)ethyl)amino)-4-(ethylsulfonyl)-N-methyl-2-nitrobenzamido)butanoic acid (compound 347), 2-((2-bromoethyl)(2-cyano-5-(4-methylpiperazine-1-carbonyl)-4-nitrophenyl)amino)ethyl methanesulfonate (compound 352), 2-((2-bromoethyl)(2-cyano-5-(4-ethylpiperazine-1-carbonyl)-4-nitrophenyl)amino)ethyl methanesulfonate (compound 353), 2-((2-bromoethyl)(2-cyano-5-(4-isopropylpiperazine-1-carbonyl)-4-nitrophenyl)amino)ethyl methanesulfonate (compound 354), 3-(5-((2-bromoethyl)(2-((methylsulfonyl)oxy)ethyl)amino)-4-cyano-2-nitrobenzamido)propanoic acid (compound 355), 4-(5-((2-bromoethyl)(2-((methylsulfonyl)oxy)ethyl)amino)-4-cyano-2-nitrobenzamido)butanoic acid (compound 356), 3-(5-((2-bromoethyl)(2-((methylsulfonyl)oxy)ethyl)amino)-4-cyano-N-methyl-2-nitrobenzamido)propanoic acid (compound 357), 4-(5-((2-bromoethyl)(2-((methylsulfonyl)oxy)ethyl)amino)-4-cyano-N-methyl-2-nitrobenzamido)butanoic acid (compound 358), 2-((2-bromoethyl)(2-cyano-5-((2-morpholinoethyl)carbamoyl)-4-nitrophenyl)amino)ethyl methanesulfonate (compound 359), 2-((2-bromoethyl)(2-cyano-5-(methyl(2-morpholinoethyl)carbamoyl)-4-nitrophenyl)amino)ethyl methanesulfonate (compound 360), 2-((2-bromoethyl)(2-cyano-5-((3-morpholinopropyl)car-bamoyl)-4-nitrophenyl)amino)ethyl methanesulfonate (compound 361),
2-((2-bromoethyl)(2-cyano-5-(methyl(3-morpholinopropyl)carbamoyl)-4-nitrophenyl)amino)ethyl methanesulfonate (compound 362),
2-((2-bromoethyl)(2-cyano-5-((2-(4-methylpiperazin-1-yl)ethyl)carbamoyl)-4-nitrophenyl)amino)ethyl methanesulfonate (compound 363),
2-((2-bromoethyl)(2-cyano-5-(methyl(2-(4-methylpiperazin-1-yl)ethyl)carbamoyl)-4-nitrophenyl)amino)ethyl methanesulfonate (compound 364),
2-((2-bromoethyl)(2-cyano-5-((3-(4-methylpiperazin-1-yl)propyl)carbamoyl)-4-nitrophenyl)amino)ethyl methanesulfonate (compound 365),
2-((2-bromoethyl)(2-cyano-5-(methyl(3-(4-methylpiperazin-1-yl)propyl)carbamoyl)-4-nitrophenyl)amino)ethyl methanesulfonate (compound 366),
2-((2-bromoethyl)(2-cyano-5-((2-(dimethylamino)ethyl)carbamoyl)-4-nitrophenyl)amino)ethyl methanesulfonate (compound 367),
2-((2-bromoethyl)(2-cyano-5-((2-(dimethylamino)ethyl)(methyl)carbamoyl)-4-nitrophenyl)amino)ethyl methanesulfonate (compound 368),
2-((2-bromoethyl)(2-cyano-5-((3-(dimethylamino)propyl)carbamoyl)-4-nitrophenyl)amino)ethyl methanesulfonate (compound 369), and
2-((2-bromoethyl)(2-cyano-5-((3-(dimethylamino)propyl)(methyl)carbamoyl)-4-nitrophenyl)amino)ethyl methanesulfonate (compound 370).

In a second aspect of the invention there is provided a compound of Formula (II)

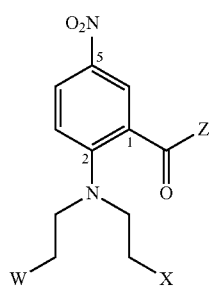

(II)

wherein W represents Cl, Br, I, OSO$_2$R,
X represents Cl, Br, I, OSO$_2$R,
each R independently represents a lower C$_{1-6}$ alkyl group,
Z is selected from any of the radicals of Formula (IIa)

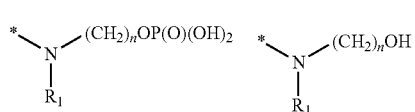

(IIa)

where
R$_1$ represents H, or a lower C$_{1-6}$ alkyl group,
n represents 2 to 6
* represents a point of attachment to Formula II
or a pharmaceutically acceptable salt thereof.

In a particular embodiment of the second aspect, the invention provides a compound of Formula (IIb)

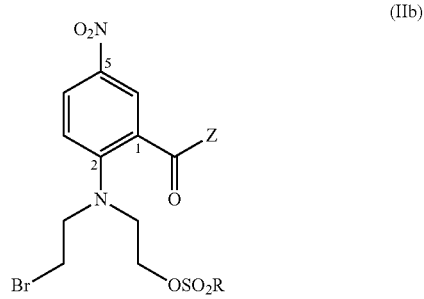

(IIb)

wherein R represents a lower C$_{1-6}$ alkyl group,
Z is selected from any of the radicals of Formula (IIc)

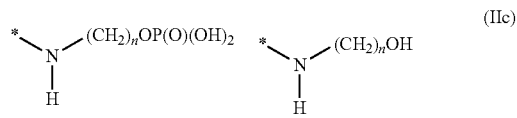

(IIc)

where
n represents 2 to 6
* represents a point of attachment to Formula IIb
or a pharmaceutically acceptable salt thereof.

In one embodiment the compound of Formula (II) comprises a compound represented by formula (IId),

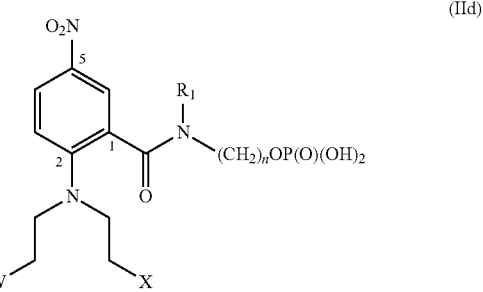

(IId)

wherein n represents 2 to 6,
W represents Cl, Br, I, OSO$_2$R,
X represents Cl, Br, I, OSO$_2$R,
R represents a lower C$_{1-6}$alkyl group,
R$_1$ represents H, or a lower C$_{1-6}$ alkyl group.
In another embodiment W is bromine or iodine.
In another embodiment X is bromine or OSO$_2$Me.
In another embodiment R$_1$ is hydrogen.
In another embodiment n represents 2 or 3
In one embodiment the compound of Formula (II) is selected from a compound represented by formula (IIe),

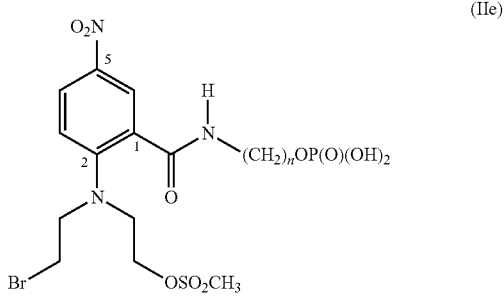

(IIe)

wherein n represents 2 to 6.
In another embodiment the compound of Formula (II) is selected from:

2-((2-bromoethyl)(4-nitro-2-((2-(phosphonooxy)ethyl)carbamoyl)phenyl)amino)ethyl methanesulfonate (compound 60), 2-((2-bromoethyl)(4-nitro-2-((3-(phosphonooxy)propyl)carbamoyl)phenyl)amino)ethyl methanesulfonate (compound 61), In another embodiment the compound of Formula (II) is selected from a compound represented by formula (IIf),

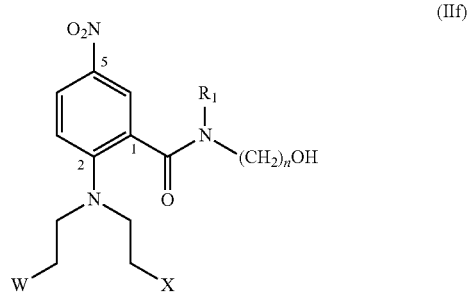

(IIf)

wherein n represents 2 to 6,

W represents Cl, Br, I, OSO$_2$R,

X represents Cl, Br, I, OSO$_2$R, each R independently represents a lower $C_{1-6}$ alkyl group, $R_1$ represents H, or a lower $C_{1-6}$ alkyl group.

In another embodiment W is bromine or iodine.

In another embodiment X is bromine or OSO$_2$Me.

In another embodiment $R_1$ is hydrogen.

In another embodiment n represents 2 or 3

In another embodiment the compound of Formula (II) is selected from a compound represented by formula (IIg),

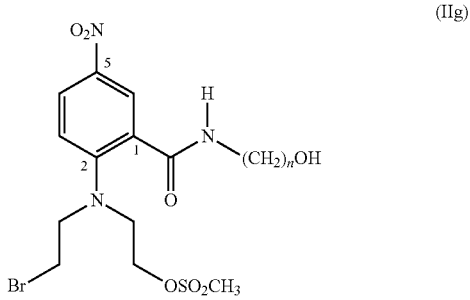

(IIg)

wherein n represents 2 to 6,

In another embodiment n represents 2 or 3

In another embodiment the compound of Formula (II) as claimed is selected from:

2-((2-bromoethyl)(2-((2-hydroxyethyl)carbamoyl)-4-nitrophenyl)amino)ethyl methanesulfonate (compound 64), 2-((2-bromoethyl)(2-((3-hydroxypropyl)carbamoyl)-4-nitrophenyl)amino)ethyl methanesulfonate (compound 66), In a particular embodiment, the solubility of the compound of the first or second aspect is greater than about 95 mM when determined in Phosphate Buffered Saline (PBS) containing 2 equivalents of sodium bicarbonate.

In a particular embodiment, the solubility of the compound of the first or second aspect is greater than about 10 mM when determined in Lactate Buffer at pH=4.

In a third aspect there is provided a method of cell ablation comprising the use of a compound of the first or second aspect or a mixture thereof. In a particular embodiment, the compound is a prodrug capable of activation by contact with a) at least one nitroreductase enzyme, and/or b) a low oxygen (hypoxic) environment.

In a particular embodiment, the method of cell ablation comprises:
a. selecting a compound of formula (I) which is substantially resistant to AKR1C3 enzyme metabolism;
b. contacting the compound of step a. with
 i. at least one nitroreductase enzyme, and/or
 ii. a hypoxic environment,
to produce a cytotoxic metabolite capable of ablating the cell;
c. contacting the cell with the cytotoxic metabolite;
wherein the compound of formula (I) is as defined in the first aspect.

In a particular embodiment, the method of cell ablation comprises:
a. selecting a compound of formula (II) which is substantially resistant to AKR1C3 enzyme metabolism;
b. contacting the compound of step a. with
 i. at least one nitroreductase enzyme, and/or
 ii. a hypoxic environment,
to produce a cytotoxic metabolite capable of ablating the cell;
c. contacting the cell with the cytotoxic metabolite;
wherein the compound of formula (II) is as defined in the second aspect.

Preferably, the hypoxic environment is a hypoxic region of a tumour.

Preferably the prodrug is capable of providing a substantial bystander effect which results in cell ablation.

In one embodiment of the third aspect, the cell is a tumour cell in tissue in a subject.

In one embodiment of the third aspect the cell is a mammalian cell.

In one embodiment of the third aspect, the method of cell ablation is a method of cancer treatment comprising the administration of the compound to a subject. Preferably, the amount of compound administered is a therapeutically effective amount. Preferably, this amount is between about 20% to 100% of the maximum tolerated dose of said subject.

In a particular embodiment of the third aspect the compound is administered to a subject in combination with at least one nitroreductase enzyme capable of metabolising the compound. In a particular embodiment, the compound is administered to a subject in combination with a therapy that results in expression of an exogenous nitroreductase enzyme within, or therapeutically proximate to, a tumour. In a further embodiment, the at least one nitroreductase enzyme is encoded for by the nfsB and/or the nfsA gene of either *E. coli* or by orthologous genes in other bacterial species. In a particular embodiment, the nitroreductase is a nitroreductase described in WO/2012/008860, which includes mutant nitroreductases and functionally equivalent variants of the nitroreductase described therein.

In a particular embodiment of the third aspect, the method includes the step of irradiating the cell. Preferably, irradiation is carried out before, concurrently with, or after administration of the prodrug. Preferably, the amount of absorbed radiation is 15 gray (Gy).

In a particular embodiment of the third aspect, the method includes the administration of a compound of the first or second aspect or mixture thereof in conjunction with GDEPT (gene-directed enzyme prodrug therapy), VDEPT (virus-directed enzyme prodrug therapy), CDEPT (clostridia-directed enzyme prodrug therapy) or ADEPT (antibody-directed enzyme prodrug therapy).

In a particular embodiment, the CDEPT comprises use of a *Clostridia* microorganism that is selective for colonising the necrosis found in tumours. Preferably, the *Clostridia* microorganism is a recombinant microorganism comprising one or more genes expressing a nitroreductase exogenous to the *Clostridia* microorganism. Preferably, the nitroreductase enzyme is encoded for by the nfsB and/or the nfsA gene of either *E. coli* or by orthologous genes in other bacterial species In a particular embodiment of the third aspect the method further includes the dissolution of the compound in an aqueous solution.

In a fourth aspect, the invention provides the use of a compound of the first or second aspect or a mixture thereof in the manufacture of a composition to ablate a cell. In a particular embodiment, the compound is a prodrug capable of activation by contact with a) at least one nitroreductase enzyme, and/or b) a low oxygen (hypoxic) environment.

In a fifth aspect, the invention provides the use of a compound as defined in the first or second aspect in the manufacture of a composition for the treatment of cancer or a hyperproliferative condition.

In a sixth aspect, the invention provides the use of a compound as defined in the first or second aspect for the treatment of cancer or a hyperproliferative condition.

In a seventh aspect of the invention there is provided a method of treatment of cancer or a hyperproliferative condition wherein a compound of the first or second aspect or a mixture thereof is administered in a therapeutically effective amount to a tumour cell, or therapeutically proximate to a tumour cell, in a subject.

In a particular embodiment of the seventh aspect, the therapeutically effective amount administered is between about 20% to 100% of the maximum tolerated dose of said subject.

In a particular embodiment of the seventh aspect the compound of the first or second aspect or mixture thereof is administered in conjunction with at least one nitroreductase enzyme. In a particular embodiment, the compound is administered to a subject in combination with a therapy that results in expression of an exogenous nitroreductase enzyme within, or therapeutically proximate to, a tumour.

In a particular embodiment of the seventh aspect, the at least one nitroreductase enzyme is encoded for by the nfsA or nfsB gene of either *E. coli* or by orthologous genes in other bacterial species. In a particular embodiment, the nitroreductase is a nitroreductase described in WO/2012/008860, which includes mutant nitroreductases and functionally equivalent variants of the nitroreductase described therein.

In a particular embodiment the method further comprises the activation of the compound of the first or second aspect by contact with the nitroreductase enzyme.

In a particular embodiment of the seventh aspect, the compound of the first or second aspect or mixture thereof is administered in conjunction with GDEPT (gene-directed enzyme prodrug therapy), VDEPT (virus-directed enzyme prodrug therapy), CDEPT (clostridia-directed enzyme prodrug therapy) or ADEPT (antibody-directed enzyme prodrug therapy).

In a particular embodiment, the CDEPT comprises use of a *Clostridia* microorganism that is selective for colonising the necrosis found in tumours. Preferably, the *Clostridia* microorganism is a recombinant microorganism comprising one or more genes expressing a nitroreductase exogenous to the *Clostridia* microorganism.

In a particular embodiment of the seventh aspect, the method of cancer treatment further includes the step of irradiating the tumour cells. Preferably, the irradiation is carried out before, concurrently with, or after the administration of the compound. Preferably, the amount of absorbed radiation is 15 gray (Gy).

In a particular embodiment of the seventh aspect, the method further includes the dissolution of the compound in an aqueous solution.

In an eighth aspect there is provided a pharmaceutical composition comprising a therapeutically effective amount of a compound of the first or second aspect, or a mixture thereof, and a pharmaceutically acceptable excipient, adjuvant, carrier, buffer or stabiliser.

In a particular embodiment, the composition is soluble in aqueous solution. Preferably, the solubility of the compound of the first or second aspect as found in the composition is greater than 95 mM when determined in Phosphate Buffered Saline (PBS) containing 2 equivalents of sodium bicarbonate.

In a ninth aspect, the invention provides a method of determining sensitivity of prodrugs to metabolism by AKR1C3 enzymes. The inventors have shown that the method of the ninth aspect provides a high cell density MCL screen that is surprisingly effective in detecting 'false negatives' from a two dimensional in vitro IC50 screen. The method also has particular utility in identification of bona fide AKR1C3-negative prodrugs, such as those of the present invention.

Further aspects of the invention, which should be considered in all its novel aspects, will become apparent to those skilled in the art upon reading of the following description which provides at least one example of a practical application of the invention.

BRIEF DESCRIPTION OF DRAWINGS

Embodiments of the invention will now be described, by way of example only, with reference to the accompanying drawings in which:

FIG. 4 shows representative 4-methylsulfonyl dibromo mustards bearing amine sidechains of Formula I FIG. 5 shows representative 4-ethylsulfonyl dibromo mustards bearing amine sidechains of Formula I FIG. 5.1 shows representative 4-methylsulfonyl bromomesylate mustards bearing amine sidechains of Formula I FIG. 5.2 shows representative 4-ethylsulfonyl bromomesylate mustards bearing amine sidechains of Formula I FIG. 6 shows representative dibromo mustards bearing acid sidechains of Formula I FIG. 6.1 shows representative bromomesylate mustards bearing acid sidechains of Formula I FIG. 7 shows representative phosphates of bromomesylate mustards of Formula II FIG. 7.1 shows representative bromomesylate mustard alcohols of Formula II FIG. 7.2 shows representative 4-cyano dibromo mustard alcohols, phosphates and amine sidechain bearing compounds of Formula I FIG. 7.2.1 shows representative 4-cyano bromomesylate mustard alcohols, phosphates and amine sidechain bearing compounds of Formula I FIG. 7.3 shows representative 4-cyano dibromo mustards bearing acid and amine sidechains of Formula I FIG. 7.4 shows representative 4-cyano bromomesylate mustards bearing acid and amine sidechains of Formula I Compounds X, XI and XII in FIG. 8, compound XII in FIG. 9.1, and compounds XI and XXIII in FIG. 9.1.1 each comprise three R groups. The two R groups attached to the —OSO$_2$ substituents will be identical using these methods of synthesis. The other R group attached to the sulphone —SO$_2$ group can vary independently of the other R groups while still being within the range defined for R in formula (I) where R represents a lower C$_{1-6}$ alkyl group.

FIG. 9.1 shows a preferred general synthetic scheme for the synthesis of 4-alkylsulfone prodrugs bearing a 1-position tertiary carboxamide of Formula I FIG. 9.1.1 shows a general synthetic scheme for the synthesis of 4-alkylsulfone prodrugs bearing acid sidechains of Formula I FIG. 9.1.2 shows a general synthetic scheme for synthesis of 4-cyano prodrugs of Formula I FIG. 9.1.3 shows a preferred general synthetic scheme for the synthesis of 4-cyano prodrugs bearing a 1-position tertiary carboxamide of Formula I FIG. 9.1.4 shows a general synthetic scheme for the synthesis of 4-cyano prodrugs bearing acid sidechains of Formula I FIG. 9.2 shows a scheme for synthesis of alcohol compound 14 (FIG. 2)

FIG. 9.3 shows a scheme for synthesis of alcohol compound 18 (FIG. 2)

FIG. 9.4 shows a scheme for synthesis of alcohol compound 301 (FIG. 2)

FIG. 17 shows clonogenic cell kill of PR-104A, prodrug 7 and prodrug 9 in HCT116 wild type Multicellular Layers (MCLs) versus HCT116 MCLs where the cells are engineered to over-express the human two-electron reductase aldo-ketoreductase 1C3 (AKR1C3). Prodrugs 7 and 9 are both capable of producing AKR1C3-dependent cell ablation, when cells are grown in three dimensional structures. Cytotoxic metabolites leaving the cell where they are produced are able to kill neighbouring cells. In a low cell density assay they are diluted into the assay media, protecting the cell of production from cytotoxicity, essentially providing an AKR1C3 false negative (see FIG. 15). The inventors have found that MCL assays are essential for identifying prodrugs that are free of AKR1C3 metabolism related cytotoxicity.

FIG. 17.1 shows the metabolism of compound 14 by members of the 55 candidate nitroreductase over-expression library as measured by GFP SOS assay. The data presented is the fold increase of GFP SOS response (normalised to culture density) exhibited by microplate cultures of E. coli strain SOS-R4 over-expressing candidate nitroreductases when challenged for 6 h with 20 μM of compound 14, compared to an unchallenged control. Data are the average of 2 independent assays and the error bars indicate ±1 standard deviation. The dashed line indicates the baseline activity for the empty plasmid control, and the data sets corresponding to the NfsA and NfsB family members are as marked. Inset: Metabolism of compound 14 was demonstrated for a selection of single and poly mutant variants of NfsA_Ec and NfsA_Bs. Data sets were generated in identical fashion to those described above for the 55 candidate nitroreductase library.

FIG. 17.2 shows the metabolism of compound 18 by members of the 55 candidate nitroreductase over-expression library as measured by GFP SOS assay. The data presented is the fold increase of GFP SOS response (normalised to culture density) exhibited by microplate cultures of E. coli strain SOS-R4 over-expressing candidate nitroreductases when challenged for 6 h with 20 μM of compound 18, compared to an unchallenged control. Data are the average of 2 independent assays and the error bars indicate ±1 standard deviation. The dashed line indicates the baseline activity for the empty plasmid control, and the data sets corresponding to the NfsA and NfsB family members are as marked. Inset: Metabolism of compound 18 was demonstrated for a selection of single and poly mutant variants of NfsA_Ec and NfsA_Bs. Data sets were generated in identical fashion to those described above for the 55 candidate nitroreductase library.

FIG. 17.3 shows the metabolism of compound 22 by members of the 55 candidate nitroreductase over-expression library as measured by GFP SOS assay. The data presented is the fold increase of GFP SOS response (normalised to culture density) exhibited by microplate cultures of E. coli strain SOS-R4 over-expressing candidate nitroreductases when challenged for 6 h with 50 μM of compound 22, compared to an unchallenged control. Data are the average of 2 independent assays and the error bars indicate ±1 standard deviation. The dashed line indicates the baseline activity for the empty plasmid control, and the data sets corresponding to the NfsA and NfsB family members are as marked. Inset: Metabolism of compound 22 was demonstrated for a selection of single and poly mutant variants of NfsA_Ec and NfsA_Bs. Data sets were generated in identical fashion to those described above for the 55 candidate nitroreductase library.

FIG. 17.4 shows the metabolism of compound 23 by members of the 55 candidate nitroreductase over-expression library as measured by GFP SOS assay. The data presented is the fold increase of GFP SOS response (normalised to culture density) exhibited by microplate cultures of E. coli strain SOS-R4 over-expressing candidate nitroreductases when challenged for 6 h with 60 µM of compound 23, compared to an unchallenged control. Data are the average of 2 independent assays and the error bars indicate ±1 standard deviation. The dashed line indicates the baseline activity for the empty plasmid control, and the data sets corresponding to the NfsA and NfsB family members are as marked. Inset: Metabolism of compound 23 was demonstrated for a selection of single and poly mutant variants of NfsA_Ec and NfsA_Bs. Data sets were generated in identical fashion to those described above for the 55 candidate nitroreductase library.

FIG. 17.5 shows the metabolism of compound 24 by members of the 55 candidate nitroreductase over-expression library as measured by GFP SOS assay. The data presented is the fold increase of GFP SOS response (normalised to culture density) exhibited by microplate cultures of E. coli strain SOS-R4 over-expressing candidate nitroreductases when challenged for 6 h with 60 µM of compound 24, compared to an unchallenged control. Data are the average of 2 independent assays and the error bars indicate ±1 standard deviation. The dashed line indicates the baseline activity for the empty plasmid control, and the data sets corresponding to the NfsA and NfsB family members are as marked. Inset: Metabolism of compound 24 was demonstrated for a selection of single and poly mutant variants of NfsA_Ec and NfsA_Bs. Data sets were generated in identical fashion to those described above for the 55 candidate nitroreductase library.

FIG. 17.6 shows the metabolism of compound 25 by members of the 55 candidate nitroreductase over-expression library as measured by GFP SOS assay. The data presented is the fold increase of GFP SOS response (normalised to culture density) exhibited by microplate cultures of E. coli strain SOS-R4 over-expressing candidate nitroreductases when challenged for 6 h with 60 µM of compound 25, compared to an unchallenged control. Data are the average of 2 independent assays and the error bars indicate ±1 standard deviation. The dashed line indicates the baseline activity for the empty plasmid control, and the data sets corresponding to the NfsA and NfsB family members are as marked. Inset: Metabolism of compound 25 was demonstrated for a selection of single and poly mutant variants of NfsA_Ec and NfsA_Bs. Data sets were generated in identical fashion to those described above for the 55 candidate nitroreductase library.

FIG. 17.7 shows the metabolism of compound 26 by members of the 55 candidate nitroreductase over-expression library as measured by GFP SOS assay. The data presented is the fold increase of GFP SOS response (normalised to culture density) exhibited by microplate cultures of E. coli strain SOS-R4 over-expressing candidate nitroreductases when challenged for 6 h with 60 µM of compound 26, compared to an unchallenged control. Data are the average of 2 independent assays and the error bars indicate ±1 standard deviation. The dashed line indicates the baseline activity for the empty plasmid control, and the data sets corresponding to the NfsA and NfsB family members are as marked. Inset: Metabolism of compound 26 was demonstrated for a selection of single and poly mutant variants of NfsA_Ec and NfsA_Bs. Data sets were generated in identical fashion to those described above for the 55 candidate nitroreductase library.

FIG. 17.8 shows the metabolism of compound 27 by members of the 55 candidate nitroreductase over-expression library as measured by GFP SOS assay. The data presented is the fold increase of GFP SOS response (normalised to culture density) exhibited by microplate cultures of E. coli strain SOS-R4 over-expressing candidate nitroreductases when challenged for 6 h with 60 µM of compound 27, compared to an unchallenged control. Data are the average of 2 independent assays and the error bars indicate ±1 standard deviation. The dashed line indicates the baseline activity for the empty plasmid control, and the data sets corresponding to the NfsA and NfsB family members are as marked. Inset: Metabolism of compound 27 was demonstrated for a selection of single and poly mutant variants of NfsA_Ec and NfsA_Bs. Data sets were generated in identical fashion to those described above for the 55 candidate nitroreductase library.

FIG. 17.9 shows the metabolism of compound 64 by members of the 55 candidate nitroreductase over-expression library as measured by GFP SOS assay. The data presented is the fold increase of GFP SOS response (normalised to culture density) exhibited by microplate cultures of E. coli strain SOS-R4 over-expressing candidate nitroreductases when challenged for 6 h with 10 µM of compound 64, compared to an unchallenged control. Data are the average of 2 independent assays and the error bars indicate ±1 standard deviation. The dashed line indicates the baseline activity for the empty plasmid control, and the data sets corresponding to the NfsA and NfsB family members are as marked. Inset: Metabolism of compound 64 was demonstrated for a selection of single and poly mutant variants of NfsA_Ec and NfsA_Bs. Data sets were generated in identical fashion to those described above for the 55 candidate nitroreductase library.

FIG. 17.10 shows purified enzyme kinetic data with compounds 14, 18, 22, 23, 24, 25, 26, 27 and 64 for NfsA_Ec. Reactions contained 10 mM Tris-Cl (pH 7.0), 4% DMSO, 0.20 mM NADPH and varying compound concentrations. Reactions were initiated by addition of enzyme and changes in absorbance were measured for 20 s at 400 nm on a spectrophotometer to monitor NTR-catalysed compound reduction. Non-linear regression analysis and Michaelis-Menten curve fitting was performed using Sigmaplot 10.0 (Systat Software Inc.).

FIG. 17.11 shows UV/Vis spectroscopy measurements of the relative rates of NfsB_Ec catalysed reduction for each test compound at 400 nm. Compounds 14, 18, 22, 23, 24, 25, 26, 27 and 64 (600 µM) were added to NADPH (200 µM) in 10 mM Tris-Cl pH 7.0. Reactions were initiated by enzyme addition (between 0.25 and 5 I g per reaction, determined empirically in pilot experiments). Rates represent µmol of compound reduced per mg enzyme added per minute. Data are the average of at least 4 independent measurements and the error bars indicate ±1 standard deviation.

FIG. 18 shows IC50 (uM) of prodrugs PR-104A and 14, 18, 22, 23, 24, 25, 26, 27, 64 of the present invention, in HCT116 wild type cancer cells versus HCT116 cells engineered to over-express the human two-electron reductase aldo-ketoreductase 1C3 (AKR1C3). All appear less susceptible to AKR1C3-mediated cytotoxicity than PR-104A.

FIG. 18.1 shows IC50 (uM) of prodrugs PR-104A and 22, 23, 24, 25, 26, 27 of the present invention, in H1299 wild type cancer cells versus H1299 cells engineered to over-express the human two-electron reductase aldo-ketoreductase 1C3 (AKR1C3). All appear less susceptible to AKR1C3-mediated cytotoxicity than PR-104A.

FIG. 19.1 shows the calculated lipophilicity of compounds of formula 1f compared to their status with respect to demonstrating AKR1C3-dependent cytotoxicity. Footnotes for figure: $^a$Determined using a trained ACD Labs (version 8) log P calculator. $^b$AKR1C3-dependent metabolism status as determined by assessing clonogenic cell kill of the prodrugs in HCT116 wild type Multicellular Layers (MCLs) versus HCT116 MCLs where the cells are engineered to over-express the human two-electron reductase aldo-ketoreductase 1C3 (AKR1C3).

FIG. 20 shows IC50 (uM) of prodrugs PR-104A and 14, 18, 22, 23, 24, 25, 26, 27, 64 of the present invention, in HCT116 wild type cancer cells versus HCT116 cells engineered to over-express the bacterial two-electron reductase E coli NfsA. All prodrugs produce E coli NfsA-mediated cytotoxicity.

FIG. 20.1 shows IC50 (uM) of prodrugs PR-104A and 14, 18, 22, 23, 24, 25, 26, 27, 64 of the present invention, in H1299 wild type cancer cells versus H1299 cells engineered to over-express the bacterial two-electron reductase E coli NfsA. All prodrugs produce E coli NfsA-mediated cytotoxicity.

FIG. 22.1 shows the median time to four times relative tumour volume (RTV4) and tumour growth delay (TGD) as a percentage of vehicle only treated tumour controls, for 15% E coli NfsA-expressing HCT116 xenografts (containing 85% wild type cells) in NIH-III mice administered a single dose of the prodrugs PR-104, 10, 22 and 60 at doses of 338, 1000, 422 and 1330 umol/kg, respectively.

FIG. 22.2 shows mean tumour volume (mm3) of 15% E coli NfsA-expressing H1299 xenografts (containing 85% wild type cells) in NIH-III mice administered a single dose of the prodrugs 10, 22, 60 and 11 at doses of 750, 422, 1330 and 1330 umol/kg, respectively. All of the prodrugs display significant E coli NfsA mediated anti-tumour efficacy. Mean tumour volume of PR-104 at the human equivalent dose of 225 mg/kg (388 umol/kg) is shown by way of reference.

FIG. 22.3 shows the median time to four times relative tumour volume (RTV4) and tumour growth delay (TGD) as a percentage of vehicle only treated tumour controls, for 15% E coli NfsA-expressing H1299 xenografts (containing 85% wild type cells) in NIH-III mice administered a single dose of the prodrugs PR-104, 10, 22, 60 and 11 at doses of 338, 750, 422, 1330 and 1330 umol/kg, respectively.

FIG. 22.4 shows mean tumour volume (mm3) of 15% E coli NfsA-expressing H1299 xenografts (containing 85% wild type cells) in NIH-III mice administered a dose of the prodrugs 22, 23 and 26 at 500 umol/kg twice daily (ie BID) for a total single daily dose of 1000 umol/kg. All of the prodrugs display significant E coli NfsA mediated anti-tumour efficacy.

FIG. 22.5 shows the median time to four times relative tumour volume (RTV4) and tumour growth delay (TGD) as a percentage of vehicle only treated tumour controls, for 15% E coli NfsA-expressing H1299 xenografts (containing 85% wild type cells) in NIH-III mice administered a single dose of the prodrugs 22, 23 and 26 at a dose of 1000 umol/kg (500 umol/kg BID).

DETAILED DESCRIPTION OF THE INVENTION

Definitions

Figure 1:
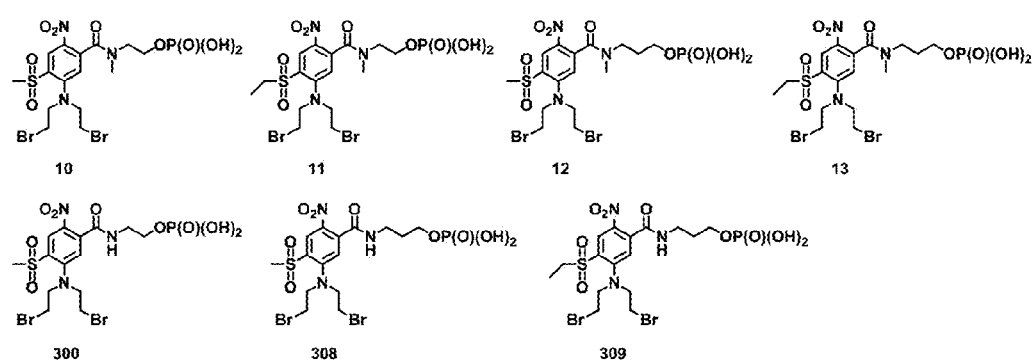
FIG. 1 shows representative phosphates of dibromo mustards of Formula I

PR-104 is a phosphate ester pre-prodrug of the alcohol PR-104A. PR-104 is also called 2-((2-bromoethyl)(2,4-dinitro-6-((2-(phosphonooxy)ethyl)carbamoyl)phenyl)amino) ethyl methanesulfonate.

PR-104A also called 2-((2-bromoethyl)(2-((2-hydroxyethyl)carbamoyl)-4,6-dinitrophenyl)amino)ethyl methanesulfonate "Nitroreductase"—an enzyme that catalyses the reduction of a nitro functional group ($-NO_2$) or quinone functional group. Nitroreductases as referred to herein may be either endogenous or exogenous.

"Prodrug"—An inactive compound that is converted to a reactive cytotoxic metabolite once activated. Preferably activation occurs within nitroreductase expressing target cells within the local tumour microenvironment by reduction of a nitro group. Prodrugs may be activated by reduction by a bacterial nitroreductase independent of tissue oxygen concentration or by reduction by a human nitroreductase in tissues lacking oxygen (hypoxic tissues).

"Activation" or "metabolism" with reference to prodrugs refers to the catalytic reduction process that a prodrug may undergo following contact with an enzyme. The prodrug may be activated/metabolised to yield alternative compounds such as cytotoxic metabolites that may have beneficial activity for therapeutic applications.

"Ablation" is to be considered in its broadest context and as well as meaning the complete ceasing of the function of the target being ablated, is also intended to encompass any degree of suppression of the function of the target where the target includes but is not limited to a cell.

"Cell" refers to a biological sub-unit that is specialized in carrying out a particular function or functions. For the purposes of the invention as defined herein, the term "cell" also encompasses the medium in which the cell is found. For example this may mean a hypoxic region of a tumour or the cell matrix which supports the cell in vivo or in vitro.

"Endogenous"—Naturally occurring, originating or produced within an organism, tissue, or cell.

For example endogenous enzymes in a mammal are enzymes that are naturally present in mammalian cells.

"Exogenous"—Originating or produced outside of an organism, tissue, or cell. For example exogenous enzymes in a mammal are foreign enzymes that do not occur in mammalian cells. For example bacterial enzymes that may have been introduced through genetic manipulations.

"Hypoxic" as referred to herein refers to a concentration of oxygen in tissue that is significantly lower the normal physiological concentration of oxygen in healthy well perfused tissue, in particular oxygen tensions below approximately 1% (10,000 parts per million oxygen; 7.6 mmHg).

"Bystander effect"—this effect is triggered by treatment of a target cell with a cytotoxic prodrug metabolite and refers to the secondary ablation effect on cells or tissues in the local microenvironment to the target cell. Without wishing to be bound by theory, the bystander effect is believed to be caused by the diffusion of cytotoxic prodrug metabolites (activated prodrugs) from the site of production to affect unmodified cells separate from the target cell.

"Treatment" is to be considered in its broadest context. The term does not necessarily imply that a subject is treated until total recovery. Accordingly, "treatment" broadly includes, for example, the prevention, amelioration or management of one or more symptoms of a disorder, the severity of one or more symptoms and preventing or otherwise reducing the risk of developing secondary complications.

"Prevention" of disease should not be taken to imply that disease development is completely prevented, and includes delay of disease development.

"Nitrobenzamide mustards" refers to any compound possessing a benzene ring that is substituted with nitro, carboxamide and aniline mustard functionalities.

"Nitrobenzamide mustard alcohols" refers to any compound possessing a benzene ring that is substituted with nitro, carboxamide and aniline mustard functionalities where the carboxamide substituent further contains an alcohol moiety.

"AKR1C3 enzyme" refers to the human enzyme aldoketo reductase 1C3. The aldo-keto reductases (AKRs) are a superfamily of cytosolic enzymes that are involved in the reduction of aldehydes and ketones to their corresponding primary and secondary alcohols, respectively, from a variety of endogenous and exogenous substrates (Jez et al., 1997). AKRs require the presence of a cofactor NADPH in order to catalyze the reduction of carbonyl groups (Schlegel et al., 1998). The human AKRs are classed into three families—AKR1, AKR6 and AKR7—of which AKR1 is the best characterized in terms of structure and function (Penning and Drury, 2007). The AKR1C subfamily includes AKR1C1-4, with all four enzymes having hydroxysteroid dehydrogenase (HSD) activity (Penning et al., 2000). The genes encoding AKR1C1-4 share more than 86% amino acid sequence identity, and show differences in substrate and regiospecificity of the sites metabolized (Penning and Byrns, 2009). AKR1C3 is the enzyme responsible for the reduction of Prostaglandin D2 (PGD2) in humans.

"Substantially resistant to AKR1C3 enzyme metabolism" as referred to herein refers to a compound that exhibits a very low or substantially zero degree of metabolism by the human AKR1C3 enzyme when compared to a compound that is readily metabolised by human AKR1C3. AKR1C3 metabolism can be demonstrated by incubating test compounds and NADPH co-factor with recombinant AKR1C3 protein and assaying for the loss of NADPH co-factor, where a loss of co-factor indicates enzymatic metabolism of the compounds. Prodrugs of the present invention that are metabolised by AKR1C3 demonstrate increased clonogenic cell kill in multicellular layers of cells engineered to over-express AKR1C3 relative to multicellular layers of wild type isogenic cells, whereas compounds of the present invention that are substantially resistant to AKR1C3 enzyme metabolism demonstrate an inability to provide increased clonogenic cell kill in multicellular layers of cells engineered to over-express AKR1C3 relative to multicellular layers of wild type isogenic cells.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
acid addition salts formed with inorganic acids such as hydrochloric acid, hydrobromic acid, sulfuric acid, nitric acid, phosphoric acid and the like; or formed with organic acids such as acetic acid, methanesulfonic acid, maleic acid, tartaric acid, citric acid and the like; or salts formed when an acidic proton present in the parent compound either is replaced by a metal ion, e.g. an alkali metal ion, an alkaline earth ion, or an aluminium ion; or coordinates with an organic or inorganic base. Acceptable organic bases include ethanolamine, diethanolamine, N-methylglucamine, triethanolamine and the like. Acceptable inorganic bases include aluminium hydroxide, calcium hydroxide, potassium hydroxide, sodium carbonate and sodium hydroxide.

"Necrosis" as referred to herein is an area of dead cells. These are commonly found in tumours due to cellular injury and premature cell death caused by factors external to the cell or tissue, such as trauma from inadequate supply of nutrients and oxygen.

The terms "administered", "administration" and the like when used in reference to the administration of a compound to a target cell are intended to encompass all methods of introduction and are not intended to be limited to direct administration to the site of a tumour cell. The terms are intended to encompass indirect methods of introducing the compound to the target cell for example using GDEPT, VDEPT, CDEPT or ADEPT.

The phrase "therapeutically effective amount" is intended to mean an amount of a compound that has the potential to elicit a therapeutic effect. In the case of a prodrug, it will be understood by a skilled person that this will only actually elicit a therapeutic effect after activation/metabolism of that prodrug.

"Therapeutically proximate" as referred to herein in relation to a bystander effect means a cell that is sufficiently close to a target cell capable of metabolising/activating a prodrug that the cell receives therapeutically effective concentrations of active/cytotoxic prodrug metabolites. Without wishing to be bound by theory this is typically within 1 to 10 cell diameters of the target cell.

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The present invention broadly relates to a new class of compounds that have particular use as agents or drugs for cancer therapy and related methods. In particular, the invention provides a specific class of nitrobenzamide mustards, nitrobenzamide mustard alcohols and their corresponding phosphate esters, for use as targeted cytotoxic agents or bioreductive prodrugs.

The prior art suggests that elimination of AKR1C3 activation can be achieved in a related class of dinitrobenzamide mustard prodrugs (Patterson et al, WO/2010/044685A1). The homologous N-alkylcarboxamide series 5 to 9 (Scheme 3) was studied in isogenic HCT116 cell lines comparing cytotoxicity of the compounds in either wild-type or AKR1C3 over-expressing cells in a conventional two dimension, low cell density IC50 assay. Data indicated that the incremental N-alkyl extension (H to methyl to ethyl to isopropyl to propyl) diminished AKR1C3 dependent cell sensitivity under aerobic conditions. It was therefore concluded that prodrugs 8 and 9 were not substrates for AKR1C3.

Scheme 3

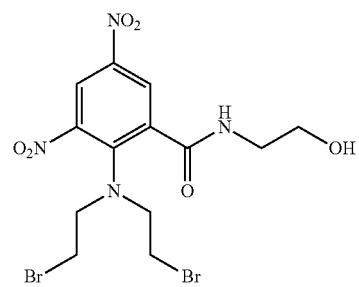

5

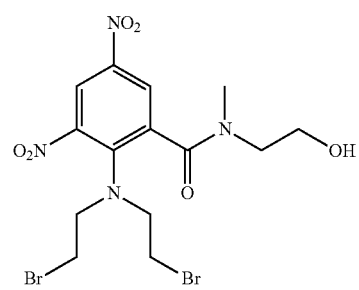

6

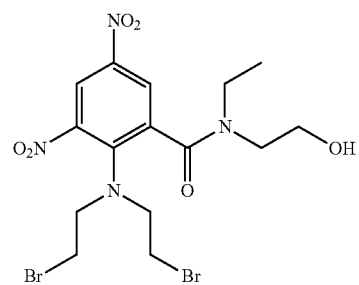

7

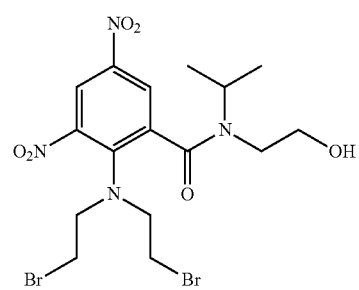

8

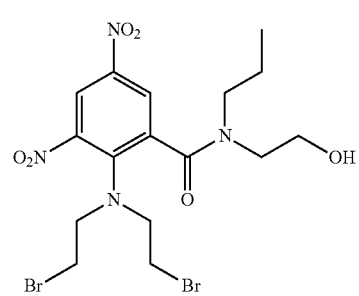

9

Figure 15:
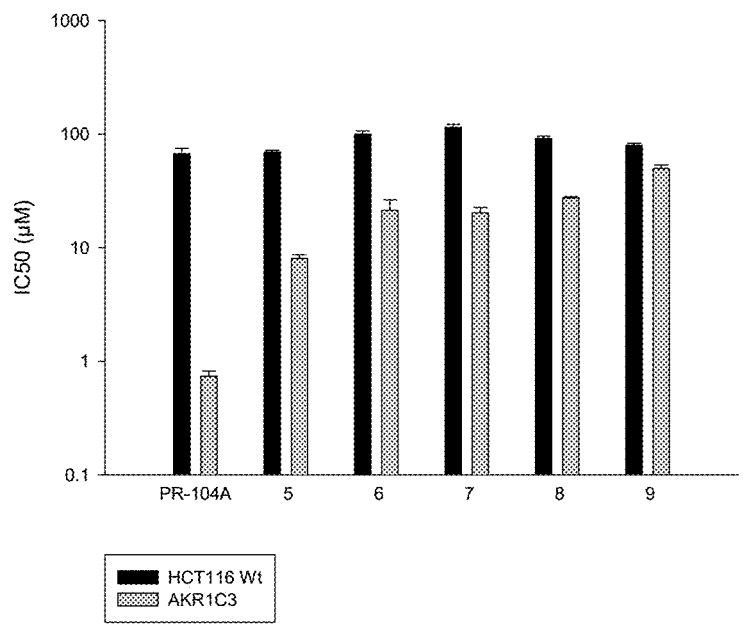
FIG. 15 shows a comparison of IC50 (uM) of prodrugs of the prior art (PR-104A, 5 to 9) in HCT116 wild type cancer cells versus HCT116 cells engineered to over-express the human two-electron reductase aldo-ketoreductase 1C3 (AKR1C3). Progressing across the series from 5 to 9 is consistent with a relative loss of AKR1C3 metabolism induced cytotoxicity compared to PR-104 in this low cell density assay, such that prodrug 9 appears to be AKR1C3-negative.
Figure 16:
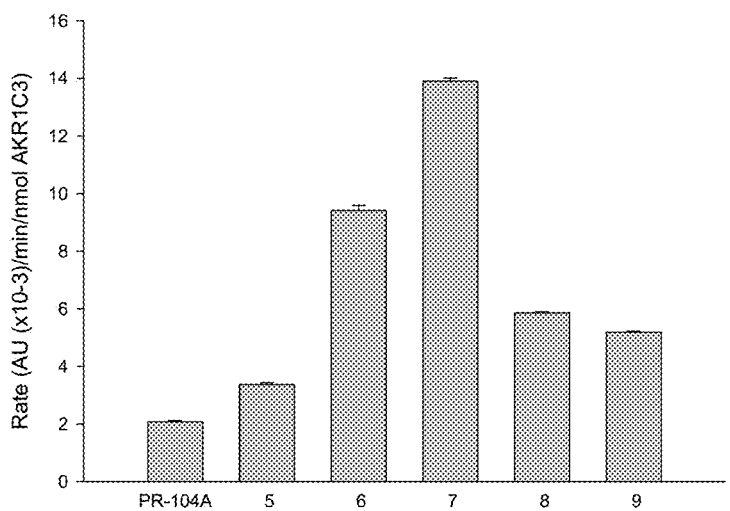
FIG. 16 shows a recombinant AKR1C3 metabolism assay for rate of loss of NADPH co-factor. All of the prodrugs 5 to 9 are better substrates for AKR1C3 than PR-104A.

However, the inventors have recently determined that low cell density IC50 assays can produce 'false negatives'. As the prodrug series 5 to 9 becomes increasingly more lipophilic the inventors have found that AKR1C3-formed metabolite is lost from the cell of production into the essentially infinite dilution of the cell culture media of the IC50 assay. This loss protects the cell from cytotoxic insult such that the most lipophilic compounds 8 and 9 appear negative for AKR1C3 dependent cell sensitivity (FIG. 15). Hence, the inventors have determined through recombinant AKR1C3 metabolism studies that the entire series 5 to 9 is readily metabolised by AKR1C3 (FIG. 16).

The inventors have shown that growing AKR1C3 positive cells in a three dimensional layer and then exposing this multicellular layer (MCL) to prodrugs 5 to 9 results in extensive clonogenic cell killing compared to the AKR1C3 negative control MCL experiments (FIG. 17). Here metabolite produced in one cell is lost to the neighbouring cell, exacting its cytotoxicity there. The inventors have therefore found that this high cell density MCL screen provides a method to detect 'false negatives' from a two dimensional in vitro IC50 screen and demonstrated that it can be used in the design of bona fide AKR1C3-negative prodrugs, such as those of the present invention.

Therefore the disclosure of WO/2010/044685A1 is not indicative that any form of nitrobenzamide mustard, nitrobenzamide mustard alcohol or their corresponding phosphate ester would be resistant to metabolism by the enzyme AKR1C3. It was therefore surprising that the class of prodrugs that are the subject of the present invention exhibited such resistance to metabolism by AKR1C3.

Figure 19:
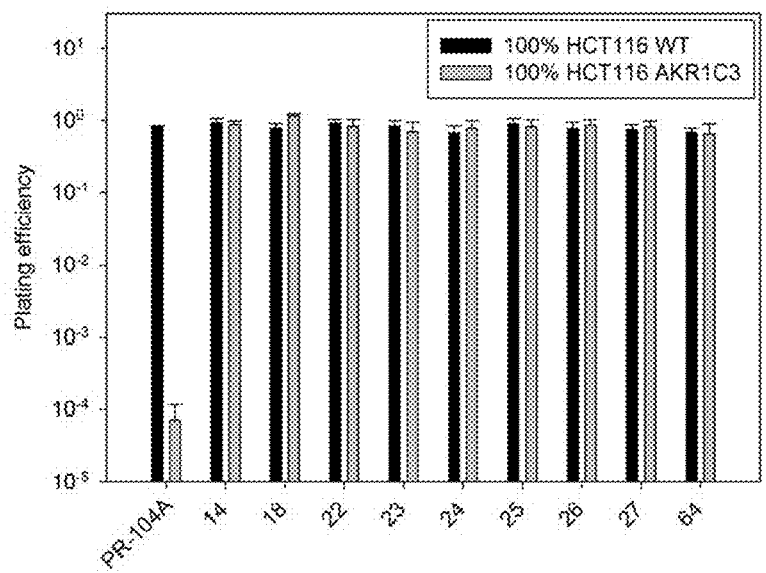
FIG. 19 shows clonogenic cell kill of PR-104A compared to prodrugs 14, 18, 22, 23, 24, 25, 26, 27, 64 of the present invention in HCT116 wild type Multicellular Layers (MCLs) versus HCT116 MCLs where the cells are engineered to over-express the human two-electron reductase aldo-ketoreductase 1C3 (AKR1C3). Prodrugs 14, 18, 22, 23, 24, 25, 26, 27 and 64 do not cause AKR1C3-dependant cytotoxicity.

The inventors have identified compounds that show reduced or zero metabolism by the human enzyme AKR1C3 when compared to known compounds (FIGS. 18 and 19). The novel compounds have the advantage that they are selectively metabolised by hypoxic tumour regions or exogenous nitroreductase expressing cells rather than being metabolised by human AKR1C3 naturally present in other tissues such as bone marrow. This selectivity may be desirable to reduce side effects of the compound when administered to a patient. The selectivity may also reduce the therapeutically effective dose required which has advantages including reduced cost and potential side effects.

Previously known compounds have had to be administered in either neat DMSO or DMSO/polyethylene glycol/water (Atwell et al., J. Med. Chem., 2007, 50, 1197-1212) which results in large variations in maximum tolerated dose. An advantage of the compounds of the present invention is their solubility in water. This has advantages for dissolution of the compound for effective preparation of a composition of the invention and enables pharmacokinetic calculations regarding dosage and other parameters to be measured more accurately. The increased solubility also provides for more effective administration and assists with efficient transport of the prodrug to the site of activation within the body.

In a particular embodiment, the solubility of the compound of the first or second aspect is greater than about 95 mM when determined in Phosphate Buffered Saline (PBS) containing 2 equivalents of sodium bicarbonate or greater than 10 mM when determined in Lactate Buffer at pH=4. The solubility of compounds 10, 11, 23 and 300 (FIG. 14) which are representative of the novel class as a whole, compares to a solubility of compound 4 of 0.068 (when determined in α-Minimal Essential Media (α-MEM) containing 5% Fetal Calf Serum (FCS)). A solubility of greater than 10 mM is sufficiently soluble for a drug to be useful in this context. Therefore the compounds of the present invention exhibit surprisingly appropriate solubility characteristics for use as prodrugs.

A further embodiment of the invention that is enabled by the surprisingly high solubility of compounds of the invention is a soluble composition comprising a compound of the invention. Such compositions are of use in cell ablation or for the treatment of cancer and other hyperproliferative conditions.

Compounds of the present invention comprise the nitrobenzamide mustards, nitrobenzamide mustard alcohols and their corresponding phosphate esters. The nitrobenzamide mustards are relatively inactive in their nitro form, however on reduction are converted into a range of active (cytotoxic) compounds which can be utilised for cell ablation, for example ablation of tumour cells.

In a particular embodiment the invention provides a method of cell ablation comprising the use of a compound of the invention. In a particular embodiment, the compound is a prodrug capable of activation by contact with a) at least one nitroreductase enzyme, and/or b) a low oxygen (hypoxic) environment.

The inventors have also demonstrated effective methods for selecting a compound which is substantially resistant to AKR1C3 enzyme metabolism (as defined above) and use of that compound in a method of cell ablation. Specifically, FIG. 16 shows compounds of the prior art that are metabolized by AKR1C3, FIG. 17 shows how these AKR1C3 metabolised compounds give increased clonogenic cell kill in MCLs that over-express AKR1C3 compared to the wild type cells and FIG. 19 shows compounds of the present invention that must be resistant to AKR1C3 metabolism because of their inability to provide increased clonogenic cell kill in multicellular layers of cells engineered to over-express AKR1C3 relative to multicellular layers of wild type isogenic cells.

In a further embodiment, the compound of the invention or a mixture thereof is administered to a subject in an effective amount to ablate a cell wherein said cell expresses at least one nitroreductase enzyme.

The compounds of the invention are able to penetrate tumour tissue and be selectively reduced to an active (cytotoxic) form by contact with a nitroreductase enzyme (FIGS. 20-22) or by contact with a hypoxic environment such as that found in a tumour. This active form is able to ablate the target cells and therefore has particular utility in the treatment of cancer and other hyperproliferative disorders. In a particular embodiment, the nitroreductase enzyme is encoded for by the nfsB and/or the nfsA gene of either E. coli or by orthologous genes in other bacterial species. In an alternative embodiment, the nitroreductase is encoded by a mutant nitroreductase. The invention provides a compound that may be administered to a subject in combination with a therapy that results in expression of an exogenous nitroreductase enzyme within, or therapeutically proximate to, a tumour.

Figure 23:
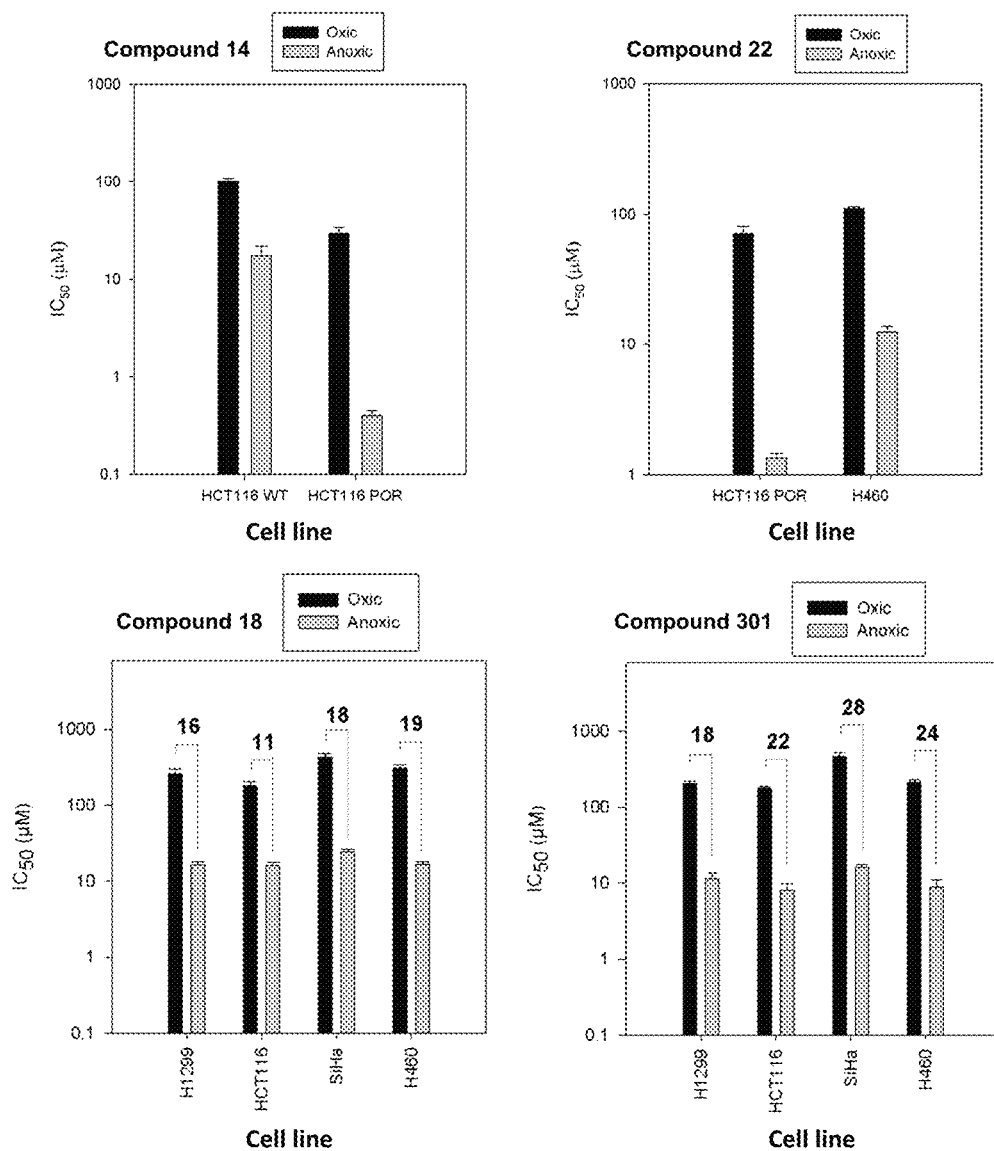
FIG. 23 shows oxic and anoxic IC50 (uM) of prodrugs 14, 22, 18 and 301 in the HCT116, H460, H1299 and SiHa wild type cancer cell lines and the HCT116 POR cell line, an HCT116 cell line that has been engineered to over-express the human one-electron reductase Cytochrome P450 reductase. In each example exposure of the cells to anoxia leads to selective metabolism of the prodrugs producing metabolites of increased cytotoxicity, resulting in Hypoxic Cytotoxicity Ratios (HCR) ranging from 11 to 28-fold for compounds 18 and 301 in the wild type cancer cell lines. Larger HCRs were observed for compounds 14 and 22 in the HCT116 POR cell line indicating increased prodrug metabolism and therefore cytotoxicity in cells over-expressing this human one-electron reductase.
Figure 24:
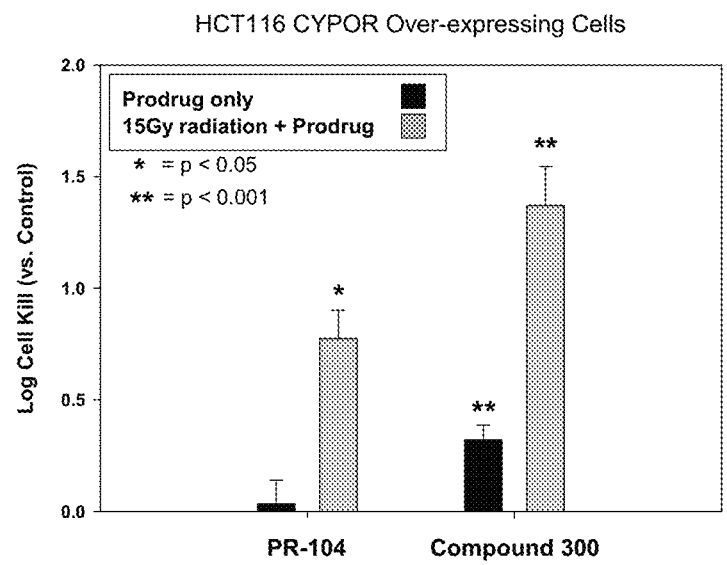
FIG. 24 shows calculated log cell kill (LCK) for 'prodrug only' or '15Gy radiation+prodrug' in HCT116 tumour xenografts engineered to over-express the human one-electron reductase Cytochrome P450 reductase. PR-104 (345 μmol/kg) and prodrug 300 (1330 μmol/kg) in mice receiving no radiation (black bars) or in mice which have received 15Gy radiation (grey bars). Prodrug 300 displays significant hypoxic cell kill in vivo.
Figure 25:
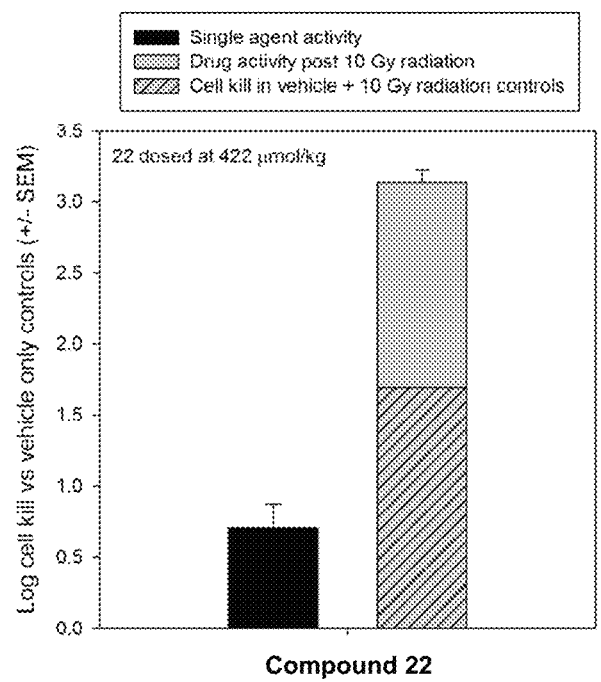
FIG. 25 shows calculated log cell kill (LCK) versus vehicle only controls for 'prodrug only' (single agent activity) or '10Gy radiation+prodrug' in wild type SiHa tumour xenografts grown subcutaneously in NIH-III nude mic. Mice were administered compound 22 at 422 umol/kg. LCK of compound 22 in mice receiving no radiation (black bars) or in mice which have received both compound 22 (422 umol/kg) and 10Gy radiation (light grey bars). LCK of radiation alone (mice receive vehicle only and not compound 22) is shown in light grey bars with black stripes. Prodrug 22 displays significant hypoxic cell kill in vivo as determined by clonogenic cell kill of tumour cells that are not sterilised by 10Gy of radiation.

In the presence of pathological hypoxia found in human solid tumours, net reduction to hydroxylamine and amine cytotoxic metabolites is able to occur providing tumour-selective cell ablation. In addition to metabolism by nitroreductase enzymes, the compounds of the present invention are also metabolised in hypoxic regions that may be found in tumour regions (FIGS. 23-25). Thus in a further particular embodiment the invention provides a method of cell ablation including the step of administering a compound of the invention or a mixture thereof in an effective amount to ablate a cell wherein said cell is found in, or therapeutically proximate to, a hypoxic region.

The invention therefore provides a method of treatment of cancer or a hyperproliferative condition wherein a compound of the invention or a mixture thereof is administered in a therapeutically effective amount to a tumour cell, or therapeutically proximate to a tumour cell, in a subject.

Such compounds of the invention also have utility for the preparation of a composition for the ablation of a cell, or for the treatment of cancer or a hyperproliferative condition. In a particular embodiment, the compound is a prodrug capable of activation by contact with a) at least one nitroreductase enzyme, and/or b) a low oxygen (hypoxic) environment.

Figure 26:
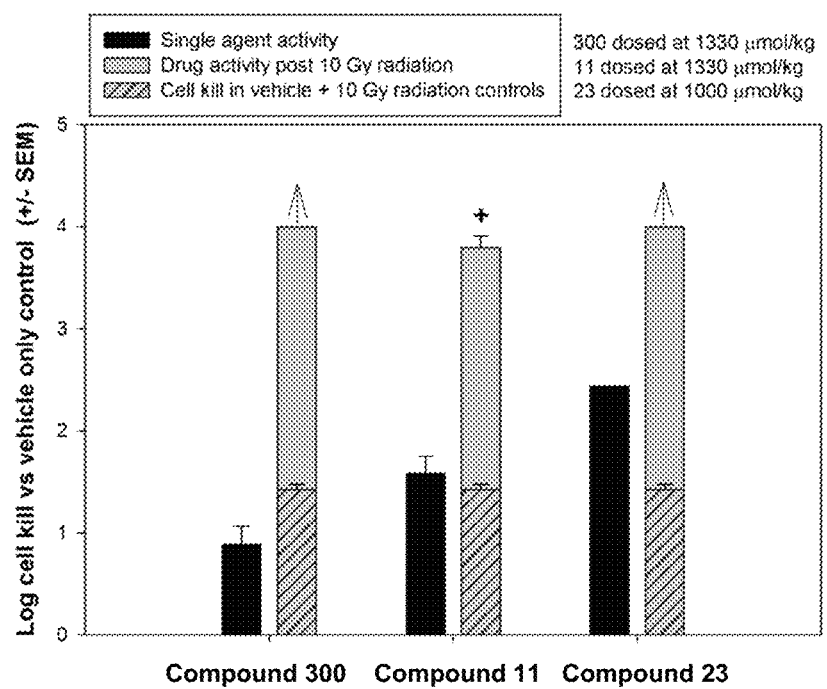
FIG. 26 shows calculated log cell kill (LCK) versus vehicle only controls for 'prodrug only' (single agent activity) or '10Gy radiation+prodrug' in wild type SiHa tumour xenografts grown subcutaneously in NIH-III nude mice. Mice were administered compound 300, 11 and 23 at 1330, 1330 and 1000 umol/kg, respectively. LCK of test compounds in mice receiving no radiation (black bars) or in mice which have received both test compounds and 10Gy radiation (light grey bars). LCK of radiation alone (mice receive vehicle only and not test compounds) is shown in light grey bars with black stripes. Prodrugs 300, 11 and 23 display significant hypoxic cell kill in vivo as determined by clonogenic cell kill of tumour cells that are not sterilised by 10Gy of radiation. LCK for 'prodrug plus radiation' was >4 (ie off-scale in this assay) for 4/4 mice treated with compounds 300 and 23 (denoted by an upward point arrow). LCK for 'prodrug plus radiation' was >4 (ie off-scale in this assay) for ¼ mice treated with compound 11 (denoted by +).

The inventors have also surprisingly found that a compound of the present invention, when administered to a cell in conjunction with radiation treatment is especially effective in ablating the cell (FIG. 26). Accordingly, it is envisaged that the invention provides a method of cancer treatment incorporating the administration of a prodrug of the invention and irradiation of the tumour cells. The irradiation step may be carried out before, concurrently with or after the administration of the prodrug compound.

Once metabolised, the active form of the prodrug, a cytotoxic metabolite, is then capable of ablation of nitroreductase naive cells by way of a bystander effect. This ability to ablate cells by way of a bystander effect is determined in a three dimensional cell culture model. This ability has particular use for the ablation of cells surrounding nitroreductase-expressing cells in a tumour.

The inventors have previously cloned and assembled a phylogenetically diverse library of 55 nitroreductase candidates from 20 bacterial species, representing 12 different enzyme families. These bacterial nitroreductase enzymes have been screened for their ability to co-metabolise nitroimidazole imaging probes (bio-imaging) and bioreductive prodrugs (bio-therapy, bio-control) and the NfsA and NfsB families have been identified as being of particular interest. The nitroreductase enzyme may be a nitroreductase described in WO/2012/008860, which includes mutant nitroreductases and functionally equivalent variants of the nitroreductases described therein.

The inventors have also developed novel screening methodologies to quantify the activity of a candidate nitroreductase with a target prodrug. Further details of the screening methods used and results of the NTR screening of the prodrugs in bacteria and the NfsA kinetics and NfsB rate of metabolism assays are provided in Example 3 and FIGS. 17.1 to 17.11. Results show that the compounds tested are effectively metabolised by bacterial nitroreductases from a number of different species and enzyme families. Therefore the compounds of the invention have broad-spectrum affinity to, and are substrates for, multiple bacterial nitroreductases with potential for therapeutic utility while retaining resistance to metabolism by the endogenous human reductase AKR1C3. The compounds selected for screening are representative of the other compound groups encompassed by the invention and similar results would be expected.

The compounds of the present invention are broadly defined by Formula (I) or Formula (II), where Formula (I) is:

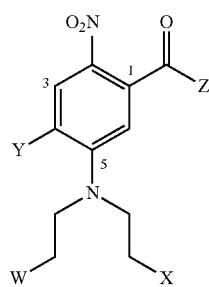
(I)

wherein W represents Cl, Br, I, OSO$_2$R,
X represents Cl, Br, I, OSO$_2$R,
Y represents H, CN, SO$_2$R,
each R independently represents a lower C$_{1-6}$ alkyl group, Z is selected from any of the radicals of Formula (Ia)

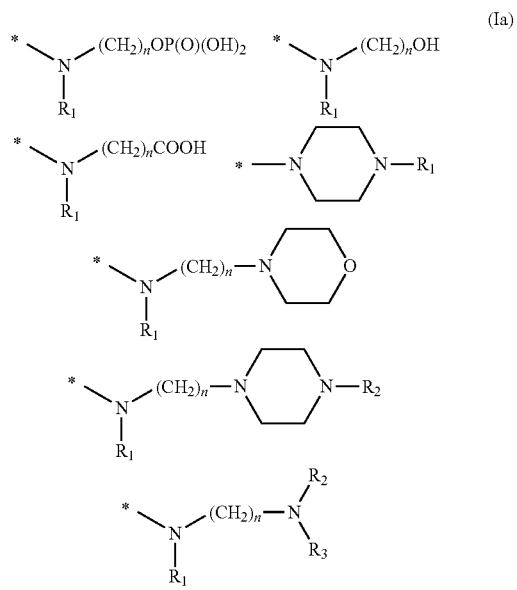
(Ia)

Where
R$_1$ represents H, or a lower C$_{1-6}$ alkyl group,
R2 and R3 may independently represent H, or a lower C1-6 alkyl group; or,
R2 and R3 together may be linked to form a substituted or unsubstituted heterocyclic ring comprising 5 or 6 members,
n represents 2 to 6
* represents a point of attachment to Formula I
or a pharmaceutically acceptable salt thereof;
and where Formula (II) is:

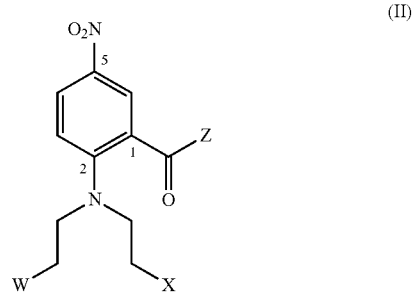
(II)

wherein W represents Cl, Br, I, OSO$_2$R,
X represents Cl, Br, I, OSO$_2$R,
each R independently represents a lower C$_{1-6}$ alkyl group,
Z is selected from any of the radicals of Formula (IIa)

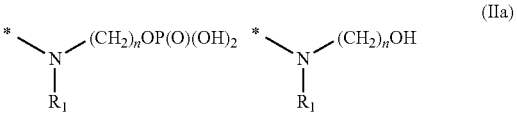
(IIa)

where
R$_1$ represents H, or a lower C$_{1-6}$ alkyl group,
n represents 2 to 6
* represents a point of attachment to Formula II
or a pharmaceutically acceptable salt thereof.

The compounds of Formula (I) and (II) can be used in for treating or preventing cancer or hyperproliferative conditions. Methods of treatment as previously described comprise the step of administering a compound of Formula I or II, or pharmaceutically acceptable salts thereof, or a mixture thereof to a subject in need thereof. Further, there is provided the use of a compound of Formula I or II or a mixture thereof in the manufacture of a composition for the treatment of cancer or hyperproliferative conditions.

In another embodiment there is provided a method of cell ablation including the step of administering a compound of Formula I or II, or pharmaceutically acceptable salts thereof, or a mixture thereof in an effective amount to ablate cells wherein said cells express at least one nitroreductase enzyme or are in a hypoxic environment.

In a further embodiment of the invention there is provided a method of cancer treatment wherein a compound of the invention or a mixture thereof is administered in a therapeutically effective amount to a tumour cell in a subject.

Preferably the cells that express the at least one nitroreductase enzyme are tumour cells in tissue in a subject.

Preferably the cells are mammalian cells.

In another embodiment there is provided a method of cancer treatment wherein a compound of Formula I or II, or pharmaceutically acceptable salts thereof, is administered in a therapeutically effective amount to tumour cells in a subject.

Preferably the therapeutically effective amount administered is between about 20% to 100% of the maximum tolerated dose of said subject.

Preferably the compound of Formula I or II, or pharmaceutically acceptable salts thereof, is administered for use in cell ablation in conjunction with at least one nitroreductase enzyme.

Preferably the compound of Formula I or II, or pharmaceutically acceptable salts thereof, or mixture thereof is administered in conjunction with GDEPT (gene-directed enzyme prodrug therapy), VDEPT (virus-directed enzyme prodrug therapy), CDEPT (clostridia-directed enzyme prodrug therapy) or ADEPT (antibody-directed enzyme prodrug therapy).

Preferably the at least one nitroreductase enzyme is encoded for by the nfsA gene or the nfsB gene of *E. coli* or by orthologous genes in other bacterial species.

Preferably the method of cancer treatment further included the step of administering one or more chemotherapeutic agent and/or therapies to the subject before, during or after the administration of the compounds of Formula I or II or mixture thereof.

While these compounds will typically be used in cancer prevention or cancer therapy of human subjects, they can be used to target cancer cells in other warm blooded animal subjects, such as other primates, farm animals such as cattle, and sports animals and pets such as horses, dogs and cats.

In another embodiment there is provided a pharmaceutical composition including a therapeutically effective amount of a compound of Formula (I) or Formula (II) or pharmaceutically acceptable salts thereof, or a mixture thereof, and a pharmaceutically acceptable excipient, adjuvant, carrier, buffer or stabiliser.

In one embodiment the composition will be in the form of a tablet, capsule, powder, or liquid. The composition may be formulated for administration parenterally, preferably by intravenous infusion.

In a particular embodiment, the composition is soluble in aqueous solution. Preferably, the solubility of the compound of the first or second aspect as found in the composition is greater than 95 mM when determined in Phosphate Buffered Saline (PBS) containing 2 equivalents of sodium bicarbonate or greater than 10 mM when determined in Lactate Buffer at pH=4.

The concentration of the prodrug will depend on the nature of the prodrug used and the amount required to achieve a therapeutic effect once activated by the nitroreductase/hypoxic environment. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like, and the treatment required. In certain embodiments, the composition comprises at least one compound of the invention in the form of pharmaceutically acceptable salts thereof, a hydrate thereof, or a solvate of any of the foregoing. Salts of the amines of the invention may include chloride, bromide, methansulfonate, tosylate, malate salts. Salts of the acids of the invention may include sodium, calcium, potassium acids wherein the acids comprise phosphate acids and carboxylic acids.

The composition of use can include a pharmaceutically acceptable diluent, carrier, buffer, stabiliser, excipient and/or adjuvant of any of the foregoing. The choice of diluent, carrier, buffer, stabiliser excipient and/or adjuvant can depend upon, among other factors, the desired mode of administration. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The compositions can additionally include lubricating agents such as talc, magnesium stearate, and mineral oil, wetting agents, emulsifying and suspending agents, preserving agents such as methyl- and propylhydroxy-benzoates, sweetening agents, pH adjusting and buffering agents, toxicity adjusting agents, flavoring agents, and the like. The compositions can be formulated so as to provide quick, sustained or delayed release of the active ingredient after administration to the patient by employing procedures known in the art. A composition can be formulated in unit dosage form, each dosage comprising a physically discrete unit suitable as a unitary dosage for humans and other mammals, each unit containing a predetermined quantity of active material calculated to produce the desired therapeutic effect, in association with a suitable pharmaceutical excipient, diluent, carrier and/or adjuvant.

Bystander effects can be quantified according to methods described in Wilson et al, 2002, *Cancer Res.* 62:1425-1432, by employing a 3D multicellular layer (MCL) composed of a minority (1%) of NTR-expressing 'activator' cells, mixed with a majority (99%) of parental (wild-type) 'target' cells. The prodrug concentrations for 10% survival ($C_{10}$) of target cells (wild-type cells) grown without activators (T), and targets in co-culture (Tc) and activators (NTR-expressing cells) in co-culture ($A_C$) can be determined. The bystander effect of a test prodrug is measured by the bystander effect efficiency which can be calculated using the algorithm ((Log $C_{10}$T−Log $C_{10}$Tc)/(Log $C_{10}$T−Log $C_{10}$Ac)). A BEE value of less than about 15%, less than about 10%, less than about 5%, less than about 1% or zero is considered "substantially minimal", whilst a BEE value of greater than about 50%, about 60%, about 70% is considered "substantial".

EXAMPLES

Example 1

Materials and Methods for Compound Synthesis

A series of nitrophenyl mustard prodrugs were synthesised and characterised by HPLC, MS, NMR and elemental analysis.

Figure 8:
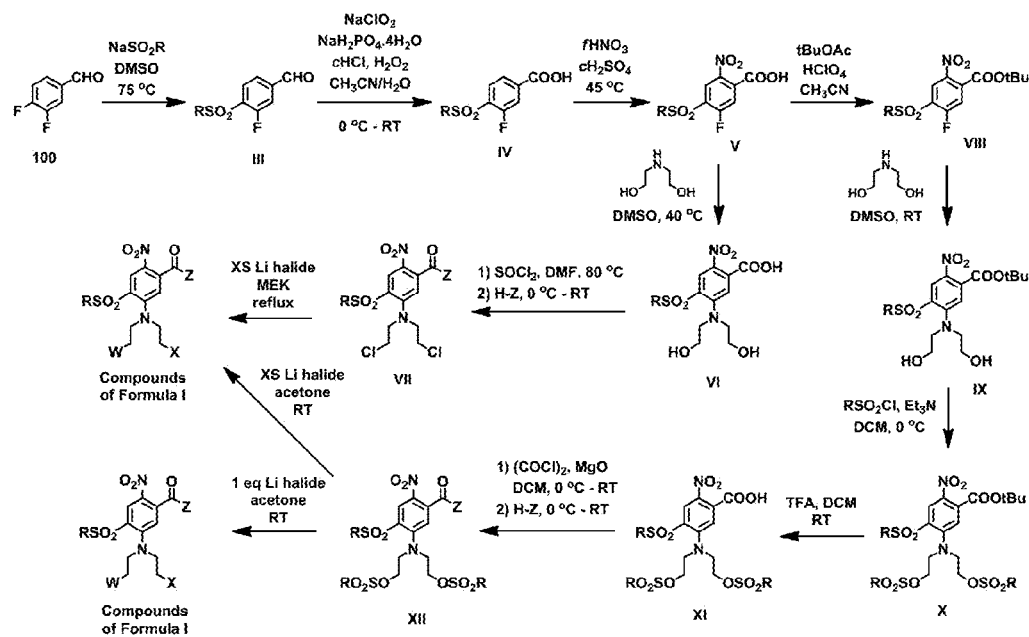
FIG. 8 shows a general synthetic scheme for the synthesis of 4-alkylsulfone prodrugs of Formula I.

A general synthetic scheme for the synthesis of 4-alkylsulfone prodrugs of Formula I is shown in FIG. 8. As will be understood by one skilled in the art, reaction of 3,4-difluorobenzaldehyde (100) with sodium alkanesulfinates provides the alkylsulfones (Ill) which can be oxidised with sodium chlorite in phosphate buffer containing hydrogen peroxide to give the acids (IV). Nitration of these provides the nitroacids (V), which can be reacted directly with diethanolamine to give diols (VI), or first protected to give the tert-butyl esters (VIII), which are subsequently reacted with diethanolamine to give diols (IX). Thionyl chloride mediated chlorination of diols (VI) and subsequent reaction of the resulting acid chloride intermediates with aliphatic amines provides 1-carboxamide dichloro mustards (VII) which can undergo lithium halide mediated halogen exchange in methyl ethyl ketone at reflux to afford compounds of formula I. Alternately diols (IX) can be converted to their bis-alkanesulfonate esters (X) by reaction with the appropriate alkylsulfonyl chlorides. Tert-butyl ester deprotection of the bis-alkanesulfonate esters (X) with trifluoroacetic acid affords the acids (XI). Reaction of these with oxalyl chloride in the presence of magnesium oxide provides the acid chloride intermediates which can be further reacted with aliphatic amines to give the bis-alkanesulfonate 1-carboxamide derivatives (XII). These can be reacted with excess lithium halide at room temperature in acetone to afford symmetrical mustards of formula I, while reaction with 1 equivalent of lithium halide at room temperature in acetone provides unsymmetrical halo alkanesulfonate mustards of formula I.

A preferred general synthetic scheme for the synthesis of 4-alkylsulfone prodrugs bearing a 1-position tertiary carboxamide of Formula I is shown in FIG. 9.1. As will be understood by one skilled in the art, nitroacids (V) can be converted to the acid chlorides (XIX) by reaction with oxalyl chloride. Reaction of these with secondary aliphatic amines then provides the tertiary amides (XX) which can be reacted with diethanolamine to give the diols (XXI). Diols (XXI) can then be converted to their bis-alkanesulfonate esters (XII) by reaction with the appropriate alkylsulfonyl chlorides. These can be reacted with excess lithium halide at room temperature in acetone to afford symmetrical mustards of formula I, while reaction with 1 equivalent of lithium halide at room temperature in acetone provides unsymmetrical halo alkanesulfonate mustards of formula I.

A general synthetic scheme for the synthesis of 4-alkylsulfone prodrugs bearing acid sidechains of Formula I is shown in FIG. 9.1.1. As will be understood by one skilled in the art, thionyl chloride mediated chlorination of diols (VI) and subsequent reaction of the resulting acid chloride intermediates with aliphatic amines bearing a tert-butyl ester protected acid sidechain, provides the 1-carboxamide dichloro mustards (XXII). Lithium halide mediated halogen exchange in methyl ethyl ketone at reflux, followed by trifluoroacetic acid mediated ester deprotection, then provides acid sidechain bearing symmetrical mustard compounds of formula I. Alternately, reaction of the acids (XI) with oxalyl chloride in the presence of magnesium oxide provides the acid chlorides which can then be reacted with aliphatic amines bearing a tert-butyl ester protected acid sidechain to provide the 1-carboxamide bis-alkanesulfonate mustards (XXIII). Reaction of these with excess lithium halide at room temperature in acetone, followed by trifluoroacetic acid mediated ester deprotection then provides acid sidechain bearing compounds with symmetrical mustards of formula I. Reaction of the 1-carboxamide bis-alkanesulfonate mustards (XXIII) with 1 equivalent of lithium halide at room temperature in acetone, followed by trifluoroacetic acid mediated ester deprotection, then provides acid sidechain bearing unsymmetrical halo alkanesulfonate mustards of formula I.

A general synthetic scheme for synthesis of 4-cyano prodrugs of Formula I is shown in FIG. 9.1.2. As will be understood by one skilled in the art, reaction of 3,4-difluorobenzaldehyde (100) with sodium cyanide provides 3-fluoro-4-cyanobenzaldehyde (371) which can be oxidised with sodium chlorite in phosphate buffer containing hydrogen peroxide to give the 3-fluoro-4-cyanobenzoic acid (372). Nitration and subsequent trifluoroacetic anhydride mediated dehydration of the resultant carboxamide and aqueous basic work-up provides acid (373) which is protected as the tert-butyl ester (374). Reaction with diethanolamine gives diol (375), which can be converted to the bis-alkanesulfonate esters (XXIV) by reaction with the appropriate alkylsulfonyl chlorides. Tert-butyl ester deprotection of the bis-alkanesulfonate esters (XXIV) with trifluoroacetic acid affords the acids (XXV). Reaction of these with oxalyl chloride in the presence of magnesium oxide provides the acid chloride intermediates which can be further reacted with aliphatic amines to give the bis-alkanesulfonate 1-carboxamide derivatives (XXVI). These can be reacted with excess lithium halide at room temperature in acetone to afford symmetrical mustards of formula I, while reaction with 1 equivalent of lithium halide at room temperature in acetone provides unsymmetrical halo alkanesulfonate mustards of formula I.

A preferred general synthetic scheme for the synthesis of 4-cyano prodrugs bearing a 1-position tertiary carboxamide of Formula I is shown in FIG. 9.1.3. As will be understood by one skilled in the art, acid (373) can be converted to the acid chloride (376) by reaction with oxalyl chloride. Reaction of this with secondary aliphatic amines then provides the tertiary amides (XXVII) which can be reacted with diethanolamine to give the diols (XXVIII). Diols (XXVIII) can then be converted to their bis-alkanesulfonate esters (XXVI) by reaction with the appropriate alkylsulfonyl chlorides. These can be reacted with excess lithium halide at room temperature in acetone to afford symmetrical mustards of formula I, while reaction with 1 equivalent of lithium halide at room temperature in acetone provides unsymmetrical halo alkanesulfonate mustards of formula I.

A general synthetic scheme for the synthesis of 4-cyano prodrugs bearing acid sidechains of Formula I is shown in FIG. 9.1.4. As will be understood by one skilled in the art, reaction of the acids (XXV) with oxalyl chloride in the presence of magnesium oxide, provides the acid chlorides which can then be reacted with aliphatic amines bearing a tert-butyl ester protected acid sidechain to provide the 1-carboxamide bis-alkanesulfonate mustards (XXIX). Reaction of these with excess lithium halide at room temperature in acetone, followed by trifluoroacetic acid mediated ester deprotection then provides acid sidechain bearing compounds with symmetrical mustards of formula I. Reaction of the 1-carboxamide bis-alkanesulfonate mustards (XXIX) with 1 equivalent of lithium halide at room temperature in acetone, followed by trifluoroacetic acid mediated ester deprotection, then provides acid sidechain bearing unsymmetrical halo alkanesulfonate mustards of formula I.

Figure 12:
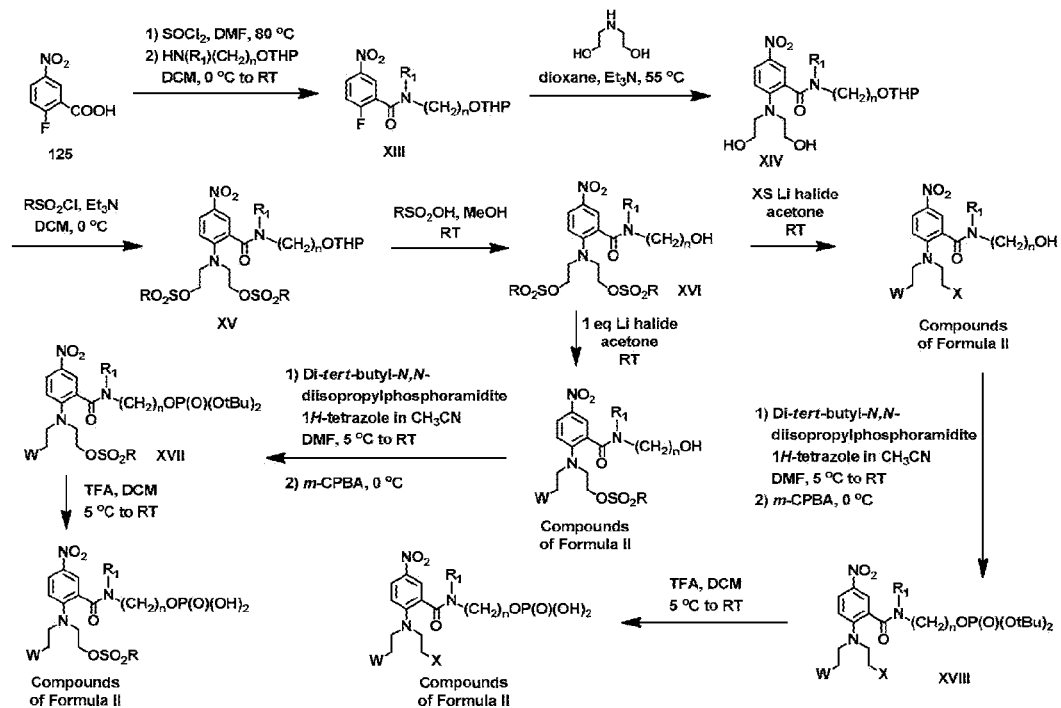
FIG. 12 shows a general scheme for synthesis of prodrugs of Formula II

A general scheme for synthesis of prodrugs of Formula II is shown in FIG. 12. As will be understood by one skilled in the art, reaction of 2-fluoro-5-nitrobenzoic acid (125) with thionyl chloride and subsequent reaction of the resulting acid chloride with aliphatic amines bearing THP protected alcohols provides carboxamides (XIII). Reaction with diethanolamine then gives diols (XIV), which can be converted to their bis-alkanesulfonate esters (XV) by reaction with the appropriate alkylsulfonyl chlorides. THP acetal deprotection of the bis-alkanesulfonate esters (XV) with the appropriate alkylsulfonic acid affords the alcohols (XVI). These can be directly reacted with excess lithium halide at room temperature in acetone to afford symmetrical mustard alcohols of formula II, while reaction with 1 equivalent of lithium halide at room temperature in acetone provides unsymmetrical halo alkanesulfonate mustard alcohols of formula II. These alcohols of formula II can then be converted to their respective phosphates by first reacting them with di-tert-butyl-N,N-diisopropylphosphoramidite in the presence of 1H-tetrazole, followed by oxidation with meta-chloroperoxybenzoic acid to give the intermediate tert-butylphosphate esters XVIII and XVII, respectively. Deprotection of these with trifluoroacetic acid in dichloromethane then gives the phosphates of formula II.

Figure 2:
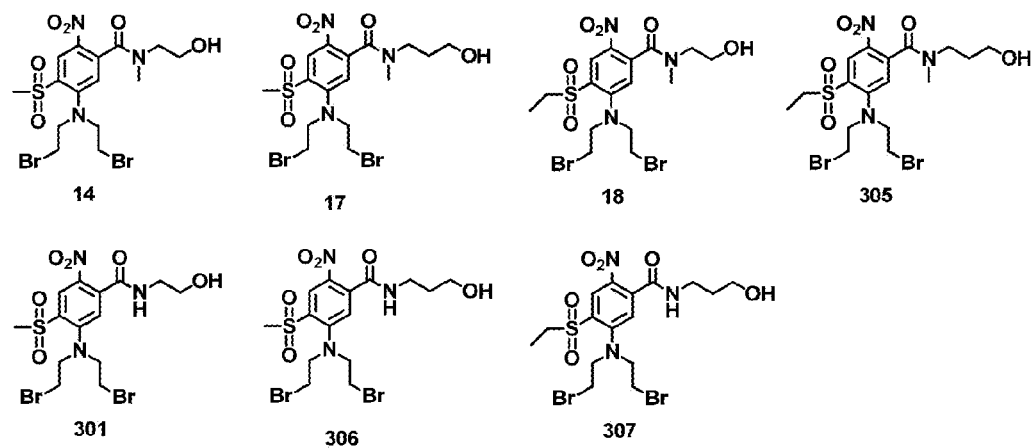
FIG. 2 shows representative dibromo mustard alcohols of Formula I

A scheme for synthesis of alcohol compound 14 (FIG. 2) is shown in FIG. 9.2. Reaction of 3,4-difluorobenzaldehyde (100) with sodium methylsulfinate gave methylsulfone 101, which was oxidised with sodium chlorite in phosphate buffer containing hydrogen peroxide to give acid 102. Nitration gave acid 103, which was reacted directly with diethanolamine to give diol 104, or first protected to give the tert-butyl ester 106, which was subsequently reacted with diethanolamine to give diol 107. Thionyl chloride mediated chlorination of diol 104 and subsequent reaction of the resulting acid chloride intermediate with 2-(methylamino) ethanol gave the dichloro mustard 111 which was subjected to lithium bromide mediated halogen exchange in methyl ethyl ketone at reflux to afford compound 14. Alternately diol 107 was converted to the bis-methanesulfonate ester 108 by reaction with methanesulfonyl chloride. Tert-butyl ester deprotection of bis-methanesulfonate ester 108 with trifluoroacetic acid gave acid 109. Reaction of this with oxalyl chloride in the presence of magnesium oxide provided the acid chloride intermediate which was further reacted with 2-(methylamino)ethanol to give the bis-methanesulfonate 1-carboxamide 112. Reaction of this with excess lithium bromide at room temperature in acetone gave compound 14.

A scheme for synthesis of alcohol compound 18 (FIG. 2) is shown in FIG. 9.3. Reaction of 3,4-difluorobenzaldehyde (100) with sodium ethylsulfinate gave ethylsulfone 113, which was oxidised with sodium chlorite in phosphate buffer containing hydrogen peroxide to give acid 114. Nitration gave acid 115, which was protected to give the tert-butyl ester 116. Subsequently reaction with diethanolamine gave diol 117 which was converted to the bis-methanesulfonate ester 118 by reaction with methanesulfonyl chloride. Tert-butyl ester deprotection of bis-methanesulfonate ester 118 with trifluoroacetic acid gave acid 119. Reaction of this with oxalyl chloride in the presence of magnesium oxide provided the acid chloride intermediate which was further reacted with 2-(methylamino)ethanol to give the bis-methanesulfonate 1-carboxamide 120. Reaction of this with excess lithium bromide at room temperature in acetone gave compound 18.

A scheme for synthesis of alcohol compound 301 (FIG. 2) is shown in FIG. 9.4. Thionyl chloride mediated chlorination of diol 104 and subsequent reaction of the resulting acid chloride intermediate with 1-aminoethanol gave the dichloro mustard 303 which was subjected to lithium bromide mediated halogen exchange in methyl ethyl ketone at reflux to afford compound 301.

Alternately bis-methanesulfonate ester 109 was reacted with oxalyl chloride in the presence of magnesium oxide to give the acid chloride intermediate which was further reacted with 1-aminoethanol to give the bis-methanesulfonate 1-carboxamide 304. Reaction of this with excess lithium bromide at room temperature in acetone gave compound 301.

Figure 10:
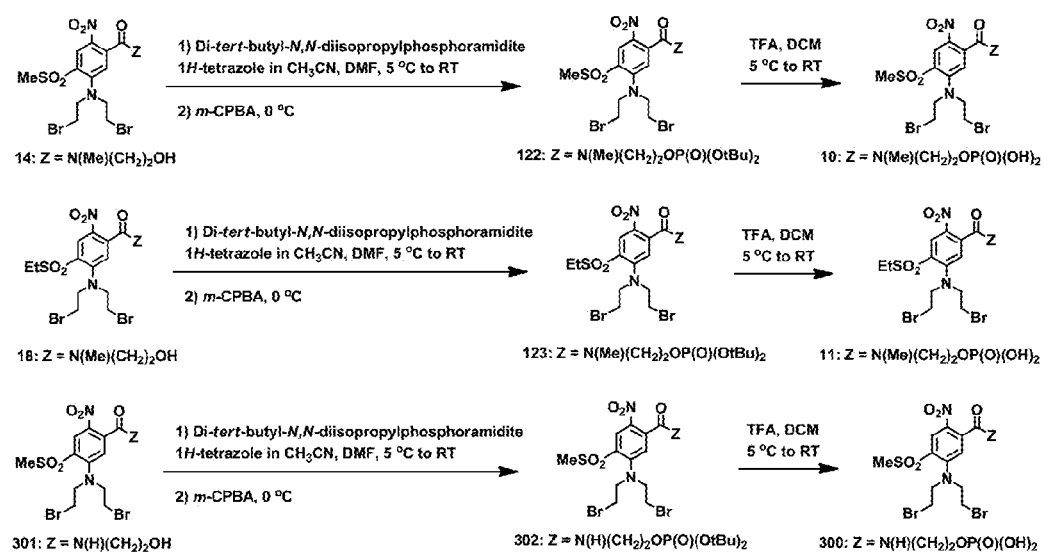
FIG. 10 shows a scheme for synthesis of phosphates 10, and 11 and 300 (FIG. 1)

A scheme for synthesis of phosphates 10, and 11 and 300 (FIG. 1) is shown in FIG. 10. Reaction of alcohols 14, 18 and 301 with di-tert-butyl-N,N-diisopropylphosphoramidite in the presence of 1H-tetrazole, followed by oxidation with meta-chloroperoxybenzoic acid gave the tert-butylphosphate esters 122, 123 and 302 respectively. Deprotection of these with trifluoroacetic acid in dichloromethane gave the phosphates 10, 11 and 300 respectively.

Figure 3:
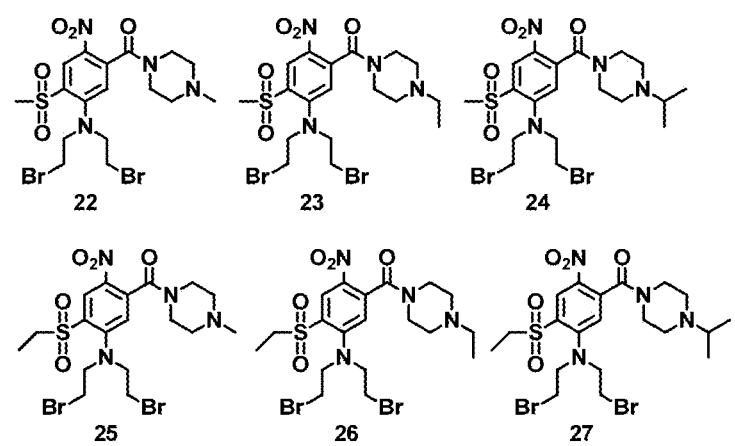
FIG. 3 shows representative dibromo mustards bearing substituted piperazine carboxamide sidechains of Formula I FIG. 3.1 shows representative bromomesylate mustards bearing substituted piperazine carboxamide sidechains of Formula I
Figure 11:
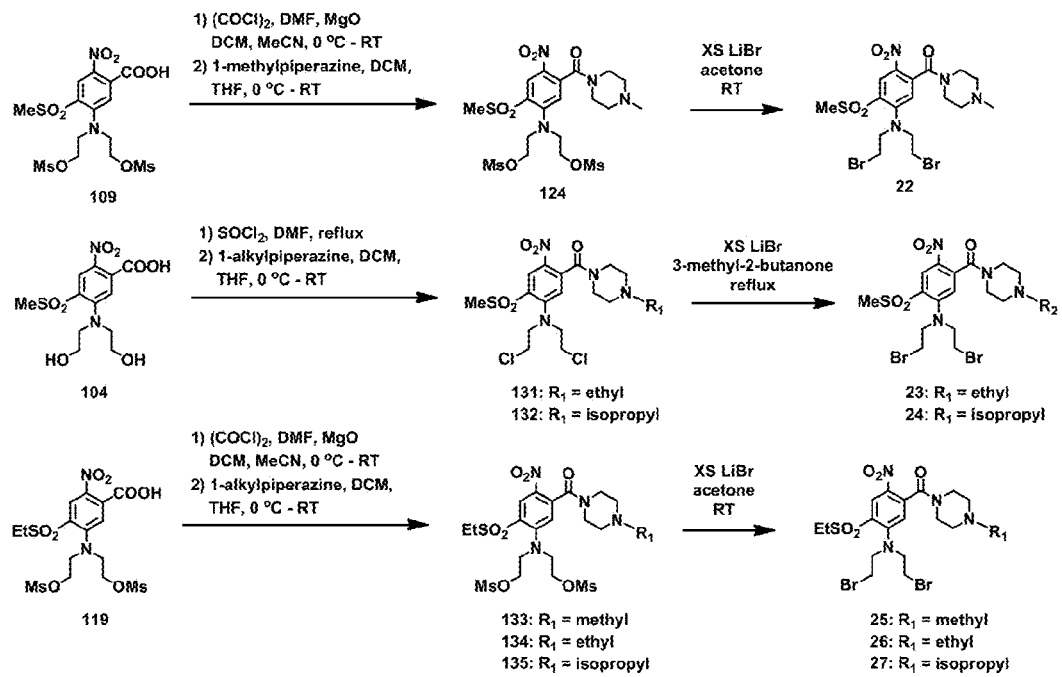
FIG. 11 shows a scheme for synthesis of prodrugs 22 to 27 (FIG. 3)

A scheme for synthesis of prodrugs 22 to 27 (FIG. 3) is shown in FIG. 11. Reaction of bis-methanesulfonate ester 109 with oxalyl chloride in the presence of magnesium oxide gave the acid chloride intermediate which was further reacted with 1-methylpiperazine to give the bis-methanesulfonate 1-carboxamide 124. Reaction of this with excess lithium bromide at room temperature in acetone gave compound 22. Thionyl chloride mediated chlorination of diol 104 and subsequent reaction of the resulting acid chloride intermediate with 1-ethylpiperazine and 1-iso-propylpiperazine gave the dichloro mustards 131 and 132, respectively. Lithium bromide mediated halogen exchange in methyl ethyl ketone at reflux then gave compounds 23 and 24, respectively. Reaction of bis-methanesulfonate ester 119 with oxalyl chloride in the presence of magnesium oxide gave the acid chloride intermediate which was further reacted with 1-methylpiperazine, 1-ethylpiperazine and 1-iso-propylpiperazine to give the bis-methanesulfonate 1-carboxamides 133, 134 and 135, respectively. Reaction of these with excess lithium bromide at room temperature in acetone gave compounds 25, 26 and 27, respectively.

Figures 13, 14:
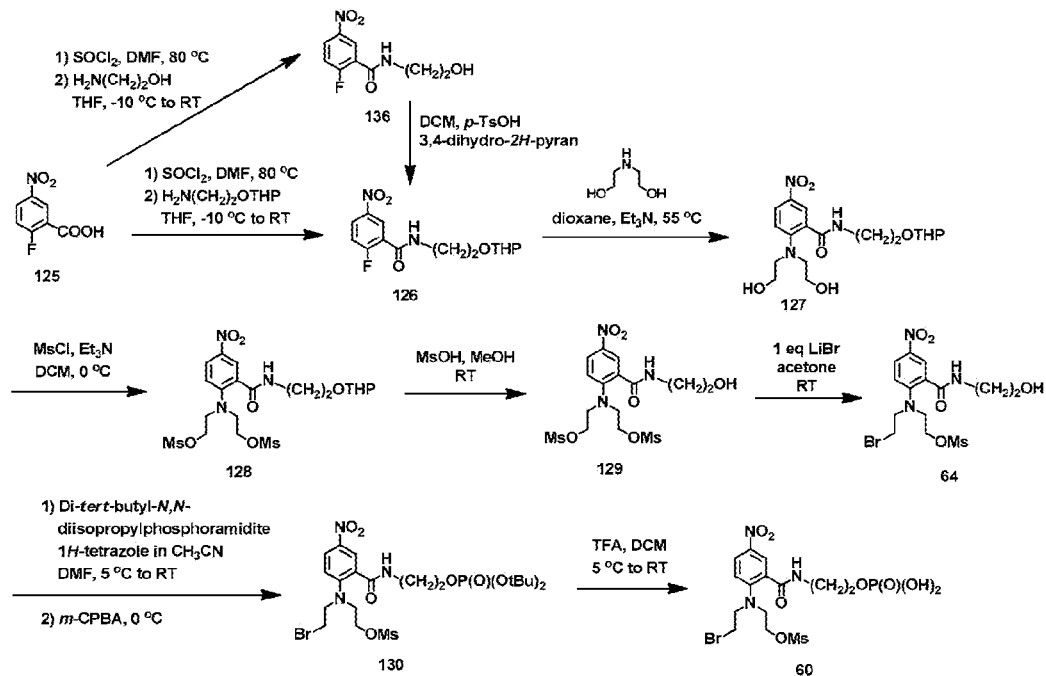
FIG. 13 shows a scheme for synthesis of alcohol 64 and phosphate 60
FIG. 14 shows the aqueous solubility of prior art prodrug 4 (Scheme 1) versus prodrugs 10, 11, 23 and 300 of the present invention. Table Footnote: $^a$Determined in α-Minimal Essential Media (α-MEM) containing 5% Fetal Calf Serum (FCS). $^b$Determined in Phosphate Buffered Saline (PBS) containing 2 equivalents of sodium bicarbonate. $^c$Determined in Lactate Buffer at pH=4.

A scheme for synthesis of alcohol 64 and phosphate 60 is shown in FIG. 13.

Reaction of 2-fluoro-5-nitrobenzoic acid 125 with thionyl chloride and subsequent reaction of the resulting acid chloride with ethanolamine gave amide 136. Subsequent THP-protection of this with 3,4-dihydro-2H-pyran in the presence of catalytic para-toluenesulfonic acid gave amide 126. This could be directly prepared by reaction of the previously described acid chloride with THP-protected ethanolamine. Reaction of amide 126 with diethanolamine then gave diol 127, which was converted to bis-methanesulfonate ester 128 by reaction with methanesulfonyl chloride. THP acetal deprotection with the methanesulfonic acid gave alcohol 129, which reacted with 1 equivalent of lithium bromide at room temperature in acetone to give compound 64. Reaction of this with di-tert-butyl-N,N-diisopropylphosphoramidite in the presence of 1H-tetrazole, followed by oxidation with meta-chloroperoxybenzoic acid gave tert-butylphosphate ester 130 which was deprotected employing trifluoroacetic acid in dichloromethane to give phosphate 60.

Solubility and stability of compounds in media (+5% Fetal calf serum), phosphate buffered saline (+sodium bicarbonate) or lactate buffer (at pH=4) were determined by HPLC.

Phosphate ester compounds typically exhibit superior aqueous solubility than the alcohol compounds they are derived from and are used here as pre-prodrugs. They are known to be rapidly cleaved in plasma by serum phosphatases to release the alcohol derivatives.

5-(bis(2-bromoethyl)amino)-N-(2-hydroxyethyl)-N-methyl-4-(methylsulfonyl)-2-nitrobenzamide (14)

Method 1

3-fluoro-4-(methylsulfonyl)benzaldehyde (101)

3,4-Difluorobenzaldehyde 100 (10.00 g, 70.37 mmol) was treated with sodium methanesulfinate (10.06 g, 98.53 mmol) in DMSO (200 mL) at the room temperature. The reaction mixture was heated at 75° C. under $N_2$ for 3 h then cooled to the room temperature, and poured into a beaker of ice-water. The white solid was collected by filtration, washed with water, and dried in a vacuum oven at 45° C. The crude product was purified by flash column chromatography on silica gel eluting with $CH_2Cl_2$/hexane (4:1) then neat $CH_2Cl_2$ to give 3-fluoro-4-(methylsulfonyl)benzaldehyde 101 (11.83 g, 83%) as a white powder. M.p. and $^1$HNMR consistent with the desired product. Note: At 75° C. predominantly the desired isomer is formed. At temperature above 75° C. for example 90° C., the ratio of the mono- to bis-methylsulfonyl is 2.4:1.

3-fluoro-4-(methylsulfonyl)benzoic acid (102)

To a solution of 3-fluoro-4-(methylsulfonyl)benzaldehyde 101 (11.50 g, 56.87 mmol) in $CH_3CN$ (105 mL) at the room temperature, a buffer solution of $NaH_2PO_4.4H_2O$ (1.86 g, 9.69 mmol) and conc. HCl (1.2 mL) in water (39.1 mL) and then $H_2O_2$ (35%, 9.7 mL, 285.21 mmol) were added. The reaction mixture was cooled to 0° C. and a solution of $NaClO_2$ (7.21 g, 79.72 mmol) in water (133 mL) was added dropwise. After stirring at room temperature for 5 h, the solvents were removed to half a volume and the white solid was collected by filtration. The filtrate was treated with conc. HCl and some more products were precipitated and collected by filtration. The combined solid was dried in a vacuum oven at 45° C. to give 3-fluoro-4-(methylsulfonyl) benzoic acid 102 (12.31 g, 99%) as a white powder. M.p. and $^1$HNMR consistent with the desired product.

5-fluoro-4-(methylsulfonyl)-2-nitrobenzoic acid (103)

3-Fluoro-4-(methylsulfonyl)benzoic acid 102 (13.00 g, 59.58 mmol) was dissolved in conc. $H_2SO_4$ (93 mL) and fuming $HNO_3$ (18 mL) was added dropwise at the room temperature. The reaction mixture was heated at 45° C. for 4 h, cooled to the room temperature and poured into a beaker of ice-water. The solid was collected by filtration, washed several times with water, and dried in a vacuum oven at 45° C. to provide 5-fluoro-4-(methylsulfonyl)-2-nitrobenzoic acid 103 (12.14 g, 77%) as a pale yellow solid. M.p. and $^1$HNMR consistent with the desired product.

5-(Bis(2-hydroxyethyl)amino)-4-(methylsulfonyl)-2-nitrobenzoic acid (104)

Method 1

5-Fluoro-4-(methylsulfonyl)-2-nitrobenzoic acid 103 (3.00 g, 11.40 mmol) was dissolved in DMSO (30 mL) and treated with diethanol amine (3.27 mL, 34.12 mmol) at room temperature. The reaction mixture was heated at 45° C. for 2 h, cooled to the room temperature and poured into a beaker of ice-water. The crude yellow gum was extracted with EtOAc/i-PrOH (4:1) (3×) and the combined organic phases were washed with water (6×), dried with $Na_2SO_4$ and concentrated under reduced pressure (water bath 35° C.) to give 5-(bis(2-hydroxyethyl)amino)-4-(methylsulfonyl)-2-nitrobenzoic acid 104 (3.64 g, 92%) as a yellow gum. $^1$HNMR [$(CD_3)_2SO$] δ 14.07 (br, s, 1H), 8.49 (s, 1H), 7.69 (s, 1H), 4.61 (br, s, 2H), 3.57-3.54 (m, 4H), 3.51-3.48 (m, 4H), 3.46 (s, 3H). HRMS (APCI) calcd for $C_{12}H_{17}N_2O_8S$ [M+H]$^+$ m/z 349.0705. found 349.0687.

5-(Bis(2-hydroxyethyl)amino)-4-(methylsulfonyl)-2-nitrobenzoic acid (104)

Method 2

5-Fluoro-4-(methylsulfonyl)-2-nitrobenzoic acid 103 (7.80 g, 29.64 mmol) was dissolved in DMSO (25 mL) and treated with diethanol amine (8.51 mL, 88.79 mmol). The reaction mixture was stirred at room temperature for 2 h then poured into a beaker of ice-cold aqueous HCl (2M, 100 mL), extracted with EtOAc/i-PrOH (4:1) (3×), washed with brine, dried with $Na_2SO_4$ and concentrated under reduced pressure to give 5-(bis(2-hydroxyethyl)amino)-4-(methylsulfonyl)-2-nitrobenzoic acid 104 (8.08 g, 78%) as a yellow powder.

5-(Bis(2-chloroethyl)amino)-N-(2-hydroxyethyl)-N-methyl-4-(methylsulfonyl)-2-nitrobenzamide (111)

A stirred solution of 5-(bis(2-hydroxyethyl)amino)-4-(methylsulfonyl)-2-nitrobenzoic acid 104 (1.0 g, 2.87 mmol) in $SOCl_2$ (25 mL) and DMF (3 drops) was heated under reflux for 4 h. The excess $SOCl_2$ was removed by distillation under reduced pressure and the residue was dissolved in $CH_2Cl_2$ (10 mL) and THF (6 mL), cooled to 0° C. and treated with 2-(methylamino)ethanol (822 ⌷ L, 10.25 mmol). The reaction mixture was stirred at 0° C. for 20 min then warmed to the room temperature, acidified with aqueous HCl (0.5 M, 8 mL) and extracted with EtOAc (2×). The combined organic phases were washed with brine, dried with $Na_2SO_4$ and evaporated to dryness under reduce pressure. The crude product was purified by flash column chromatography on silica gel eluting with $CH_2Cl_2$/MeOH (20:1) to give 5-(bis(2-chloroethyl)amino)-N-(2-hydroxyethyl)-N-methyl-4-(methylsulfonyl)-2-nitrobenzamide 111 (390 mg, 31%) as a mixture of atropisomers, as a yellow gum. $^1$HNMR [$(CD_3)_2SO$] δ 8.66 (s, 0.4H), 8.64 (s, 0.6H), 7.71 (s, 0.6H), 7.66 (s, 0.4H), 4.83-4.78 (2t, J=5.4 Hz, 1H), 3.78 (br, s, 4H), 3.76-3.71 (m, 4H), 3.69-3.64 (m, 1H), 3.55-3.52 (m, 1H), 3.48 (s, 1.6H), 3.47 (s, 1.4H), 3.19 (br, s, 2H), 3.04 (s, 1.6H), 2.85 (s, 1.4H). HRMS(ESI) calcd for $C_{15}H_{21}Cl_2N_3NaO_6S$ [M+Na]$^+$ m/z 464.0407. found 464.0420.

5-(Bis(2-bromoethyl)amino)-N-(2-hydroxyethyl)-N-methyl-4-(methylsulfonyl)-2-nitrobenzamide (14)

A solution of (5-(bis(2-chloroethyl)amino)-N-(2-hydroxyethyl)-N-methyl-4-(methylsulfonyl)-2-nitrobenzamide 111 (320 mg, 0.72 mmol) in 3-methyl-2-butanone (13 mL) was treated with LiBr (1.26 g, 14.51 mmol) and heated to reflux overnight. The reaction mixture was cooled to the room temperature and the solvent was removed under reduced pressure. The residue was dissolved in EtOAc and washed with water (3×), dried with $Na_2SO_4$ and concentrated under reduced pressure. The crude mixture was resubmitted to LiBr (2×) and worked up as above. The final product was purified by flash column chromatography on silica gel eluting with $CH_2Cl_2$/MeOH (20:1) and further recrystallized from $CH_2Cl_2$/i$Pr_2O$ to give 5-(bis(2-bromoethyl)amino)-N-(2-hydroxyethyl)-N-methyl-4-(methylsulfonyl)-2-nitrobenzamide 14 (258 mg, 67%) as a mixture of atropisomers, as a pale yellow solid: m.p. 138-140° C.;

¹HNMR [(CD₃)₂SO] δ 8.65 (s, 0.4H), 8.64 (s, 0.6H), 7.72 (s, 0.6H), 7.67 (s, 0.4H), 4.82-4.77 (2t, J=5.5 Hz, 1H), 3.84-3.77 (m, 4H), 3.69-3.59 (m, 5H), 3.58-3.52 (m, 1H), 3.49 (s, 1.6H), 3.48 (s, 1.4H), 3.19 (br, s, 2H), 3.04 (s, 1.6H), 2.86 (s, 1.4H). Anal. calcd for $C_{15}H_{21}Br_2N_3O_6S.0.2iPr_2O$: C, 35.30; H, 4.28; N, 7.62%. found: C, 35.06; H, 4.09; N, 7.64%.

5-(bis(2-bromoethyl)amino)-N-(2-hydroxyethyl)-N-methyl-4-(methylsulfonyl)-2-nitrobenzamide (14)

Method 2 tert-Butyl 5-fluoro-4-(methylsulfonyl)-2-nitrobenzoate (106)

5-Fluoro-4-(methylsulfonyl)-2-nitrobenzoic acid 103 (8.24 g, 31.31 mmol) was dissolved in CH₃CN (48 mL) at 50° C., cooled to the room temperature and treated with tert-butyl acetate (48 mL) and perchloric acid (70%, 2.64 mL, 43.83 mmol). The reaction mixture was stirred at room temperature for 48 h and the solvents were removed under reduced pressure (water bath 50° C.). The residue was recrystallized from MeOH/water in the cold room. The product was collected by filtration to give tert-butyl 5-fluoro-4-(methylsulfonyl)-2-nitrobenzoate 106 (5.70 g, 57%) as pale yellow crystals: m.p. 99-101° C.; ¹HNMR (CDCl₃) δ 8.58 (d, J=5.7 Hz, 1H), 7.57 (d, J=8.5 Hz, 1H), 3.30 (s, 3H), 1.60 (s, 9H). Anal. calcd for $C_{12}H_{14}FNO_6S$: C, 45.14; H, 4.42; N, 4.39%. found: C, 45.44; H, 4.47; N, 4.32%. Note: The filtrate was diluted with water and treated with aqueous HCl (4 M) to recover some unreacted starting material (3.09 g) that was collected by filtration.

tert-Butyl 5-(bis(2-hydroxyethyl)amino)-4-(methylsulfonyl)-2-nitrobenzoate (107)

A solution of tert-butyl 5-fluoro-4-(methylsulfonyl)-2-nitrobenzoate 106 (6.64 g, 20.79 mmol) in DMSO (15 mL) was treated with diethanol amine (2.79 mL, 29.12 mmol). The reaction mixture was stirred at room temperature for 2 h then poured into a beaker of ice-water, extracted with diethyl ether (3×), dried with Na₂SO₄ and concentrated under reduced pressure. The yellow gum was purified by flash column chromatography on silica gel eluting with CH₂Cl₂/MeOH (19:1) to give tert-butyl 5-(bis(2-hydroxyethyl)amino)-4-(methylsulfonyl)-2-nitrobenzoate 107 (7.35 g, 87%) as a yellow gum. ¹HNMR [(CD₃)₂SO]δ 8.50 (s, 1H), 7.63 (s, 1H), 4.64 (t, J=5.0 Hz, 2H), 3.58-3.54 (m, 4H), 3.52-3.50 (m, 4H), 3.45 (s, 3H), 1.53 (s, 9H). HRMS(ESI) calcd for $C_{16}H_{25}N_2O_8S$ [M+H]⁺ m/z 405.1347. found 405.1326. Note: At temperature higher than room temperature, for example 40 to 50° C. a significant amount of the tert-butyl 5-(2-((2-hydroxyethyl)amino)ethoxy)-4-(methylsulfonyl)-2-nitrobenzoate product is formed (i.e. O-alkylation in competition with N-alkylation).

tert-Butyl 5-(bis(2-((methylsulfonyl)oxy)ethyl) amino)-4-(methylsulfonyl)-2-nitrobenzoate (108)

To a solution of tert-butyl 5-(bis(2-hydroxyethyl)amino)-4-(methylsulfonyl)-2-nitrobenzoate 107 (8.52 g, 21.07 mmol) in CH₂Cl₂ (290 mL) and Et₃N (10.28 mL, 73.75 mmol) at 0° C. MsCl (4.90 mL, 63.22 mmol) was added dropwise. The reaction mixture was stirred for 20 min at 0° C. then warmed to the room temperature, diluted with CH₂Cl₂, washed with water (3×), dried with Na₂SO₄ and concentrated under reduced pressure. The residues was purified by flash column chromatography on silica gel eluting with CH₂Cl₂/MeOH (19:1) to give tert-butyl 5-(bis(2-((methylsulfonyl)oxy)ethyl)amino)-4-(methylsulfonyl)-2-nitrobenzoate 108 (10.60 g, 90%) as a yellow gum. ¹HNMR [(CD₃)₂SO] δ 8.52 (s, 1H), 7.83 (s, 1H), 4.36 (t, J=5.2 Hz, 4H), 3.77 (t, J=5.0 Hz, 4H), 3.43 (s, 3H), 3.14 (s, 6H), 1.53 (s, 9H). HRMS(ESI) calcd for $C_{18}H_{28}N_2NaO_{12}S_3$ [M+Na]⁺ m/z 583.0674. found 583.0697.

5-(Bis(2-((methylsulfonyl)oxy)ethyl)amino)-4-(methylsulfonyl)-2-nitrobenzoic acid (109)

tert-Butyl 5-(bis(2-((methylsulfonyl)oxy)ethyl)amino)-4-(methylsulfonyl)-2-nitrobenzoate 108 (10.60 g, 18.91) in CH₂Cl₂ (56 mL) was treated with TFA (21 mL) at 5° C. The reaction was stirred at the room temperature for 2 h, and the solvents were removed under reduced pressure. The residue was then dissolved in EtOAc and the solvent was evaporated to dryness to remove the excess TFA. The yellow residue was dissolved in CH₂Cl₂ and precipitated with iPr₂O to give 5-(bis(2-((methylsulfonyl)oxy)ethyl)amino)-4-(methylsulfonyl)-2-nitrobenzoic acid 109 (9.54 g, 100%) as a yellow gum. ¹HNMR [(CD₃)₂SO] δ 8.50 (s, 1H), 7.89 (s, 1H), 4.35 (t, J=5.1 Hz, 4H), 3.75 (t, J=5.2 Hz, 4H), 3.44 (s, 3H), 3.14 (s, 6H). HRMS(ESI) calcd for $C_{14}H_{20}N_2NaO_{12}S_3$[M+Na]⁺ m/z 527.0062. found 527.0071.

((5-((2-Hydroxyethyl)(methyl)carbamoyl)-2-(methylsulfonyl)-4-nitrophenyl)azanediyl)bis(ethane-2,1-diyl) dimethanesulfonate (112)

A solution of 5-(bis(2-((methylsulfonyl)oxy)ethyl) amino)-4-(methylsulfonyl)-2-nitrobenzoic acid 109 (2.66 g, 5.27 mmol) in CH₂Cl₂ (80 mL) and CH₃CN (20 mL) was treated with MgO (3.19 g, 79.09 mmol) at the room temperature then cooled to 0° C. and treated with oxalyl chloride (2.71 mL, 31.62 mmol) and DMF (3 drops). The reaction mixture was stirred at 0° C. for 1 h then warmed to the room temperature for 3 h. The mixture was filtered through a short pad of Celite and the solvents were removed under reduced pressure. The residue was dissolved in CH₂Cl₂ (80 mL) and THF (20 mL), cooled to 0° C. and treated with 2-(methylamino)ethanol (1.27 mL, 15.85 mmol) and warm to the room temperature for 20 min. The mixture was washed with water (3×), dried with Na₂SO₄ and concentrated under reduced pressure. The residues was purified by flash column chromatography on silica gel eluting with CH₂Cl₂/MeOH (19:1) to give ((5-((2-hydroxyethyl)(methyl)carbamoyl)-2-(methylsulfonyl)-4-nitrophenyl)azanediyl)bis(ethane-2,1-diyl) dimethanesulfonate 112 (2.20 g, 74%) as a mixture of atropisomers, as a yellow gum. ¹HNMR [(CD₃)₂SO] δ 8.65 (s, 0.5H), 8.64 (s, 0.5H), 7.72 (s, 0.5H), 7.67 (s, 0.5), 4.84-4.79 (2t, J=5.2 Hz, 1H), 4.36-4.34 (m, 4H), 3.79-3.76 (m, 4H), 3.68-3.53 (m, 2H), 3.44 (s, 3H), 3.34-3.29 (m, 2H), 3.14 (s, 6H), 3.04 (s, 1.6H), 2.86 (s, 1.4H). HRMS(ESI) calcd for $C_{17}H_{27}N_3NaO_{12}S_3$[M+Na]⁺ m/z 584.0647. found 584.0649.

5-(Bis(2-bromoethyl)amino)-N-(2-hydroxyethyl)-N-methyl-4-(methylsulfonyl)-2-nitrobenzamide (14)

((5-((2-Hydroxyethyl)(methyl)carbamoyl)-2-(methylsulfonyl)-4-nitrophenyl)azanediyl)bis(ethane-2,1-diyl) dimethanesulfonate 112 (3.70 g, 6.59 mmol) was dissolved in acetone (200 mL) and treated with LiBr (11.44 g, 131.72 mmol) at the room temperature. The reaction mixture was stirred overnight and the solvent was removed. The residue was dissolved in EtOAc and washed with water (2×), dried with $Na_2SO_4$ and concentrated under reduced pressure. The crude product was purified by flash column chromatography on silica gel eluting with $CH_2Cl_2$/MeOH (20:1) to give 5-(bis(2-bromoethyl)amino)-N-(2-hydroxyethyl)-N-methyl-4-(methylsulfonyl)-2-nitrobenzamide 14 (3.13 g, 89%) as a mixture of atropisomers, as a yellow solid. M.p. and $^1$HNMR identical to that previously observed.

5-(Bis(2-bromoethyl)amino)-4-(ethylsulfonyl)-N-(2-hydroxyethyl)-N-methyl-2-nitrobenzamide (18)

4-(Ethylsulfonyl)-3-fluorobenzaldehyde (113)

3,4-Difluorobenzaldehyde 100 (23.50 g, 165.38 mmol) was treated with sodium ethanesulfinate (23.00 g, 198.09 mmol) in DMSO (230 mL) at the room temperature. The reaction mixture was heated at 75° C. under $N_2$ for 4 h then cooled to the room temperature, and poured into a beaker of ice-water. The white precipitates were collected by filtration, washed with water, and dried in a vacuum oven at 45° C. The solid was then recrystallized from $CH_2Cl_2$/$iPr_2O$ to give 4-(ethylsulfonyl)-3-fluorobenzaldehyde 113 (28.48 g, 80%) as a white powder: m.p. 107-110° C.; $^1$HNMR (CDCl$_3$) δ 10.09 (d, J=1.9 Hz, 1H), 8.16 (dd, J=6.5 Hz, 1.4, 1H), 7.87 (dd, J=7.9 Hz, 1.4, 1H), 7.75 (dd, J=9.4 Hz, 1.4, 1H), 3.38 (2q, J=7.4 Hz, 2H), 1.33 (2t, J=7.5 Hz, 3H). Anal. calcd for $C_9H_9FO_3S$: C, 49.99; H, 4.20; F, 8.79%. found: C, 50.19; H, 4.23; F, 8.91%.

4-(Ethylsulfonyl)-3-fluorobenzoic acid (114)

To a solution of 4-(ethylsulfonyl)-3-fluorobenzaldehyde 113 (30.70 g, 141.98 mmol) in $CH_3CN$ (280 mL) at the room temperature, a buffer solution of $NaH_2PO_4.4H_2O$ (4.65 g, 24.21 mmol) and conc. HCl (3.2 mL) in water (105 mL) and then $H_2O_2$ (35%, 24.1 mL, 708.62 mmol) were added. The reaction mixture was cooled to 0° C. and a solution of $NaClO_2$ (17.98 g, 198.81 mmol) in water (350 mL) was added dropwise. After stirring at room temperature for 5 h, the solvents were removed to half a volume under reduced pressure and the white solid was collected by filtration. The filtrate was treated with conc. HCl and some more products were precipitated and collected by filtration. The combined solid was dried in a vacuum oven at 45° C. to give 4-(ethylsulfonyl)-3-fluorobenzoic acid 114 (32.65 g, 99%) as a white powder: m.p. 184-186° C.; $^1$HNMR (CDCl$_3$) δ 8.12-8.07 (m, 2H), 7.98-7.95 (m, 1H), 3.38 (q, J=7.4 Hz, 2H), 1.34 (t, J=7.4 Hz, 3H). Anal. calcd for $C_9H_9FO_4S$: C, 46.55; H, 3.91; F, 8.18%. found: C, 46.82; H, 3.99; F, 8.33%.

4-(Ethylsulfonyl)-5-fluoro-2-nitrobenzoic acid (115)

4-(Ethylsulfonyl) 3-fluorobenzoic acid 114 (15.65 g, 67.39 mmol) was dissolved in conc. $H_2SO_4$ (107 mL) and fuming $HNO_3$ (21 mL) was added dropwise at the room temperature. The reaction mixture was heated at 45° C. for 4 h, cooled to the room temperature and poured into a beaker of ice-water. The solid was collected by filtration, washed with water, and dried in a vacuum oven at 45° C. to provide 4-(ethylsulfonyl)-5-fluoro-2-nitrobenzoic acid 115 (16.63 g, 89%) as a pale yellow solid: m.p. 140-143° C.; $^1$HNMR [(CD$_3$)$_2$SO] δ 14.59 (br, s, 1H), 8.41 (d, J=5.8 Hz, 1H), 8.07 (d, J=9.3 Hz, 1H), 3.53 (q, J=7.4 Hz, 2H), 1.20 (t, J=7.4 Hz, 3H). HRMS(ESI) calcd for $C_9H_9FNO_6S$ [M+1]$^+$ m/z 278.0130. found 278.0129.

tert-Butyl 4-(Ethylsulfonyl)-5-fluoro-2-nitrobenzoate (116)

4-(Ethylsulfonyl)-5-fluoro-2-nitrobenzoic acid 115 (24.35 g, 87.83 mmol) was dissolved tert-butyl acetate (150 mL) and treated with perchloric acid (70%, 3.70 mL, 61.48 mmol). The reaction mixture was stirred at room temperature overnight then further treated with perchloric acid (70%, 3.70 mL, 61.48 mmol) and left stirring for 24 h. The solvent was then removed under reduced pressure (water bath 50° C.), and the residue was recrystallized from MeOH/water in the cold room. The product was collected by filtration and further recrystallized from $CH_2Cl_2$/$iPr_2O$ to give tert-butyl 4-(ethylsulfonyl)-5-fluoro-2-nitrobenzoate 116 (20.51 g, 70%) as pale yellow crystals: m.p. 105-107° C.; $^1$HNMR (CDCl$_3$) δ 8.54 (d, J=5.7 Hz, 1H), 7.54 (d, J=8.5 Hz, 1H), 3.37 (2q, J=7.6 Hz, 2H), 1.59 (s, 9H), 1.37 (2t, J=7.4 Hz, 3H). Anal. calcd for $C_{13}H_{16}FNO_6S.0.1iPr_2O$: C, 47.58; H, 5.05; N, 4.08%. found: C, 47.35; H, 4.87; N, 4.17%.

tert-Butyl 5-(bis(2-hydroxyethyl)amino)-4-(ethylsulfonyl)-2-nitrobenzoate (117)

A solution of tert-butyl 4-(ethylsulfonyl)-5-fluoro-2-nitrobenzoate 116 (13.15 g, 39.45 mmol) in DMSO (30 mL) was treated with diethanol amine (5.06 mL, 52.81 mmol). The reaction mixture was stirred at room temperature for 2 h then poured into a beaker of ice-water, extracted with diethyl ether (3×), dried with $Na_2SO_4$ and concentrated under reduced pressure. The yellow gum was purified by flash column chromatography on silica gel eluting with $CH_2Cl_2$/MeOH (49:1) to give tert-butyl 5-(bis(2-hydroxyethyl)amino)-4-(ethylsulfonyl)-2-nitrobenzoate 117 (12.90 g, 78%) as a yellow gum. $^1$HNMR [(CD$_3$)$_2$SO] δ 8.48 (s, 1H), 7.64 (s, 1H), 4.64 (t, J=4.8 Hz, 2H), 3.71 (q, J=7.3, 2H), 3.57-3.49 (m, 8H), 1.53 (s, 9H), 0.10 (t, J=7.3 Hz, 3H). HRMS(ESI) calcd for $C_{17}H_{27}N_2O_8S$ [M+H]$^+$ m/z 419.1483. found 419.1483.

tert-Butyl 5-(Bis(2-((methylsulfonyl)oxy)ethyl)amino)-4-(ethylsulfonyl)-2-nitrobenzoate (118)

To a solution of tert-Butyl 5-(bis(2-hydroxyethyl)amino)-4-(ethylsulfonyl)-2-nitrobenzoate 117 (12.90 g, 30.83 mmol) in $CH_2Cl_2$ (500 mL) and $Et_3N$ (15.04 mL, 107.90 mmol) at 0° C. MsCl (7.20 mL, 92.93 mmol) was added dropwise. The reaction mixture was stirred for 20 min at 0° C. then warmed to the room temperature, diluted with $CH_2Cl_2$, washed with water (3×), dried with $Na_2SO_4$ and concentrated under reduced pressure. The residues was purified by flash column chromatography on silica gel eluting with EtOAc/hexane (4:1) to give tert-butyl 5-(bis(2-((methylsulfonyl)oxy)ethyl)amino)-4-(ethylsulfonyl)-2-nitrobenzoate 118 (14.80 g, 84%) as a yellow powder. $^1$HNMR [(CD$_3$)$_2$SO] δ 8.50 (s, 1H), 7.81 (s, 1H), 4.36 (t, J=5.0 Hz, 4H), 3.77 (t, J=5.0 Hz, 4H), 3.64 (q, J=7.4 Hz, 2H), 3.15 (s, 6H), 1.53 (s, 9H), 1.08 (t, J=7.3 Hz, 3H). HRMS(ESI) calcd for $C_{19}H_{31}N_2O_{12}S_3$[M+H]$^+$ m/z 575.1020. found 575.1034.

5-(Bis(2-((methylsulfonyl)oxy)ethyl)amino)-4-(ethylsulfonyl)-2-nitrobenzoic acid 119 tert-Butyl 5-(bis(2-((methylsulfonyl)oxy)ethyl)amino)-4-(ethylsulfonyl)-2-nitrobenzoate 118 (14.80, 25.76) in $CH_2Cl_2$ (80 mL) was treated with TFA (40 mL) at 5° C. The reaction was stirred at the room temperature for 2 h, and the solvents were removed under reduced pressure. The residue was then dissolved in EtOAc and the solvent was evaporated to dryness to remove the excess TFA. The yellow residue was dissolved in $CH_2Cl_2$ and precipitated with $iPr_2O$ to give 5-(bis(2-((methylsulfonyl)oxy)ethyl)amino)-4-(ethylsulfonyl)-2-nitrobenzoic acid 119 (13.22 g, 99%) as a yellow gum. $^1$HNMR [$(CD_3)_2SO$] δ 8.50 (s, 1H), 7.88 (s, 1H), 4.35 (t, J=5.0 Hz, 4H), 3.75 (t, J=5.0 Hz, 4H), 3.65 (q, J=7.3 Hz, 2H), 3.15 (s, 6H), 1.07 (t, J=7.4 Hz, 3H). HRMS(ESI) calcd for $C_{15}H_{23}N_2O_{12}S_3[M+H]^+$ m/z 519.0413. found 519.0408.

((5-((2-Hydroxyethyl)(methyl)carbamoyl)-2-(ethylsulfonyl)-4-nitrophenyl)azanediyl)bis(ethane-2,1-diyl) dimethanesulfonate (120)

A solution of 5-(bis(2-((methylsulfonyl)oxy)ethyl)amino)-4-(ethylsulfonyl)-2-nitrobenzoic acid 119 (3.21 g, 6.19 mmol) in $CH_2Cl_2$ (50 mL) and $CH_3CN$ (5 mL) was treated with MgO (4.99 g, 123.81 mmol) at the room temperature then cooled to 0° C. and treated with oxalyl chloride (3.19 mL, 37.14 mmol) and DMF (3 drops). The reaction mixture was stirred at 0° C. for 1 h then warmed to the room temperature for 3 h. The mixture was filtered through a short pad of Celite and the solvents were removed under reduced pressure. The residue was dissolved in $CH_2Cl_2$ (105 mL) and THF (25 mL), cooled to 0° C. and treated with 2-(methylamino)ethanol (1.66 mL, 20.64 mmol) and warm to the room temperature for 20 min. The mixture was washed with water (3×), dried with $Na_2SO_4$ and concentrated under reduced pressure. The residues was purified by flash column chromatography on silica gel eluting with $CH_2Cl_2$/MeOH (19:1) to give ((5-((2-hydroxyethyl)(methyl)carbamoyl)-2-(ethylsulfonyl)-4-nitrophenyl) azanediyl)bis(ethane-2,1-diyl) dimethanesulfonate 120 (2.35 g, 66%) as a mixture of atropisomers, as a yellow gum. $^1$HNMR [$(CD_3)_2SO$] δ 8.64 (s, 0.3H), 8.63 (s, 0.7H), 7.71 (s, 0.4H), 7.65 (s, 0.6H), 4.83-4.78 (2t, J=5.2 Hz, 1H), 4.36-4.33 (m, 4H), 3.78-3.75 (m, 4H), 3.69-3.53 (m, 6H), 3.15 (s, 6H), 3.04 (s, 1.6H), 2.86 (s, 1.4H), 1.10 (t, J=7.4 Hz, 3H). HRMS(ESI) calcd for $C_{18}H_{30}N_3O_{12}S_3[M+H]^+$ m/z 576.0972. found 576.0986.

5-(Bis(2-bromoethyl)amino)-N-(2-hydroxyethyl)-N-methyl-4-(ethylsulfonyl)-2-nitrobenzamide (18)

((5-((2-Hydroxyethyl)(methyl)carbamoyl)-2-(ethylsulfonyl)-4-nitrophenyl)azanediyl)bis(ethane-2,1-diyl) dimethanesulfonate 120 (2.00 g, 3.47 mmol) was dissolved in acetone (50 mL) and treated with LiBr (6.03 g, 69.49 mmol) at the room temperature. The reaction mixture was stirred overnight and the solvent was removed. The residue was dissolved in EtOAc and washed with water (2×), dried with $Na_2SO_4$ and concentrated under reduced pressure. The crude product was purified by flash column chromatography on silica gel eluting with $CH_2Cl_2$/MeOH (20:1) to give 5-(bis (2-bromoethyl)amino)-N-(2-hydroxyethyl)-N-methyl-4-(ethylsulfonyl)-2-nitrobenzamide 18 (1.81 g, 96%) as a mixture of atropisomers, as a yellow gum. $^1$HNMR [$(CD_3)_2SO$] δ 8.64 (s, 0.4H), 8.63 (s, 0.6H), 7.70 (s, 0.6H), 7.66 (s, 0.4H), 4.83-4.77 (2t, J=5.5 Hz, 1H), 3.84-3.76 (m, 4H), 3.73- 3.66 (m, 3H), 3.64-3.58 (m, 4H), 3.55-3.52 (m, 1H), 3.23-3.07 (m, 2H), 3.04 (s, 1.6H), 2.86 (s, 1.4H), 1.10 (t, J=7.4 Hz, 3H). HRMS (ESI) calcd for $C_{16}H_{23}Br_2N_3NaO_6S$ $[M+Na]^+$ m/z 565.9556. found 565.9567.

5-(Bis(2-bromoethyl)amino)-N-(2-hydroxyethyl)-4-(methylsulfonyl)-2-nitrobenzamide (301)

Method 1

5-(Bis(2-chloroethyl)amino)-N-(2-hydroxyethyl)-4-(methylsulfonyl)-2-nitrobenzamide (303)

A stirred solution of 5-(bis(2-hydroxyethyl)amino)-4-(methylsulfonyl)-2-nitrobenzoic acid 104 (490 mg, 1.41 mmol) in $SOCl_2$ (12.5 mL) and DMF (3 drops) was heated under reflux for 4 h. The excess $SOCl_2$ was removed by distillation under reduced pressure and the residue dissolved in $CH_2Cl_2$ (5 mL) and THF (3 mL), cooled to 0° C. and treated with 2-aminoethanol (296 μL, 4.91 mmol). The reaction mixture was stirred at 0° C. for 20 min then warmed to the room temperature, acidified with aqueous HCl (0.5 M, 4 mL) and extracted with EtOAc (2×). The combined organic phases were washed with brine, dried with $Na_2SO_4$ and evaporated to dryness under reduce pressure. The crude product was purified by flash column chromatography on silica gel eluting with $CH_2Cl_2$/MeOH (25:1) to give 5-(bis (2-chloroethyl)amino)-N-(2-hydroxyethyl)-4-(methylsulfonyl)-2-nitrobenzamide 303 (300 mg, 50%) as a yellow gum. $^1$HNMR [$(CD_3)_2SO$] δ 8.80 (t, J=5.7 Hz, 1H), 8.51 (s, 1H), 7.69 (s, 1H), 4.79 (t, J=5.4 Hz, 1H), 3.81-3.77 (m, 4H), 3.72-3.69 (m, 4H), 3.55-3.51 (m, 2H), 3.48 (s, 3H), 3.34-3.29 (m, 2H). LRMS (APCI) calcd for $C_{14}H_{20}Cl_2N_3O_6S$ $[M+H]^+$ m/z 429.30. found 429.00.

5-(Bis(2-bromoethyl)amino)-N-(2-hydroxyethyl)-4-(methylsulfonyl)-2-nitrobenzamide (301)

A solution of 5-(bis(2-chloroethyl)amino)-N-(2-hydroxyethyl)-4-(methylsulfonyl)-2-nitro benzamide 303 (250 mg, 0.58 mmol) in 3-methyl-2-butanone (10 mL) was treated with LiBr (1.02 g, 11.75 mmol) and heated to reflux overnight. The reaction mixture was cooled to the room temperature and the solvent was removed under reduced pressure. The residue was dissolved in EtOAc and washed with water (3×), dried with $Na_2SO_4$ and concentrated under reduced pressure. The crude mixture was resubmitted to LiBr (2×) and worked up as above. The final product was purified by flash column chromatography on silica gel eluting with $CH_2Cl_2$/MeOH (20:1) to give 5-(bis(2-bromoethyl)amino)-N-(2-hydroxyethyl)-4-(methylsulfonyl)-2-nitrobenzamide 301 (250 mg, 83%) as a pale yellow solid. M.p. and $^1$HNMR identical to that previously reported (Denny et al, WO2005/042471A1).

5-(Bis(2-bromoethyl)amino)-N-(2-hydroxyethyl)-4-(methylsulfonyl)-2-nitrobenzamide (301)

Method 2

((5-((2-Hydroxyethyl)carbamoyl)-2-(methylsulfonyl)-4-nitrophenyl)azanediyl)bis(ethane-2,1-diyl) dimethanesulfonate (304)

A solution of 5-(bis(2-((methylsulfonyl)oxy)ethyl) amino)-4-(methylsulfonyl)-2-nitrobenzoic acid 109 (3.35 g, 6.64 mmol) in $CH_2Cl_2$ (100 mL) and $CH_3CN$ (25 mL) was treated with MgO (4.01 g, 99.60 mmol) at the room temperature then cooled to 0° C. and treated with oxalyl chloride (3.42 mL, 39.84 mmol) and DMF (3 drops). The reaction mixture was stirred at 0° C. for 1 h then warmed to the room temperature for 3 h. The mixture was filtered through a short pad of Celite and the solvents were removed under reduced pressure. The residue was dissolved in $CH_2Cl_2$ (100 mL) and THF (25 mL), cooled to 0° C. and treated with ethanol amine (601 μL, 9.96 mmol) and warm to the room temperature for 20 min. The mixture was washed with water (3×), dried with $Na_2SO_4$ and concentrated under reduced pressure. The residues was purified by flash column chromatography on silica gel eluting with $CH_2Cl_2$/MeOH (19:1) to give ((5-((2-hydroxyethyl)carbamoyl)-2-(methylsulfonyl)-4-nitrophenyl)azanediyl)bis(ethane-2,1-diyl) dimethanesulfonate 304 (3.40 g, 94%) as a yellow gum. $^1$HNMR [$(CD_3)_2SO$] δ 8.71 (t, J=5.7 Hz, 1H), 8.51 (s, 1H), 7.73 (s, 1H), 4.77 (t, J=5.0 Hz, 1H), 4.35 (t, J=5.2 Hz, 4H), 3.72 (t, J=5.2 Hz, 4H), 3.55-3.51 (m, 2H), 3.44 (s, 3H), 3.34-3.29 (m, 2H), 3.16 (s, 6H). HRMS(ESI) calcd for $C_{16}H_{25}N_3NaO_{12}S_3$ [M+Na]$^+$ m/z 570.0497. found 570.0493.

5-(Bis(2-bromoethyl)amino)-N-(2-hydroxyethyl)-4-(methylsulfonyl)-2-nitrobenzamide (301)

((5-((2-Hydroxyethyl)carbamoyl)-2-(methylsulfonyl)-4-nitrophenyl)azanediyl)bis(ethane-2,1-diyl) dimethanesulfonate 304 (3.40 g, 6.21 mmol) was dissolved in acetone (180 mL) and treated with LiBr (10.78 g, 124.18 mmol) at the room temperature. The reaction mixture was stirred overnight and the solvent was removed. The residue was dissolved in EtOAc and washed with water (2×), dried with $Na_2SO_4$ and concentrated under reduced pressure. The crude product was purified by flash column chromatography on silica gel eluting with $CH_2Cl_2$/MeOH (20:1) and further recrystallized from $CH_2Cl_2$/MeOH (4:1) and $iPr_2O$ to give 5-(bis(2-bromoethyl)amino)-N-(2-hydroxyethyl)-4-(methylsulfonyl)-2-nitrobenzamide 28 (3.06 g, 95%) as a pale yellow solid. M.p. and $^1$HNMR identical to that previously reported (Denny et al, WO2005/042471A1).

2-(5-(bis(2-bromoethyl)amino)-N-methyl-4-(methylsulfonyl)-2-nitrobenzamido)ethyl dihydrogen phosphate (10)

2-(5-(Bis(2-bromoethyl)amino)-N-methyl-4-(methylsulfonyl)-2-nitrobenzamido)ethyl di-tert-butyl phosphate (122)

A solution of 5-(Bis(2-bromoethyl)amino)-N-(2-hydroxyethyl)-N-methyl-4-(methylsulfonyl)-2-nitrobenzamide 14 (3.13 g, 5.89 mmol) in DMF (4.2 mL) and 1H-tetrazole solution (3%, 1.90 g, 27.10 mmol) in $CH_3CN$ was treated with di-tert-butyl-N,N-diisopropylphosphoramidite (7.44 mL, 23.56 mmol) at 5° C. The reaction mixture was stirred for 4 h at the room temperature, diluted with $CH_2Cl_2$ (25 mL), cooled to 0° C. and solid m-CPBA (70%, 7.78 g, 44.18 mmol) added portionwise. The mixture was warmed to the room temperature, stirred for further 1 h and the solvents were removed under reduced pressure. The residue was dissolved in EtOAc, washed with 10% solution of sodium disulfite (2×) and 5% solution of sodium bicarbonate (3×), dried with $Na_2SO_4$ and concentrated under reduced pressure. The crude product was purified by flash column chromatography on silica gel eluting with $CH_2Cl_2$/MeOH (25:1) to give 2-(5-(bis(2-bromoethyl)amino)-N-methyl-4-(methylsulfonyl)-2-nitrobenzamido)ethyl di-tert-butyl phosphate 122 (3.23 g, 76%) as a mixture of atropisomers, as a yellow gum. $^1$HNMR [$(CD_3)_2SO$] δ 8.67 (s, 0.5H), 8.66 (s, 0.5H), 7.78 (s, 0.5H), 7.60 (s, 0.5H), 4.15-4.02 (m, 2H), 3.85-3.81 (m, 4H), 3.78-3.66 (m, 2H), 3.64-3.61 (m, 4H), 3.49 (s, 3H), 3.07 (s, 1.5H), 2.89 (s, 1.5H), 1.44 (s, 10H), 1.40 (s, 8H). HRMS (ESI) calcd for $C_{23}H_{38}Br_2N_3NaO_9PS$ [M+Na]$^+$ m/z 744.0301. found 744.0325.

2-(5-(Bis(2-bromoethyl)amino)-N-methyl-4-(methylsulfonyl)-2-nitrobenzamido)ethyl dihydrogen phosphate (10)

2-(5-(Bis(2-bromoethyl)amino)-N-methyl-4-(methylsulfonyl)-2-nitrobenzamido)ethyl di-tert-butyl phosphate 122 (3.23 g, 4.46 mmol) in $CH_2Cl_2$ (17 mL) was cooled to 5° C. and treated with TFA (17 mL). The reaction mixture was stirred for 1 h at the room temperature, and the solvents were removed under reduced pressure. The residue was triturated with $CH_2Cl_2$/$iPr_2O$ then dissolved in $CH_3CN$. The solvent was removed under reduced pressure (water bath 29° C.) to provide 2-(5-(bis(2-bromoethyl)amino)-N-methyl-4-(methylsulfonyl)-2-nitrobenzamido)ethyl dihydrogen phosphate 10 (2.72 g, 100%) as a mixture of atropisomers, as a yellow gum. $^1$HNMR [$(CD_3)_2SO$] δ8.66 (s, 0.5H), 8.65 (s, 0.5H), 7.78 (s, 0.5H), 7.63 (s, 0.5H), 4.11-4.06 (m, 2H), 3.84-3.81 (m, 4H), 3.78-3.65 (m, 2H), 3.61-3.58 (m, 4H), 3.46 (s, 3H), 3.04 (s, 1.5H), 2.86 (s, 1.5H). HRMS(ESI) calcd for $C_{15}H_{22}Br_2N_3NaO_9PS$ [M+Na]$^+$ m/z 631.9065. found 631.9073.

2-(5-(bis(2-bromoethyl)amino)-4-(ethylsulfonyl)-N-methyl-2-nitrobenzamido)ethyl dihydrogen phosphate (11)

2-(5-(Bis(2-bromoethyl)amino)-N-methyl-4-(ethylsulfonyl)-2-nitrobenzamido)ethyl di-tert-butyl phosphate (123)

A solution of 5-(bis(2-bromoethyl)amino)-N-(2-hydroxyethyl)-N-methyl-4-(ethylsulfonyl)-2-nitrobenzamide 18 (1.80 g, 3.30 mmol) in DMF (2.0 mL) and 1H-tetrazole solution (3%, 1.06 g, 15.18 mmol) in $CH_3CN$ was treated with di-tert-butyl-N,N-diisopropylphosphoramidite (4.16 mL, 13.20 mmol) at 5° C. The reaction mixture was stirred for 4 h at the room temperature, diluted with $CH_2Cl_2$ (15 mL), cooled to 0° C. and solid m-CPBA (70%, 4.36 g, 24.75 mmol) added portionwise. The mixture was warmed to the room temperature, stirred for further 1 h and the solvents were removed under reduced pressure. The residue was dissolved in EtOAc, washed with 10% solution of sodium disulfite (2×) and 5% solution of sodium bicarbonate (3×), dried with $Na_2SO_4$ and concentrated under reduced pressure. The crude product was purified by flash column chromatography on silica gel eluting with $CH_2Cl_2$/MeOH (25:1) to give 2-(5-(bis(2-bromoethyl)amino)-N-methyl-4-(ethylsulfonyl)-2-nitrobenzamido)ethyl di-tert-butyl phosphate 123 (2.16 g, 89%) as a mixture of atropisomers, as a yellow gum. $^1$HNMR [$(CD_3)_2SO$] δ 8.65 (s, 0.5H), 8.64 (s, 0.5H), 7.77 (s, 0.5H), 7.59 (s, 0.5H), 4.14-4.11 (m, 2H), 3.84-3.81 (m, 5H), 3.74-3.66 (m, 3H), 3.63-3.60 (m, 4H), 3.07 (s, 1.5H), 2.89 (s, 1.5H), 1.44 (s, 10H), 1.40 (s, 8H), 1.10 (t, J=7.3 Hz, 3H). HRMS(ESI) calcd for $C_{24}H_{40}Br_2N_3NaO_9PS$ [M+Na]$^+$ m/z 758.0469. found 758.0440.

2-(5-(bis(2-bromoethyl)amino)-4-(ethylsulfonyl)-N-methyl-2-nitrobenzamido)ethyl dihydrogen phosphate (11)

2-(5-(Bis(2-bromoethyl)amino)-N-methyl-4-(ethylsulfonyl)-2-nitrobenzamido)ethyl di-tert-butyl phosphate 123 (2.16 g, 2.93 mmol) in $CH_2Cl_2$ (25 mL) was cooled to 5° C.

and treated with TFA (5 mL). The reaction mixture was stirred for 1 h at the room temperature, and the solvents were removed under reduced pressure (water bath 29° C.). The gum was then triturated with iPr$_2$O to provide 2-(5-(bis(2-bromoethyl)amino)-4-(ethylsulfonyl)-N-methyl-2-nitrobenzamido)ethyl dihydrogen phosphate 11 (1.59 g, 87%) as a mixture of atropisomers, as a yellow gum. $^1$HNMR [(CD$_3$)$_2$SO] δ 8.65 (s, 0.6H), 8.64 (s, 0.4H), 7.76 (s, 0.5H), 7.62 (s, 0.5H), 4.10-3.99 (m, 2H), 3.84-3.80 (m, 4H), 3.74-3.68 (m, 3H), 3.63-3.57 (m, 5H), 3.06 (s, 1.4H), 2.89 (s, 1.6H), 1.12-1.08 (m, 3H). Anal. calcd for C$_{16}$H$_{24}$Br$_2$N$_3$O$_9$PS. (0.25iPr$_2$O+0.1CH$_2$Cl$_2$): C, 32.10; H, 4.16; N, 6.38; P, 4.70%. found: C, 32.36; H, 4.09; N, 6.13; P, 4.34%.

2-(5-(Bis(2-bromoethyl)amino)-4-(methylsulfonyl)-2-nitrobenzamido)ethyl dihydrogen phosphate (300)

2-(5-(Bis(2-bromoethyl)amino)-4-(methylsulfonyl)-2-nitrobenzamido)ethyl di-tert-butyl phosphate (302)

A solution of 5-(bis(2-bromoethyl)amino)-N-(2-hydroxyethyl)-4-(methylsulfonyl)-2-nitrobenzamide 301 (3.00 g, 5.80 mmol) in DMF (4.1 mL) and 1H-tetrazole solution (3%, 1.87 g, 26.68 mmol) in CH$_3$CN was treated with di-tert-butyl-N,N-diisopropylphosphoramidite (7.32 mL, 23.20 mmol) at 5° C. The reaction mixture was stirred for 4 h at the room temperature, diluted with CH$_2$Cl$_2$ (25 mL), cooled to 0° C. and solid m-CPBA (70%, 10.22 g, 58.00 mmol) added portionwise. The mixture was warmed to the room temperature, stirred for further 1 h and the solvents were removed under reduced pressure. The residue was dissolved in EtOAc, washed with 10% solution of sodium disulfite (2×) and 5% solution of sodium bicarbonate (3×), dried with Na$_2$SO$_4$ and concentrated under reduced pressure. The crude product was purified by flash column chromatography on silica gel eluting with CH$_2$Cl$_2$/MeOH (25:1) to give 2-(5-(bis(2-bromoethyl)amino)-4-(methylsulfonyl)-2-nitrobenzamido)ethyl di-tert-butyl phosphate 302 (2.78 g, 68%) as a yellow gum. $^1$HNMR [(CD$_3$)$_2$SO] δ 8.94 (t, J=5.6 Hz, 1H), 8.53 (s, 1H), 7.73 (s, 1H), 4.00-3.96 (m, 2H), 3.77-3.74 (m, 4H), 3.64-3.61 (m, 4H), 3.52-3.48 (m, 2H), 3.50 (s, 3H), 1.43 (s, 18H). HRMS(ESI) calcd for C$_{22}$H$_{36}$Br$_2$N$_3$NaO$_9$PS [M+Na]$^+$ m/z 730.0163. found 730.0169.

2-(5-(Bis(2-bromoethyl)amino)-4-(methylsulfonyl)-2-nitrobenzamido)ethyl dihydrogen phosphate (300)

2-(5-(Bis(2-bromoethyl)amino)-4-(methylsulfonyl)-2-nitrobenzamido)ethyl di-tert-butyl phosphate 302 (2.70 g, 3.81 mmol) in CH$_2$Cl$_2$ (14 mL) was cooled to 5° C. and treated with TFA (14 mL). The reaction mixture was stirred for 1 h at the room temperature, and the solvents were removed under reduced pressure. The residue was triturated with CH$_2$Cl$_2$/iPr$_2$O then dissolved in CH$_3$CN. The solvent was removed under reduced pressure (water bath 29° C.) to provide 2-(5-(bis(2-bromoethyl)amino)-4-(methylsulfonyl)-2-nitrobenzamido)ethyl dihydrogen phosphate 300 (2.27 g, 100%) as a yellow gum. $^1$HNMR [(CD$_3$)$_2$SO] δ 8.93 (t, J=5.8 Hz, 1H), 8.52 (s, 1H), 7.76 (s, 1H), 3.98-3.93 (m, 2H), 3.77-3.74 (m, 4H), 3.64-3.61 (m, 4H), 3.50-3.45 (m, 2H), 3.50 (s, 3H). HRMS(ESI) calcd for C$_{14}$H$_{20}$Br$_2$N$_3$NaO$_9$PS [M+Na]$^+$ m/z 617.8899. found 617.8917.

(5-(Bis(2-bromoethyl)amino)-4-(methylsulfonyl)-2-nitrophenyl)(4-methylpiperazine-1-yl)methanone (22)

((5-(4-methylpiperazine-1-carbonyl)-2-(methylsulfonyl)-4-nitrophenyl)azanediyl)bis(ethane-2,1-diyl) dimethanesulfonate (124)

A solution of 5-(bis(2-((methylsulfonyl)oxy)ethyl)amino)-4-(methylsulfonyl)-2-nitrobenzoic acid 109 (770 mg, 1.53 mmol) in CH$_2$Cl$_2$ (20 mL) and CH$_3$CN (4 mL) was treated with MgO (1.23 g, 30.52 mmol) at the room temperature then cooled to 0° C. and treated with oxalyl chloride (786 μL, 9.16 mmol) and DMF (3 drops). The reaction mixture was stirred at 0° C. for 1 h then warmed to the room temperature for 4 h. The mixture was filtered through a short pad of Celite and the solvents were removed under reduced pressure. The residue was dissolved in CH$_2$Cl$_2$ (20 mL) and THF (20 mL), cooled to 0° C. and treated with 1-methylpiperazine (459 mg, 4.58 mmol) and warm to the room temperature for 30 min. The mixture was washed with water (3×), dried with Na$_2$SO$_4$ and concentrated under reduced pressure. The residues was purified by flash column chromatography on silica gel eluting with CH$_2$Cl$_2$/MeOH (19:1) to give ((5-(4-methylpiperazine-1-carbonyl)-2-(methylsulfonyl)-4-nitrophenyl)azanediyl)bis(ethane-2,1-diyl)dimethanesulfonate 124 (600 mg, 67%) as a yellow gum. $^1$HNMR [(CD$_3$)$_2$SO] δ 8.65 (s, 1H), 7.68 (s, 1H), 4.34 (t, J=5.1 Hz, 4H), 3.79-3.78 (m, 5H), 3.49 (br, 1H), 3.44 (s, 3H), 3.24-3.17 (m, 2H), 3.14 (s, 6H), 2.33 (br, 3H) 2.20 (s, 3H), 2.09 (br, 1H). HRMS (ESI) calcd for C$_{19}$H$_{31}$N$_4$O$_{11}$S$_3$[M+H]$^+$ m/z 587.1146. found 587.1148.

(5-(bis(2-bromoethyl)amino)-4-(methylsulfonyl)-2-nitrophenyl)(4-methylpiperazine-1-yl)methanone (22)

((5-(4-Methylpiperazine-1-carbonyl)-2-(methylsulfonyl)-4-nitrophenyl)azanediyl)bis(ethane-2,1-diyl) dimethanesulfonate 124 (1.2 g, 2.05 mmol) was dissolved in acetone (40 mL) and treated with LiBr (3.55 g, 40.91 mmol) at the room temperature. The reaction mixture was stirred overnight and the solvent was removed. The residue was dissolved in EtOAc and washed with water (2×), dried with Na$_2$SO$_4$ and concentrated under reduced pressure. The crude product was purified by flash column chromatography on silica gel eluting with CH$_2$Cl$_2$/MeOH (20:1) to give (5-(bis(2-bromoethyl)amino)-4-(methylsulfonyl)-2-nitrophenyl)(4-methylpiperazine-1-yl)methanone 22 (1.01 g, 89%) as a yellow gum. $^1$HNMR [(CD$_3$)$_2$SO] δ 8.65 (s, 1H), 7.69 (s, 1H), 3.85-3.80 (m, 4H), 3.78-3.69 (m, 2H), 3.62 (t, J=6.8 Hz, 4H), 3.58-3.51 (m, 1H), 3.48 (s, 3H), 3.23-3.17 (m, 2H), 2.46-2.29 (m, 2H), 2.21 (s, 3H), 2.13 (br, 1H). HRMS(ESI) calcd for C$_{17}$H$_{24}$Br$_2$KN$_4$O$_5$S [M+K]$^+$ m/z 592.9466. found 592.9474.

(5-(bis(2-bromoethyl)amino)-4-(methylsulfonyl)-2-nitrophenyl)(4-ethylpiperazine-1-yl)methanone (23)

(5-(bis(2-chloroethyl)amino)-4-(methylsulfonyl)-2-nitrophenyl)(4-ethylpiperazine-1-yl)methanone (131)

A stirred solution of 5-(bis(2-hydroxyethyl)amino)-4-(methylsulfonyl)-2-nitrobenzoic acid 104 (1.62 g, 4.65 mmol) in SOCl$_2$ (40 mL) and DMF (3 drops) was heated under reflux for 4 h. The excess SOCl$_2$ was removed by distillation under reduced pressure and the residue was dissolved in CH$_2$Cl$_2$ (32 mL) and THF (32 mL), cooled to 0° C. and treated with 1-ethylpiperazine (1.60 g, 14.01 mmol) and warm to the room temperature for 30 min. The mixture was washed with water (3×), dried with Na$_2$SO$_4$ and concentrated under reduced pressure. The residues was purified by flash column chromatography on silica gel eluting with CH$_2$Cl$_2$/MeOH (19:1) to give (5-(bis(2-chloroethyl)amino)-4-(methylsulfonyl)-2-nitrophenyl)(4-ethylpiperazine-1-yl)methanone 131 (1.12 g, 50%) as a yellow gum. $^1$HNMR [(CD$_3$)$_2$SO] δ 8.65 (s, 1H), 7.68 (s, 1H), 3.78-3.77 (m, 8H), 3.69 (br, 1H), 3.58 (br, 1H), 3.47 (s, 3H), 3.17 (br, 2H), 2.42 (br, 1H), 2.39-2.33 (m, 3H), 2.25-1.98 (m, 1H), 1.02-0.98 (t, J=7.2 Hz, 3H). HRMS(ESI) calcd for C$_{18}$H$_{27}$Cl$_2$N$_4$O$_5$S [M+H]$^+$ m/z 481.1074. found 481.1073.

(5-(bis(2-bromoethyl)amino)-4-(methylsulfonyl)-2-nitrophenyl)(4-ethylpiperazine-1-yl)methanone (23)

A solution of (5-(bis(2-chloroethyl)amino)-4-(methylsulfonyl)-2-nitrophenyl)(4-ethylpiperazine-1-yl)methanone 131 (4.50 g, 9.37 mmol) in 3-methyl-2-butanone (200 ml) was treated with LiBr (16.28 g, 187.46 mmol) and heated to reflux overnight. The reaction mixture was cooled to the room temperature and the solvent was removed under reduced pressure. The residue was dissolved in EtOAc and washed with water (3×), dried with Na$_2$SO$_4$ and concentrated under reduced pressure. The crude mixture was resubmitted to LiBr (2×) and worked up as above. The final product was purified by flash column chromatography on silica gel eluting with CH$_2$Cl$_2$/MeOH (20:1) to give (5-(bis(2-bromoethyl)amino)-4-(methylsulfonyl)-2-nitrophenyl)(4-ethylpiperazine-1-yl)methanone 23 (1.92 g, 36%) as a yellow gum. $^1$HNMR [(CD$_3$)$_2$SO] δ 8.65 (s, 1H), 7.69 (s, 1H), 3.83 (q, J=7.4 Hz, 4H), 3.74-3.67 (m, 1H), 3.64-3.54 (m, 6H), 3.48 (s, 3H), 3.23-3.16 (m, 2H), 2.46-2.40 (m, 1H), 2.39-2.32 (m, 3H), 2.25-1.98 (m, 1H), 1.02-0.98 (t, J=7.2 Hz, 3H). HRMS (ESI) calcd for C$_{18}$H$_{27}$Br$_2$N$_4$O$_5$S [M+H]$^+$ m/z 569.0063. found 569.0042.

(5-(bis(2-bromoethyl)amino)-4-(methylsulfonyl)-2-nitrophenyl)(4-isopropylpiperazine-1-yl)methanone (24)

(5-(bis(2-chloroethyl)amino)-4-(methylsulfonyl)-2-nitrophenyl)(4-isopropylpiperazine-1-yl)methanone (132)

A stirred solution of 5-(bis(2-hydroxyethyl)amino)-4-(methylsulfonyl)-2-nitrobenzoic acid 104 (1.09 g, 3.13 mmol) in SOCl$_2$ (30 mL) and DMF (3 drops) was heated under reflux for 4 h. The excess SOCl$_2$ was removed by distillation under reduced pressure and the residue was dissolved in CH$_2$Cl$_2$ (20 mL) and THF (20 mL), cooled to 0° C. and treated with 1-isopropylpiperazine (1.20 g, 9.39 mmol) and warm to the room temperature for 30 min. The mixture was washed with water (3×), dried with Na$_2$SO$_4$ and concentrated under reduced pressure. The residues was purified by flash column chromatography on silica gel eluting with CH$_2$Cl$_2$/MeOH (19:1) to give (5-(bis(2-chloroethyl)amino)-4-(methylsulfonyl)-2-nitrophenyl)(4-isopropylpiperazine-1-yl)methanone 132 (1.06 g, 69%) as a yellow gum. $^1$HNMR [(CD$_3$)$_2$SO] δ 8.65 (s, 1H), 7.68 (s, 1H), 3.78-3.77 (m, 8H), 3.68 (br, 1H), 3.56 (br, 1H), 3.47 (s, 3H), 3.16 (br, 2H), 2.74-2.65 (m, 1H), 2.57 (br, 2H), 2.39 (br, 1H), 2.34-2.26 (m, 1H), 0.99 (d, J=6.5 Hz, 6H). HRMS(ESI) calcd for C$_{19}$H$_{29}$Cl$_2$N$_4$O$_5$S [M+H]$^+$ m/z 495.1230. found 495.1217.

(5-(bis(2-bromoethyl)amino)-4-(methylsulfonyl)-2-nitrophenyl)(4-isopropylpiperazine-1-yl)methanone (24)

A solution of (5-(bis(2-chloroethyl)amino)-4-(methylsulfonyl)-2-nitrophenyl)(4-isopropylpiperazine-1-yl)methanone 132 (1.06 g, 2.15 mmol) in 3-methyl-2-butanone (100 ml) was treated with LiBr (3.73 g, 42.90 mmol) and heated to reflux overnight. The reaction mixture was cooled to the room temperature and the solvent was removed under reduced pressure. The residue was dissolved in EtOAc and washed with water (3×), dried with Na$_2$SO$_4$ and concentrated under reduced pressure. The crude mixture was resubmitted to LiBr (2×) and worked up as above. The final product was purified by flash column chromatography on silica gel eluting with CH$_2$Cl$_2$/MeOH (20:1) to give (5-(bis(2-bromoethyl)amino)-4-(methylsulfonyl)-2-nitrophenyl)(4-isopropylpiperazine-1-yl)methanone 24 (660 mg, 53%) as a yellow gum. $^1$HNMR [(CD$_3$)$_2$SO] δ 8.65 (s, 1H), 7.69 (s, 1H), 3.83 (q, J=7.0 Hz, 4H), 3.67-3.53 (m, 6H), 3.50 (s, 3H), 3.18 (br, 2H), 2.73-2.67 (m, 1H), 2.60-2.52 (m, 1H), 2.47-2.40 (m, 1H), 2.33-2.23 (m, 1H), 2.15-2.06 (m, 1H), 0.97 (d, J=6.5 Hz, 6H). HRMS(ESI) calcd for C$_{19}$H$_{29}$Br$_2$N$_4$O$_5$S [M+H]$^+$ m/z 583.0220. found 583.0203.

(5-(bis(2-bromoethyl)amino)-4-(ethylsulfonyl)-2-nitrophenyl)(4-methylpiperazine-1-yl)methanone (25)

((5-(4-methylpiperazine-1-carbonyl)-2-(ethylsulfonyl)-4-nitrophenyl)azanediyl)bis(ethane-2,1-diyl) dimethanesulfonate (133)

A solution of 5-(bis(2-((methylsulfonyl)oxy)ethyl)amino)-4-(ethylsulfonyl)-2-nitrobenzoic acid 119 (2.33 g, 4.49 mmol) in CH$_2$Cl$_2$ (60 mL) and CH$_3$CN (12 mL) was treated with MgO (3.59 g, 89.87 mmol) at the room temperature then cooled to 0° C. and treated with oxalyl chloride (2.31 mL, 26.96 mmol) and DMF (3 drops). The reaction mixture was stirred at 0° C. for 1 h then warmed to the room temperature for 4 h. The mixture was filtered through a short pad of Celite and the solvents were removed under reduced pressure. The residue was dissolved in CH$_2$Cl$_2$ (60 mL) and THF (60 mL), cooled to 0° C. and treated with 1-methylpiperazine (1.35 g, 13.48 mmol) and warm to the room temperature for 30 min. The mixture was washed with water (3×), dried with Na$_2$SO$_4$ and concentrated under reduced pressure. The residues was purified by flash column chromatography on silica gel eluting with CH$_2$Cl$_2$/MeOH (19:1) to give ((5-(4-methylpiperazine-1-carbonyl)-2-(ethylsulfonyl)-4-nitrophenyl)azanediyl)bis(ethane-2,1-diyl)dimethanesulfonate 133 (1.78 g, 66%) as a yellow gum. $^1$HNMR [(CD$_3$)$_2$SO] δ 8.63 (s, 1H), 7.67 (s, 1H), 4.36-4.33 (m, 4H), 3.80-3.76 (m, 6H), 3.66-3.60 (m, 3H), 3.48 (br, 2H), 3.22-3.17 (m, 2H), 3.15 (s, 6H), 2.20 (s, 3H), 2.13 (br, 1H), 1.10 (t, J=7.4 Hz, 3H). HRMS(ESI) calcd for C$_{20}$H$_{33}$N$_4$O$_{11}$S$_3$ [M+H]$^+$ m/z 601.1302. found 601.1299.

(5-(bis(2-bromoethyl)amino)-4-(ethylsulfonyl)-2-nitrophenyl)(4-methylpiperazine-1-yl)methanone (25)

((5-(4-Methylpiperazine-1-carbonyl)-2-(ethylsulfonyl)-4-nitrophenyl)azanediyl)bis(ethane-2,1-diyl)dimethanesulfonate 133 (1.78 g, 2.96 mmol) was dissolved in acetone (70 mL) and treated with LiBr (5.15 g, 59.27 mmol) at the room temperature. The reaction mixture was stirred overnight and the solvent was removed. The residue was dissolved in EtOAc and washed with water (2×), dried with $Na_2SO_4$ and concentrated under reduced pressure. The crude product was purified by flash column chromatography on silica gel eluting with $CH_2Cl_2$/MeOH (20:1) to give (5-(bis(2-bromoethyl)amino)-4-(ethylsulfonyl)-2-nitrophenyl)(4-methylpiperazine-1-yl)methanone 25 (1.44 g, 85%) as a yellow gum. $^1$HNMR [$(CD_3)_2SO$] δ 8.63 (s, 1H), 7.68 (s, 1H), 3.85-3.80 (m, 4H), 3.72-3.66 (m, 3H), 3.63-3.59 (m, 5H), 3.19 (br, 2H), 2.46-2.29 (m, 3H), 2.21 (s, 3H), 2.17 (br, 1H), 1.11 (t, J=7.4 Hz, 3H). HRMS(ESI) calcd for $C_{18}H_{26}Br_2KN_4O_{2.5}S$ [M+K]$^+$ m/z 606.9622. found 606.9615.

(5-(bis(2-bromoethyl)amino)-4-(ethylsulfonyl)-2-nitrophenyl)(4-ethylpiperazine-1-yl)methanone (26)

((5-(4-ethylpiperazine-1-carbonyl)-2-(ethylsulfonyl)-4-nitrophenyl)azanediyl)bis(ethane-2,1-diyl)dimethanesulfonate (134)

A solution of 5-(bis(2-((methylsulfonyl)oxy)ethyl)amino)-4-(ethylsulfonyl)-2-nitrobenzoic acid 119 (1.96 g, 3.78 mmol) in $CH_2Cl_2$ (50 mL) and $CH_3CN$ (10 mL) was treated with MgO (3.02 g, 75.60 mmol) at the room temperature then cooled to 0° C. and treated with oxalyl chloride (1.95 mL, 22.68 mmol) and DMF (3 drops). The reaction mixture was stirred at 0° C. for 1 h then warmed to the room temperature for 4 h. The mixture was filtered through a short pad of Celite and the solvents were removed under reduced pressure. The residue was dissolved in $CH_2Cl_2$ (50 mL) and THF (50 mL), cooled to 0° C. and treated with 1-ethylpiperazine (1.29 g, 11.34 mmol) and warm to the room temperature for 30 min. The mixture was washed with water (3×), dried with $Na_2SO_4$ and concentrated under reduced pressure. The residues was purified by flash column chromatography on silica gel eluting with $CH_2Cl_2$/MeOH (19:1) to give ((5-(4-ethylpiperazine-1-carbonyl)-2-(ethylsulfonyl)-4-nitrophenyl)azanediyl)bis(ethane-2,1-diyl)dimethanesulfonate 134 (1.14 g, 49%) as a yellow gum. $^1$HNMR [$(CD_3)_2SO$] δ 8.63 (s, 1H), 7.67 (s, 1H), 4.34-4.33 (m, 4H), 3.80-3.76 (m, 5H), 3.66-3.60 (m, 2H), 3.49 (br, 2H), 3.22-3.17 (m, 2H), 3.15 (s, 6H), 2.39-2.32 (m, 4H), 2.18 (br, 1H), 1.09 (t, J=7.4 Hz, 3H), 1.00 (t, J=7.2 Hz, 3H). HRMS(ESI) calcd for $C_{21}H_{35}N_4O_{11}S_3$ [M+H]$^+$ m/z 615.1459. found 615.1464.

(5-(bis(2-bromoethyl)amino)-4-(ethylsulfonyl)-2-nitrophenyl)(4-ethylpiperazine-1-yl)methanone (26)

((5-(4-Ethylpiperazine-1-carbonyl)-2-(ethylsulfonyl)-4-nitrophenyl)azanediyl)bis(ethane-2,1-diyl)dimethanesulfonate 134 (1.14 g, 1.85 mmol) was dissolved in acetone (45 mL) and treated with LiBr (5.15 g, 37.09 mmol) at the room temperature. The reaction mixture was stirred overnight and the solvent was removed. The residue was dissolved in EtOAc and washed with water (2×), dried with $Na_2SO_4$ and concentrated under reduced pressure. The crude product was purified by flash column chromatography on silica gel eluting with $CH_2Cl_2$/MeOH (20:1) to give (5-(bis(2-bromoethyl)amino)-4-(ethylsulfonyl)-2-nitrophenyl)(4-ethylpiperazine-1-yl)methanone 26 (915 mg, 85%) as a yellow gum. $^1$HNMR [$(CD_3)_2SO$] δ 8.63 (s, 1H), 7.68 (s, 1H), 3.84-3.80 (m, 4H), 3.77-3.66 (m, 4H), 3.63-3.59 (m, 5H), 3.19 (br, 2H), 2.42 (br, 1H), 2.39-2.32 (m, 3H), 2.21 (br, 1H), 1.11 (t, J=7.4 Hz, 3H), 1.00 (t, J=7.2 Hz, 3H). HRMS(ESI) calcd for $C_{19}H_{29}Br_2N_4O_5S$ [M+H]$^+$ m/z 583.0220. found 583.0221.

(5-(bis(2-bromoethyl)amino)-4-(ethylsulfonyl)-2-nitrophenyl)(4-isopropylpiperazine-1-yl)methanone (27)

((5-(4-isopropylpiperazine-1-carbonyl)-2-(ethylsulfonyl)-4-nitrophenyl)azanediyl)bis(ethane-2,1-diyl) dimethanesulfonate (135)

A solution of 5-(bis(2-((methylsulfonyl)oxy)ethyl)amino)-4-(ethylsulfonyl)-2-nitrobenzoic acid 119 (2.00 g, 3.85 mmol) in $CH_2Cl_2$ (50 mL) and $CH_3CN$ (12 mL) was treated with MgO (3.08 g, 77.14 mmol) at the room temperature then cooled to 0° C. and treated with oxalyl chloride (1.99 mL, 23.14 mmol) and DMF (3 drops). The reaction mixture was stirred at 0° C. for 1 h then warmed to the room temperature for 4 h. The mixture was filtered through a short pad of Celite and the solvents were removed under reduced pressure. The residue was dissolved in $CH_2Cl_2$ (50 mL) and THF (50 mL), cooled to 0° C. and treated with 1-isopropylpiperazine (1.48 g, 11.57 mmol) and warm to the room temperature for 30 min. The mixture was washed with water (3×), dried with $Na_2SO_4$ and concentrated under reduced pressure. The residues was purified by flash column chromatography on silica gel eluting with $CH_2Cl_2$/MeOH (19:1) to give ((5-(4-isopropylpiperazine-1-carbonyl)-2-(ethylsulfonyl)-4-nitrophenyl)azanediyl)bis(ethane-2,1-diyl)dimethanesulfonate 135 (1.21 g, 49%) as a yellow gum. $^1$HNMR [$(CD_3)_2SO$] δ 8.63 (s, 1H), 7.67 (s, 1H), 4.34-4.33 (m, 4H), 3.78-3.77 (m, 5H), 3.66-3.60 (m, 2H), 3.53-3.45 (m, 1H), 3.20 (br, 2H), 3.16 (s, 6H), 2.73-2.66 (m, 1H), 2.58 (br, 1H), 2.45-2.25 (m, 3H), 1.09 (t, J=7.4 Hz, 3H), 0.97 (d, J=6.5 Hz, 6H). HRMS(ESI) calcd for $C_{22}H_{37}N_4O_{11}S_3$[M+H]$^+$ m/z 629.1615. found 629.1612.

(5-(bis(2-bromoethyl)amino)-4-(ethylsulfonyl)-2-nitrophenyl)(4-isopropylpiperazine-1-yl)methanone (27)

((5-(4-Isopropylpiperazine-1-carbonyl)-2-(ethylsulfonyl)-4-nitrophenyl)azanediyl)bis(ethane-2,1-diyl)dimethanesulfonate 135 (1.16 g, 2.58 mmol) was dissolved in acetone (45 mL) and treated with LiBr (3.06 g, 35.22 mmol) at the room temperature. The reaction mixture was stirred overnight and the solvent was removed. The residue was dissolved in EtOAc and washed with water (2×), dried with $Na_2SO_4$ and concentrated under reduced pressure. The crude product was purified by flash column chromatography on silica gel eluting with $CH_2Cl_2$/MeOH (20:1) to give (5-(bis(2-bromoethyl)amino)-4-(ethylsulfonyl)-2-nitrophenyl)(4-isopropylpiperazine-1-yl)methanone 27 (934 mg, 85%) as a yellow gum. $^1$HNMR [$(CD_3)_2SO$] δ 8.63 (s, 1H), 7.68 (s, 1H), 3.84-3.81 (m, 4H), 3.77-3.66 (m, 3H), 3.63-3.53 (m, 5H), 3.18 (br, 2H), 2.73-2.67 (m, 1H), 2.57 (br, 2H), 2.40 (br, 1H), 2.31 (br, 1H), 1.10 (t, J=7.4 Hz, 3H), 0.97 (d, J=6.5 Hz, 6H). HRMS(ESI) calcd for $C_{20}H_{31}Br_2N_4O_{2.5}S$ [M+H]$^+$ m/z 597.0376. found 597.0394.

2-((2-bromoethyl)(2-((2-hydroxyethyl)carbamoyl)-4-nitrophenyl)amino)ethyl methanesulfonate (64)

2-fluoro-5-nitro-N-(2-((tetrahydro-2H-pyran-2-yl)oxy)ethyl) benzamide (126)

Method 1

A stirred solution of 2-fluoro-5-nitrobenzoic acid 125 (4.56 g, 24.63 mmol) in $SOCl_2$ (50 mL) and DMF (3 drops) was heated under reflux for 4 h. The excess $SOCl_2$ was removed by distillation under reduced pressure and the residue was dissolved in THF (30 mL), cooled to −10° C. and treated with 2-((tetrahydro-2H-pyran-2-yl)oxy)ethanamine (3.93 g, 27.10 mmol) and warm to the room temperature for 30 min. The solvent was evaporated and the residue was dissolved in EtOAc, washed with water (3×) and brine, dried with $Na_2SO_4$ and concentrated under reduced pressure. The crude product was purified by flash column chromatography on silica gel eluting with EtOAc/Hexane (1:1) to give 2-fluoro-5-nitro-N-(2-((tetrahydro-2H-pyran-2-yl)oxy)ethyl) benzamide 126 (3.17 g, 41%) as a colorless oil. $^1$HNMR [$(CD_3)_2SO$] δ 8.67 (br, 1H), 8.42-8.38 (m, 2H), 7.64-7.59 (m, 1H), 4.62 (t, J=3.5 Hz, 1H), 3.55-3.41 (m, 5H), 1.79-1.70 (m, 1H), 1.66-1.60 (m, 1H), 1.53-1.41 (m, 5H). HRMS(ESI) calcd for $C_{14}H_{17}FN_2NaO_{25}$ [M+Na]$^+$ m/z 335.1014. found 335.1014.

Method 2

A stirred solution of 2-fluoro-5-nitrobenzoic acid 125 (15.0 g, 81.08 mmol) in $SOCl_2$ (160 mL) and DMF (3 drops) was heated under reflux for 4 h. The excess $SOCl_2$ was removed by distillation under reduced pressure and the residue was dissolved in THF (100 mL), cooled to −10° C. and treated with ethanolamine (8.53 mL, 141.81 mmol) and warm to the room temperature for 30 min. The solvent was evaporated and the residue was dissolved in EtOAc, washed with water (3×) and brine, dried with $Na_2SO_4$ and concentrated under reduced pressure. The crude product was purified by flash column chromatography on silica gel eluting with EtOAc/Hexane (2:1) to give 2-fluoro-N-(2-hydroxyethyl)-5-nitrobenzamide 136 (17.0 g, 92%) as a colorless gum. $^1$HNMR [$(CD_3)_2SO$] δ 8.58 (br, 1H), 8.46-8.44 (m, 1H), 8.41-8.31 (m, 1H), 7.60 (t, J=9.3 Hz, 1H), 4.79 (t, J=5.6 Hz, 1H), 3.55-3.50 (m, 2H), 3.35-3.32 (m, 2H).

2-Fluoro-N-(2-hydroxyethyl)-5-nitrobenzamide 136 (17.0 g, 74.50 mmol) was dissolved in $CH_2Cl_2$ (300 mL) and treated with catalytic amount of 4-methylbenzenesulfonic acid (1.28 g, 7.45 mmol) followed by 3,4-dihydro-2H-pyran (13.59 mL, 149.01 mmol) at the room temperature. The reaction mixture was stirred overnight then washed with water (3×), dried with $Na_2SO_4$ and concentrated under reduced pressure. The crude product was purified by flash column chromatography on silica gel eluting with EtOAc/Hexane (1:1) to give 2-fluoro-5-nitro-N-(2-((tetrahydro-2H-pyran-2-yl)oxy)ethyl) benzamide 126 (16.8 g, 72%) as a colorless oil. $^1$HNMR and HRMS in agreement with the Method 1.

2-(bis(2-hydroxyethyl)amino)-5-nitro-N-(2-((tetrahydro-2H-pyran-2-yl)oxy)ethyl) benzamide (127)

2-Fluoro-5-nitro-N-(2-((tetrahydro-2H-pyran-2-yl)oxy) ethyl) benzamide 126 (3.17 g, 10.15 mmol) was dissolved in dioxane (150 mL) and treated with $Et_3N$ (4.24 mL, 30.45 mmol) and diethanolamine (3.89 mL, 40.60 mmol). The reaction mixture was heated to 55° C. overnight then cooled to the room temperature, and the solvent was evaporated. The residue was dissolved in EtOAc, washed with water (3×) and brine, dried with $Na_2SO_4$ and concentrated under reduced pressure. The crude product was purified by flash column chromatography on silica gel eluting with EtOAc/Hexane (3:1) to give 2-(bis(2-hydroxyethyl)amino)-5-nitro-N-(2-((tetrahydro-2H-pyran-2-yl)oxy)ethyl) benzamide 127 (3.51 g, 87%) as a yellow gum. $^1$HNMR [$(CD_3)_2SO$] δ 8.71 (t, J=5.5 Hz, 1H), 8.10-8.06 (m, 2H), 7.17 (d, J=9.0 Hz, 1H), 4.73 (t, J=5.3 Hz, 2H), 4.62-4.60 (m, 1H), 3.80-3.72 (m, 2H), 3.57-3.49 (m, 5H), 3.47-3.40 (m, 7H), 1.77-1.70 (m, 1H), 1.66-1.61 (m, 1H), 1.50- 1.46 (m, 4H).

((4-nitro-2-((2-((tetrahydro-2H-pyran-2-yl)oxy) ethyl)carbamoyl)phenyl)azanediyl)bis(ethane-2,1-diyl) dimethanesulfonate (128)

A solution of 2-(bis(2-hydroxyethyl)amino)-5-nitro-N-(2-((tetrahydro-2H-pyran-2-yl)oxy)ethyl) benzamide 127 (6.01 g, 15.12 mmol) in $CH_2Cl_2$ (180 mL) was cooled to 0° C. and treated with $Et_3N$ (7.38 mL, 52.93 mmol) followed by methanesulfonyl chloride (4.40 mL, 45.36 mmol). The reaction mixture was warm to the room temperature for 30 min, washed with water (3×), dried with $Na_2SO_4$ and concentrated under reduced pressure. The residues was purified by flash column chromatography on silica gel eluting with $CH_2Cl_2$/MeOH (20:1) to give ((4-nitro-2-((2-((tetrahydro-2H-pyran-2-yl)oxy)ethyl)carbamoyl)phenyl)azanediyl)bis (ethane-2,1-diyl) dimethanesulfonate 128 (8.04 g, 96%) as a yellow gum. $^1$HNMR [$(CD_3)_2SO$] δ 8.73 (t, J=5.5 Hz, 1H), 8.15-8.10 (m, 2H), 7.27 (d, J=9.2 Hz, 1H), 4.32 (t, J=5.3 Hz, 4H), 3.82-3.74 (m, 6H), 3.56-3.40 (m, 5H), 3.13 (s, 6H), 1.76-1.71 (m, 1H), 1.68-1.61 (m, 1H), 1.50-1.47 (m, 4H).

((2-((2-hydroxyethyl)carbamoyl)-4-nitrophenyl) azanediyl)bis(ethane-2,1-diyl) dimethanesulfonate (129)

((4-Nitro-2-((2-((tetrahydro-2H-pyran-2-yl)oxy)ethyl) carbamoyl)phenyl)azanediyl)bis(ethane-2,1-diyl) dimethanesulfonate 128 (3.03 g, 5.47 mmol) in dry MeOH (100 mL) was treated with methanesulfonic acid (17.8 mL, 20.37 mmol). The reaction mixture was stirred at room temperature for 20 min and the solvent was evaporated. The residue was dissolved in EtOAc, washed with water (3×), dried with $Na_2SO_4$ and concentrated under reduced pressure and the crude product was purified by flash column chromatography on silica gel eluting with $CH_2Cl_2$/MeOH (19:1) to give ((2-((2-hydroxyethyl)carbamoyl)-4-nitrophenyl)azanediyl) bis(ethane-2,1-diyl) dimethanesulfonate 129 (1.92 g, 75%) as a yellow gum. $^1$HNMR [$(CD_3)_2SO$] δ 8.73 (t, J=5.5 Hz, 1H), 8.15-8.10 (m, 2H), 7.27 (d, J=9.2 Hz, 1H), 4.32 (t, J=5.3 Hz, 4H), 3.82-3.74 (m, 6H), 3.56-3.40 (m, 5H), 3.13 (s, 6H), 1.76-1.71 (m, 1H), 1.68-1.61 (m, 1H), 1.50-1.47 (m, 4H). HRMS(ESI) calcd for $C_{15}H_{23}N_3NaO_{10}S_2$[M+Na]$^+$ m/z 492.0717. found 492.0720.

2-((2-bromoethyl)(2-((2-hydroxyethyl)carbamoyl)-4-nitrophenyl)amino)ethyl methanesulfonate (64)

((2-((2-Hydroxyethyl)carbamoyl)-4-nitrophenyl) azanediyl)bis(ethane-2,1-diyl) dimethanesulfonate 129 (8.00 g, 17.04 mmol) was dissolved in acetone (240 mL) and treated with LiBr (1.48 g, 17.04 mmol) at the room temperature. The reaction mixture was stirred overnight and the solvent was removed. The residue was dissolved in EtOAc and washed with water (2×), dried with $Na_2SO_4$ and concentrated under reduced pressure. The crude product was purified by flash column chromatography on silica gel eluting with $CH_2Cl_2$/MeOH (20:1) to give 2-((2-bromoethyl)(2-((2-hydroxyethyl)carbamoyl)-4-nitrophenyl) amino)ethyl methanesulfonate 64 (3.74 g, 48%) as a yellow gum. $^1$HNMR [$(CD_3)_2SO$] δ 8.65 (t, J=5.6 Hz, 1H), 8.14-8.09 (m, 2H), 7.22 (d, J=9.1 Hz, 1H), 4.75 (br, 1H), 4.31 (t, J=5.4 Hz, 2H), 3.80-3.74 (m, 5H), 3.65-3.53 (m, 5H), 3.13 (s, 3H). HRMS(ESI) calcd for $C_{14}H_{21}BrN_3O_7S$ [M+H]$^+$ m/z 454.0278. found 454.0273.

2-((2-bromoethyl)(4-nitro-2-((2-(phosphonooxy)ethyl)carbamoyl)phenyl)amino)ethyl methanesulfonate (60)

2-((2-bromoethyl)(2-((2-((di-tert-butoxyphosphoryl)oxy)ethyl)carbamoyl)-4-nitrophenyl)amino)ethyl methanesulfonate (130)

A stirred solution of 2-((2-bromoethyl)(2-((2-hydroxyethyl)carbamoyl)-4-nitrophenyl)amino)ethyl methanesulfonate 64 (2.61 g, 5.76 mmol) in DMF (2 mL) at 10° C. was treated with 1H-tetrazole (61.9 mL, 26.50 mmol; 3% w/w solution in MeCN), followed by the slow addition of di-tert-butyl diisopropylphosphoramidate (95%, 7.68 mL, 23.05 mmol). The mixture was stirred at room temperature for 4 h, then cooled to 5° C. and treated with portionwise addition of m-CPBA (70%, 7.46 g, 43.21 mmol). After further stirring at room temperature for 2 h the reaction mixture was concentrated under reduce pressure and the residue was dissolved in EtOAc, washed with 10% aqueous $Na_2S_2O_5$, 5% aqueous $NaHCO_3$ and water before being dried with $Na_2SO_4$ and concentrated under reduced pressure. The crude product was purified by flash column chromatography on silica gel eluting with EtOAc/Hexane (1:1) to give 2-((2-bromoethyl)(2-((2-((di-tert-butoxyphosphoryl)oxy)ethyl)carbamoyl)-4-nitrophenyl)amino)ethyl methanesulfonate 130 (1.45 g, 39%) as a yellow gum. $^1$HNMR [(CD$_3$)$_2$SO] δ 8.84 (t, J=5.6 Hz, 1H), 8.13 (2d, J=2.8 Hz, 1H), 8.09 (d, J=2.8 Hz, 1H), 7.23 (d, J=9.3 Hz, 1H), 4.32 (t, J=5.4 Hz, 2H), 4.00 (q, J=6.3 Hz, 2H), 3.80-3.74 (m, 4H), 3.64 (t, J=6.7 Hz, 2H), 3.51 (q, J=5.6 Hz, 2H), 3.14 (s, 3H), 1.42 (s, 18H). HRMS (ESI) calcd for $C_{22}H_{37}BrKN_3O_{10}PS$ [M+K]$^+$ m/z 684.0752. found 684.0740.

2-((2-bromoethyl)(4-nitro-2-((2-(phosphonooxy)ethyl)carbamoyl)phenyl)amino)ethyl methanesulfonate (60)

A stirred solution of 2-((2-bromoethyl)(2-((2-((di-tert-butoxyphosphoryl)oxy)ethyl)carbamoyl)-4-nitrophenyl)amino)ethyl methanesulfonate 130 (1.45 g, 2.24 mmol) in $CH_2Cl_2$ (30 mL) was treated with TFA (10 mL) at room temperature with stirring for 1 h, then concentrated under reduced pressure to remove the excess TFA. The resulted yellow residue was dissolved in EtOAc and evaporated to dryness to give 2-((2-bromoethyl)(4-nitro-2-((2-(phosphonooxy)ethyl)carbamoyl)phenyl)amino)ethyl methanesulfonate 60 (1.20 g, 100%) as a yellow gum. $^1$HNMR [(CD$_3$)$_2$SO] δ 8.86 (t, J=5.6 Hz, 1H), 8.15-8.11 (m, 2H), 7.24 (d, J=9 Hz, 1H), 4.32 (t, J=5.4 Hz, 2H), 4.07-4.02 (m, 2H), 3.79-3.74 (m, 4H), 3.65 (t, J=6.7 Hz, 2H), 3.51 (q, J=5.5 Hz, 2H), 3.13 (s, 3H). HRMS (ESI) calcd for $C_{14}H_{21}BrKN_3O_{10}PS$ [M+K]$^+$ m/z 571.9500. found 571.9451.

Example 2

Prodrug Cytotoxicity Screening

Compounds were subjected to testing, including low-cell density cytotoxicity assay. Cells (500 cells/well) were seeded in 96-well plates and exposed to prodrug for 4 h, washed, then left to grow for a further 5 days. The SRB assay was employed to determine IC50 values (concentration of prodrug required to inhibit proliferation by 50%). Parental HCT116 cells and cells expressing the example nitroreductase gene nfsA from *Escherichia coli* were evaluated head-to-head. Parental H1299 cells and cells expressing the example nitroreductase gene nfsA from *Escherichia coli* were evaluated head-to-head. Parental HCT116 cells and cells expressing human AKR1C3 were evaluated head-to-head. Parental H1299 cells and cells expressing human AKR1C3 were evaluated head-to-head. In a variation of these assays test compounds were assessed for their ability to give hypoxia-selective cell killing. Here wild type HCT116, H460, H1299 and SiHa cells were used in addition to HCT116 cells engineered to over express cytochrome P450 reductase (HCT116 POR), a human one-electron nitroreductase. Low-cell density cytotoxicity assays were performed as above under oxic conditions and compared to experiments where cells were shown 4 h of anoxia during the prodrug exposure period, before being washed free of prodrug and then left to grow for a further 5 days under oxic conditions, as above.

In parallel, a three dimensional high-cell density multicellular layer (MCL) clonogenic assay was performed. 1×10$^6$ cells of either 100% HCT-116$^{WT}$ or containing 97% WT with a minor 3% HCT-116$^{NTR}$ cell population were seeded into a collagen-coated Teflon microporous membrane and left to grow for 3 days. MCLs were then exposed to prodrug for 5 h. After treatment, MCLs were enzyme dissociated, diluted in fresh medium and plated to determine clonogenic survival. To discriminate clonogenic activator (NTR+) from target (NTR−) colonies, cells were plated in non-selective medium (total cells) and medium containing 1 µM puromycin (activator cells). Colonies were grown for 10 days before staining. Colonies containing >50 cells were counted. A variation of this assay was also used to assess for evidence of AKR1C3-dependent cytotoxicity. Here either 100% HCT-116$^{WT}$ or 100% HCT-116$^{AKR1C3}$ cells were seeded to provide MCLs that were then exposed to prodrug.

Results of the screening assays are provided in FIGS. 18, 18.1, 19, 20, 20.1, 21 and 23 and show that the compounds of the present invention appear to be resistant to metabolism by AKR1C3 as indicated by an inability to provide increased cytotoxicity in low cell density cytotoxicity testing in HCT116 and H1299 cells engineered to over express AKR1C3 when compared to the cytotoxicity of the test compounds in the parental wild type cell lines (FIGS. 18 and 18.1, respectively). As the inventors have determined that 'false negatives' can occur in this assay due to metabolite diffusion into essentially infinite dilution of the assay media, the lack of AKR1C3-mediated cytotoxicity was confirmed for all of the compounds of the present invention by comparing clonogenic cell kill of wild type HCT116 cells and AKR1C3 over expressing HCT116 cells grown as multicellular layers (MCLs) and exposed to test compounds. Here all test compounds were shown to give no additional cell kill in MCLs that over express AKR1C3 compared to the wild type isogenic cell line, indicating they are not metabolised to cytotoxic metabolites by AKR1C3 (FIG. 19).

The compounds of the present invention were shown to provide excellent bacterial nitroreductase mediated cell killing in low cell density cytotoxicity assays, when assayed in HCT116 and H1299 cells engineered to over express the example nitroreductase gene nfsA from *Escherichia coli*, compared to the parental wild type cell lines (FIGS. 20 and 20.1, respectively). Here an additional 2 to 3 logs of cell kill is observed in cells that express *E coli* nfsA. To confirm the test compounds provide bystander cell killing, they were assessed in a three dimension high cell density assay employing mixed HCT116 MCLs that contain 97% wild-type HCT116 cells (target cells) and 3% HCT116 cells over expressing *E coli* nfsA (activator cells). All compounds demonstrated the ability to be metabolized by the 3%

Figure 21:
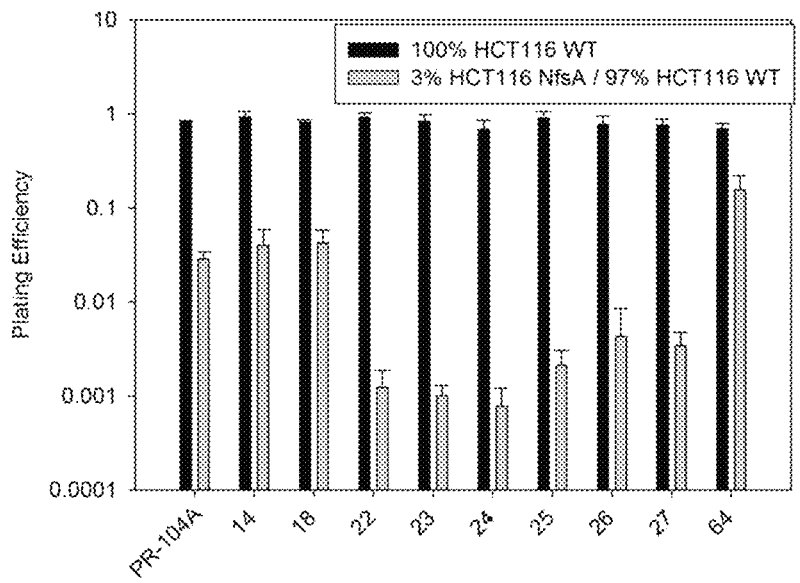
FIG. 21 shows clonogenic cell kill of PR-104A compared to prodrugs 14, 18, 22, 23, 24, 25, 26, 27, 64 of the present invention in HCT116 wild type Multicellular Layers (MCLs) versus HCT116 MCLs seeded with 3% of the cells engineered to over-express the bacterial two-electron reductase E coli NfsA to assess bystander cell killing. All of the prodrugs 14, 18, 22, 23, 24, 25, 26, 27 and 64 display evidence of metabolism by the 3% E coli NfsA-expressing cells with bystander cell killing of the 97% non-expressing neighbour cells.

HCT116 cells over expressing *E coli* nfsA to produce cytotoxic metabolites capable of diffusing to kill the neighbouring wild type HCT116 cells (FIG. 21).

The compounds of the present invention were tested in low cell density cytotoxicity assays under oxic and anoxic conditions, for their ability to give hypoxia-dependent cytotoxicity. Wild type HCT116, H460, H1299 and SiHa cells were used in addition to HCT116 cells engineered to over express cytochrome P450 reductase (HCT116 POR), a human one-electron nitroreductase. Compounds 14, 22, 18 and 301 were shown to provide increased cytotoxicity in cells under hypoxia. The degree of this effect was increased for compounds 14 and 22 when HCT116 cells over express cytochrome P450 reductase, indicating increased hypoxia-selective prodrug metabolism by this human nitroreductase is providing increased cytotoxicity (FIG. 23).

Example 3

Screening of Prodrug Compounds Using Nitroreductase Library

A phylogenetically diverse library of 55 nitroreductase candidates from 20 bacterial species, representing 12 different enzyme families was screened for their ability to co-metabolise target prodrugs.

The method employed the over-expression of a candidate nitroreductase gene from plasmid pUCX in an SOS reporter strain, as first described in Prosser et al., 2010, *Biochem Pharmacol* 79, 678-687. In order to enhance the sensitivity of the SOS reporter system, an sfiA::GFP reporter construct was integrated into a CDF-based plasmid (which contains a compatible origin of replication with pUCX) to give the pANODuet reporter plasmid for GFP screening. In addition, nfsA, nfsB, azoR, and nemA genes were deleted to minimise background metabolism, and the tolC gene deleted to minimise efflux of test compounds; this strain was designated SOS-R3. Further improvements were obtained by deleting the mdaB, ycaK, and yieF genes to minimise background metabolism, and by introducing transcriptional terminators to the pANODUET reporter plasmid. This final reporter strain was designated SOS-R4.

Example 4

In Vivo Assessment of Prodrug Efficacy
Animal Husbandry

Specific pathogen-free female homozygous nude NIH-III (NIH-Lyst$^{bg}$ Foxn1$^{nu}$ Btk$^{xid}$) mice were bred by the Vernon Jansen Unit (shared vivarium, University of Auckland). Animals were housed in Techniplast microisolator cages and provided with a standard twelve hour day-night light schedule. Animals received standard rodent diet (Harlan Teklad diet 2018i) and water adlibitum. All animal studies were approved by the University of Auckland Animal Ethics Committee.
Tumour Cell Inoculation Animals weighed 18-25 g at the time of tumour inoculation. Tumours were grown subcutaneously on the right flank of mice by inoculating cells grown in tissue culture ($1\times10^7$ cells in 100 uL serum free α-MEM). Tumour sizes were monitored three times weekly using electronic callipers and treatments were initiated once tumour diameter reached ≥7 mm.
Growth Delay Tumour bearing mice were randomised into the appropriate treatment groups and tumour size and body weight recorded. Test compounds were formulated on the day of the experiment and kept in foil-wrapped tubes out of direct fluorescent light. If recruitment of animals occurred over multiple days, the drug stocks were aliquoted into tubes and frozen once at −4° C. until required. Mice were treated with a single (or BID) dose of prodrug by intraperitoneal injection and thereafter tumour size and body weight was monitored every second day. Tumour volume was calculated as π (l×w×w)/6, where l is the major axis and w is the perpendicular minor axis. Animals were culled when they had reached the appropriate survival endpoint or when body weight loss exceeded 20% of the pre-treatment value.
Excision Assay with and without Radiation Tumours were grown subcutaneously in the flank of NIH-III mice by inoculating cells grown in tissue culture. Tumours were monitored using electronic calipers. When tumours reached treatment size, mice were randomized to treatment groups (five to seven per group). Compounds were given as single (or BID) intraperitoneal doses alone or 5 min after whole body irradiation ($^{60}$Co source). Eighteen hours after treatment, tumours were excised, weighed, minced, dissociated enzymatically, and plated to determine clonogenicity. Clonogens/gram of tissue were calculated relative to controls and effects of treatment were tested for significance (ANOVA with Dunnett's).

Figure 22:
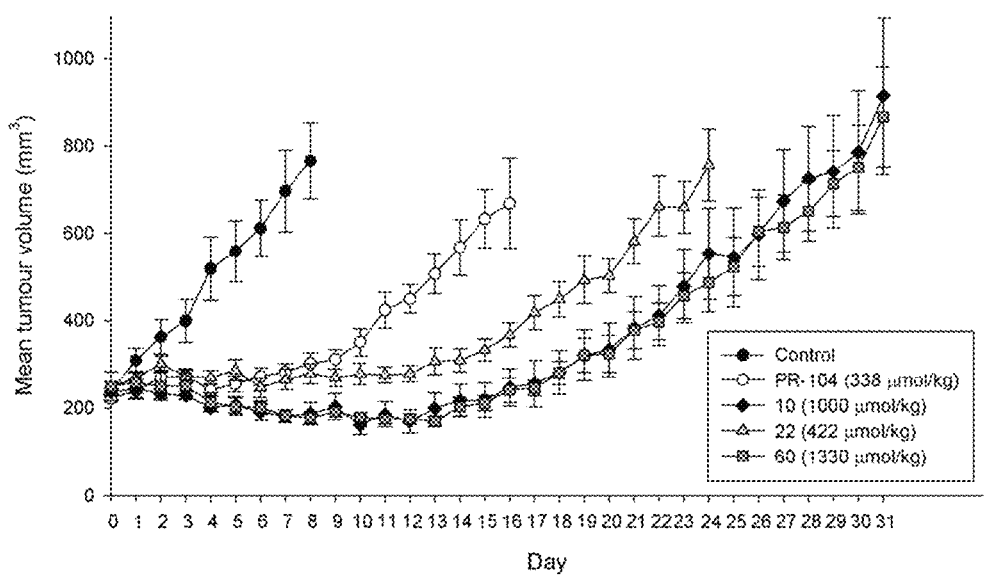
FIG. 22 shows mean tumour volume (mm3) of 15% E coli NfsA-expressing HCT116 xenografts (containing 85% wild type cells) in NIH-III mice administered a single dose of the prodrugs 10, 22 and 60 at doses of 1000, 422 and 1330 umol/kg, respectively. All of the prodrugs display significant E coli NfsA mediated anti-tumour efficacy. Mean tumour volume of PR-104 at the human equivalent dose of 338 umol/kg is shown by way of reference.

Results of the in vivo efficacy testing of prodrugs 10, 11, 22, 23, 26 and 60 of the present invention in mixed HCT116 and H1299 tumour xenografts grown to contain 15% *E coli* NfsA expressing cells and 85% wild type cells in female NIH-III mice are shown in FIGS. 22, 22.1, 22.2, 22.3, 22.4 and 22.5. All compounds tested provide a profound tumour growth delay following a single (or BID) intraperitioneal dose, indicating prodrug metabolism by *E coli* NfsA followed by metabolite diffusion to provide bystander cell killing in vivo.

Results of the in vivo efficacy testing of prodrugs 11, 22, 23 and 300 in HCT116 POR and wild type SiHa tumour xenografts are shown in FIGS. 24, 25 and 26. Here test compounds were assessed as single agents or in combination with 10 or 15Gy of radiation, following a single (or BID) intraperitoneal dose. All of the prodrugs investigated demonstrated increased cell killing above what could be achieved with radiation alone, indicating the ability of the compounds to kill hypoxic (and therefore radiation resistant) cells in the tumour xenograft.
Materials and Methods
Nitroreductase Gene Library The full list of candidate genes in the 55-membered candidate nitroreductase library is as follows (ordered alphabetically by the bacterial strain (underlined) that each was amplified from): *Bacillus coagulans* (36D1) nfsA; *Bacillus subtilis* (ATCC 6051) nfrA, ycnD, ydgI, yfkO, ywrO; *Bacillus thuringiensis* (serovar konkukian, strain 97-27) nfsA; *Citrobacterkoseri* (ATCC 27156) nfsA, nfsB; *Enterobacter* (Chronobacter) *sakazakii* (ATCC 29544) nfsA, nfsB; *Erwinia carotovora* (subspecies *Atrosepticum* SCRI1043) nfsA; *Escherichia coli* (W3110) azoR, kefF, mdaB, nemA, nfsA, nfsB, wrbA, ycdI, ydjA, yieF; *Klebsiella pneumoniae* (ATCC 13883) nemA, nfsA, nfsB, ycdI, ydjA; *Lactobacillus sakei* (subspecies *sakei* 23K) nfsA; *Listeria welshimeri* (serovar 6b, strain SLCC5334) nfsA; *Listeria innocua* (Clip11262) nfsA, ywrO; *Mycobacterium smegmatis* (strain MC$^2$155) nfsA; *Nostoc punctiforme* (PCC 73102) nfsA; *Pseudomonas aeruginosa* (PAO1) nfsB (PA5190), nqol (PA4975), yieF (PA1204); *Pseudomonas putida* (KT2440) azoR (PP4538), nfsA (PP2490), nfsB (PP2432), nqol (PP3720); *Pseudomonas syringae* pv. *phaseolicola* (1448a)

mdaB, wrbA; *Salmonella typhi* (ATCC I9430) azoR, nemA, nfsA, nfsB; *Vibrio fischeri* (ATCC 7744) FRaseI (flavin reductase 1), nfsA, ywrO; *Vibrio harveyi* (ATCC 33843) frp (flavin reductase P), nfsB; *Vibrio harveyi* (HY01) CO-frp (*E. coli* codon optimized variant of flavin reductase P); *Vibrio vulnificus* (ATCC 27562) azoR, nfsA, nfsB, nemA. To distinguish genes or enzymes with the same family name, for the purpose of this work each oxidoreductase was referred to using standard nomenclature followed by an underscore and a two letter abbreviation of the genus and species, e.g. NfsA_Kp and NemA_Ec for the NfsA enzyme from *K. pneumoniae* and NemA enzyme from *E. coli*, respectively.

In addition to screening the 55-membered candidate nitroreductase library, activity with compounds 14, 18, 22, 23, 24, 25, 26, 27 and 64 was demonstrated for a range of single and poly mutated variants of *E. coli* NfsA (NfsA_Ec), and a single-mutated variant of *B. subtilis* NfrA (NfrA_Bs/ NfsA_Bs) that had previously been engineered for enhanced activity with PR-104A. The single-mutated variants of NfsA_Ec were NfsA_Ec_12S (native arginine at position 12 substituted by serine); NfsA_Ec_41Y (native serine at position 41 substituted by tyrosine); NfsA_Ec_134A (native asparagine at position 134 substituted by alanine); and NfsA_Ec_222E (native lysine at position 222 substituted by glutamate). The single-mutated variant of NfsA_Bs was NfsA_Bs_234P (native arginine at position 234 substituted by proline). The poly-mutated variants of *E. coli* NfsA were poly17 (I5T, S41Y, R225P, F227S), poly22 (S41Y, E99G, L103M, R225P, F227S) and poly42 (S41Y, L103M, R225G, F227S).

GFP-SOS Assays

Stored glycerols of the 55-membered nitroreductase library in SOS-R4 were thawed and used to inoculate overnight cultures (Lysogeny Broth (LB) amended with 100 µg ml$^{-1}$ Ampicillin, 50 µg ml$^{-1}$ Spectinomycin, 0.4% glucose) that were incubated at 30° C., 200 rpm for 16 h. The next morning the GFP-SOS assay was commenced by inoculation of 195 µl fresh assay media (LB+100 µg ml$^{-1}$ Ampicillin, 50 µg ml$^{-1}$ Spectinomycin, 0.2% glucose, 50 µM IPTG) with 15 µl of overnight culture in individual wells of a 96-well plate. Plates were incubated at 30° C., 200 rpm for 2.5 h (pre-challenge period), following which cultures were diluted 1:2 by splitting 50:50 into fresh assay media (+DMSO to 0.5% final concentration) and fresh challenge media (assay media+drug to desired concentration, DMSO to 0.5% final concentration) to final volumes of 80 µl apiece in duplicate on a 384-well plate. Plates were incubated at 30° C., 200 rpm for 6 h (challenge period). GFP expression was determined at excitation 488 nm/emission 509 nm. Turbidity was determined by $OD_{600}$ and fluorescence data from any replicates not found to be within 15% of the median culture turbidity were discarded.

Purified Enzyme Kinetics

For compounds 14, 18, 22, 23, 24, 25, 26, 27 and 64 steady-state enzyme kinetics with purified NfsA_Ec were assessed spectrophotometrically at 400 nm to directly monitor compound reduction, as described for PR-104A in Prosser et al. (2013). Molar extinction coefficients of 4800 $M^{-1}$ cm$^{-1}$ (compounds 14 and 18), 5200 $M^{-1}$ cm$^{-1}$ (compound 22), 5500 $M^{-1}$ cm$^{-1}$ (compounds 25 and 26), 5600 $M^{-1}$ cm$^{-1}$ (compounds 23, 24 and 27) and 10,000 $M^{-1}$ cm$^{-1}$ (compound 64) were measured (as described for PR-104A in Prosser et al., 2013, *Biochem Pharmacol* 85, 1091-1103) and used for the calculation of enzyme activity. Reactions were performed in 60 µl in UVettes (Eppendorf), using the 2 mm light path length. Reactions contained 10 mM Tris-CI (pH 7.0), 4% DMSO, 0.25 mM NADPH and varying compound concentrations. Reactions were initiated by addition of 6 µl enzyme and changes in absorbance were measured for 20 s (during linearity). For calculation of $K_m$ and $k_{cat}$, substrate concentrations were varied from ~$0.2 \times K_m$ up to either $5 \times K_m$ or the maximum concentration permitted by compound solubility. Non-linear regression analysis and Michaelis-Menten curve fitting was performed using Sigmaplot 10.0 (Systat Software Inc.).

NfsB Rate Assay

The solubility limits of the compounds meant that apparent $K_m$ and $k_{cat}$ parameters could not be accurately determined for NfsB_Ec, which exhibited a linear rate of reduction for all compounds within the achievable concentration ranges. Instead, assessment of the relative rate of compound reduction by NfsB_Ec at one fixed concentration (600 µM) of each compound was performed. Individual reactions were established in an identical manner to that described for determination of purified enzyme kinetics for NfsA_Ec.

Results

Results of the NTR screening of the prodrugs in bacteria and the NfsA kinetics and NfsB rate of metabolism assays are provided in FIGS. 17.1 to 17.11. Compounds 14, 18, 22, 23, 24, 25, 26, 27 and 64 were all confirmed to be substrates for multiple wild type and mutant bacterial nitroreductases from the NfsA and NfsB families from several species of bacteria, as assessed by their ability to be metabolised by the bacterial nitroreductase to genotoxic metabolites that result in an SOS response in bacteria (FIGS. 17.1 to 17.9). Metabolism of the test compounds by *E coli* NfsA was confirmed by incubating varying concentrations of the compounds in the presence of recombinant *E coli* NfsA and NADPH co-factor and then following the loss of co-factor over time. Enzyme $K_m$'s were confirmed to range from 160 to 820 uM. Enzyme $k_{cat}$ ranged from 3.6 to 21.9 s$^{-1}$ (FIG. 17.10). Metabolism of the test compounds by *E coli* NfsB was confirmed by incubating one fixed concentration (600 µM) of each compound in the presence of recombinant *E coli* NfsB and NADPH co-factor and then following the loss of co-factor over time. All compounds tested were metabolised by *E coli* NfsB with rates varying from 200 to 4500 umol/min/mg (FIG. 17.11).

Throughout this specification, unless the context requires otherwise, the words "comprise", "comprising" and the like, are construed in an inclusive sense as opposed to an exclusive sense, that is to say, in the sense of "including, but not limited to".

The reference to any prior art in this specification is not, and should not be taken as, an acknowledgement or any form of suggestion that that prior art forms part of the common general knowledge.

It will be appreciated that the compounds of the invention may occur in different geometric and enantiomeric forms, and that both pure forms and mixtures of these compounds are included.

The entire disclosures of all applications, patents and publications cited above and below, if any, are herein incorporated by reference.

The invention may be said broadly to consist in the parts, elements and features referred to or indicated in the specification, individually or collectively, in any or all combinations of two or more of said parts, elements or features.

Wherein the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

The invention claimed is:

1. A method for treating cancer or a hyperproliferative condition, the method comprising administering a compound of formula (I), or a pharmaceutically acceptable salt thereof, in a therapeutically effective amount to a tumor cell, or therapeutically proximate to said tumor cell, in a solid and/or hypoxic tumor in a subject:

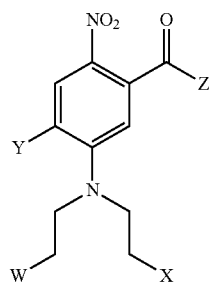
(I)

wherein
W represents Cl, Br, I, OSO$_2$R,
X represents Cl, Br, I, OSO$_2$R,
Y represents H, CN, SO$_2$R,
each R independently represents a lower C$_{1-6}$ alkyl group,
Z is selected from any of the radicals

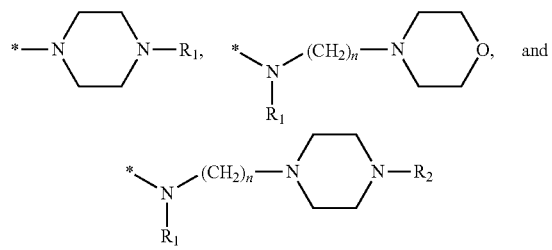

wherein
R$_1$ represents H, or a lower C$_{1-6}$ alkyl group;
R$_2$ represents H, or a lower C$_{1-6}$ alkyl group;
n represents 2 to 6;
* represents a point of attachment to formula (I).

2. The method according to claim 1, wherein the compound of formula (I) is represented by the formula (Ih)

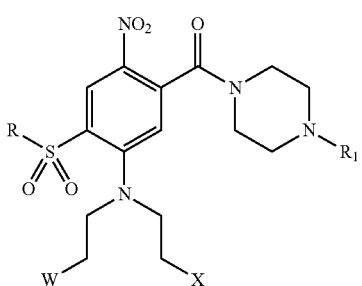
(Ih)

wherein
W represents Cl, Br, I, OSO$_2$R,
X represents Cl, Br, I, OSO$_2$R,
R independently represents a lower C$_{1-6}$ alkyl group, and
R$_1$ represents H, or a lower C$_{1-6}$ alkyl group.

3. The method according to claim 2, wherein the compound of formula (Ih) is represented by the following formula,

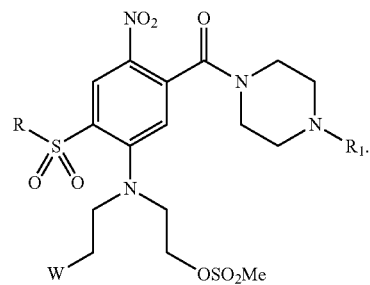

4. The method according to claim 1, wherein the compound of formula (I) is represented by formula (Ib)

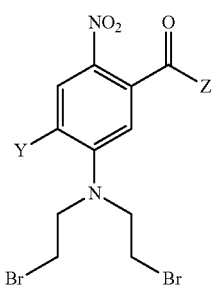
(Ib)

wherein
Y represents H, CN, SO$_2$R,
R represents a methyl or ethyl group,
Z is selected from any of the radicals

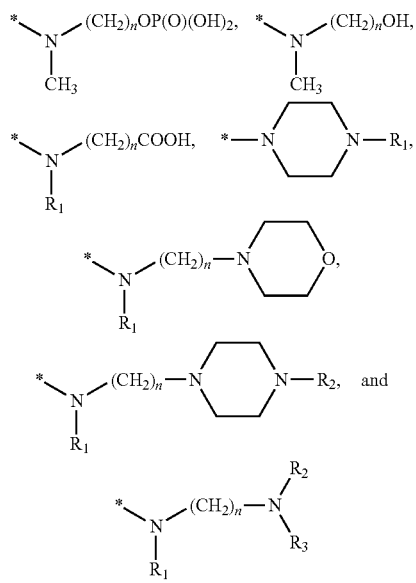

wherein
R$_1$ represents a lower C$_{1-6}$ alkyl group;
R$_2$ and R$_3$ may independently represent H, or a lower C$_{1-6}$ alkyl group;

n represents 2 to 6;

* represents a point of attachment to formula (Ib);

or a pharmaceutically acceptable salt of said compound.

5. The method according to claim 1, wherein the tumour cells express nitroreductase.

6. The method according to claim 1, further including the steps of
   a) irradiating the tumor cells; or
   b) administering one or more chemotherapeutic agents and/or therapies to the subject;

before, during or after the administration of the compounds of formula (I).

7. The method according to claim 1, wherein the compound is administered to a subject in conjunction with gene-directed enzyme prodrug therapy, virus-directed enzyme prodrug therapy, clostridia-directed enzyme prodrug therapy or antibody-directed enzyme prodrug therapy.

8. The method according to claim 1, wherein the compound is administered to a subject in combination with
   a) at least one nitroreductase enzyme capable of metabolising the compound; or
   b) a therapy that results in expression of an exogenous nitroreductase enzyme within, or therapeutically proximate to, a tumour.

9. The method according to claim 3, wherein the compound is selected from the group consisting of:
   2-((2-bromoethyl)(5-(4-methylpiperazine-1-carbonyl)-2-(methylsulfonyl)-4-nitrophenyl)amino)ethyl methanesulfonate (compound 310),
   2-((2-bromoethyl)(5-(4-ethylpiperazine-1-carbonyl)-2-(methylsulfonyl)-4-nitrophenyl)amino)ethyl methanesulfonate (compound 311),
   2-((2-bromoethyl)(5-(4-isopropylpiperazine-1-carbonyl)-2-(methylsulfonyl)-4-nitrophenyl)amino)ethyl methanesulfonate (compound 312),
   2-((2-bromoethyl)(2-ethylsulfonyl)-5-(4-methylpiperazine-1-carbonyl)-4-nitrophenyl)amino)ethyl methanesulfonate (compound 313),
   2-((2-bromoethyl)(5-(4-ethylpiperazine-1-carbonyl)-2-(ethylsulfonyl)-4-nitrophenyl)amino)ethyl methanesulfonate (compound 314), and
   2-((2-bromoethyl)(2-ethylsulfonyl)-5-(4-isopropylpiperazine-1-carbonyl)-4-nitrophenyl)amino)ethyl methanesulfonate (compound 315).

10. The method according to claim 1, wherein the compound is selected from the group consisting of:
    2-((2-bromoethyl)(2-(methylsulfonyl)-5-((2-morpholinoethyl)carbamoyl)-4-nitrophenyl)amino)ethyl methanesulfonate (compound 316),
    2-((2-bromoethyl)(5-(methyl(2-morpholinoethyl)carbamoyl)-2-(methylsulfonyl)-4-nitrophenyl)amino)ethyl methanesulfonate (compound 317),
    2-((2-bromoethyl)(2-(methylsulfonyl)-5-((3-morpholinopropyl)carbamoyl)-4-nitrophenyl)amino)ethyl methanesulfonate (compound 318),
    2-((2-bromoethyl)(5-(methyl(3-morpholinopropyl)carbamoyl)-2-(methylsulfonyl)-4-nitrophenyl)amino)ethyl methanesulfonate (compound 319),
    2-((2-bromoethyl)(5-((2-(4-methylpiperazin-1-yl)ethyl)carbamoyl)-2-(methylsulfonyl)-4-nitrophenyl)amino)ethyl methanesulfonate (compound 320),
    2-((2-bromoethyl)(5-(methyl(2-(4-methylpiperazin-1-yl)ethyl)carbamoyl)-2-(methylsulfonyl)-4-nitrophenyl)amino)ethyl methanesulfonate (compound 321),
    2-((2-bromoethyl)(5-((3-(4-methylpiperazin-1-yl)propyl)carbamoyl)-2-(methylsulfonyl)-4-nitrophenyl)amino)ethyl methanesulfonate (compound 322),
    2-((2-bromoethyl)(5-(methyl(3-(4-methylpiperazin-1-yl)propyl)carbamoyl)-2-(methylsulfonyl)-4-nitrophenyl)amino)ethyl methanesulfonate (compound 323),
    2-((2-bromoethyl)(2-(ethylsulfonyl)5-((2-morpholinoethyl)carbamoyl)-4-nitrophenyl)amino)ethyl methanesulfonate (compound 328),
    2-((2-bromoethyl)(2-(ethylsulfonyl)-5-(methyl(2-morpholinoethyl)carbamoyl)-4-nitrophenyl)amino)ethyl methanesulfonate (compound 329),
    2-((2-bromoethyl)(2-(ethylsulfonyl)-5-((3-morpholinopropyl)carbamoyl)-4-nitrophenyl)amino)ethyl methanesulfonate (compound 330),
    2-((2-bromoethyl)(2-(ethylsulfonyl)-5-(methyl(3-morpholinopropyl)carbamoyl)-4-nitrophenyl)amino)ethyl methanesulfonate (compound 331),
    2-((2-bromoethyl)(2-(ethylsulfonyl)-5-((2-(4-methylpiperazin-1-yl)ethyl)carbamoyl)-4-nitrophenyl)amino)ethyl methanesulfonate (compound 332),
    2-((2-bromoethyl)(2-(ethylsulfonyl)-5-(methyl(2-(4-methylpiperazin-1-yl)ethyl)carbamoyl)-4-nitrophenyl)amino)ethyl methanesulfonate (compound 333),
    2-((2-bromoethyl)(2-(ethylsulfonyl)-5-((3-(4-methylpiperazin-1-yl)propyl)carbamoyl)-4-nitrophenyl)amino)ethyl methanesulfonate (compound 334),
    2-((2-bromoethyl)(2-(ethylsulfonyl)-5-(methyl(3-(4-methylpiperazin-1-yl)propyl)carbamoyl)-4-nitrophenyl)amino)ethyl methanesulfonate (compound 335),
    2-((2-bromoethyl)(2-cyano-5-(4-methylpiperazine-1-carbonyl)-4-nitrophenyl)amino)ethyl methanesulfonate (compound 352),
    2-((2-bromoethyl)(2-cyano-5-(4-ethylpiperazine-1-carbonyl)-4-nitrophenyl)amino)ethyl methanesulfonate (compound 353),
    2-((2-bromoethyl)(2-cyano-5-(4-isopropylpiperazine-1-carbonyl)-4-nitrophenyl)amino)ethyl methanesulfonate (compound 354),
    2-((2-bromoethyl)(2-cyano-5-((2-morpholinoethyl)carbamoyl)-4-nitrophenyl)amino)ethyl methanesulfonate (compound 359),
    2-((2-bromoethyl)(2-cyano-5-(methyl(2-morpholinoethyl)carbamoyl)-4-nitrophenyl)amino)ethyl methanesulfonate (compound 360),
    2-((2-bromoethyl)(2-cyano-5-((3-morpholinopropyl)carbamoyl)-4-nitrophenyl)amino)ethyl methanesulfonate (compound 361),
    2-((2-bromoethyl)(2-cyano-5-(methyl(3-morpholinopropyl)carbamoyl)-4-nitrophenyl)amino)ethyl methanesulfonate (compound 362),
    2-((2-bromoethyl)(2-cyano-5-((2-(4-methylpiperazin-1-yl)ethyl)carbamoyl)-4-nitrophenyl)amino)ethyl methanesulfonate (compound 363),
    2-((2-bromoethyl)(2-cyano-5-(methyl(2-(4-methylpiperazin-1-yl)ethyl)carbamoyl)-4-nitrophenyl)amino)ethyl methanesulfonate (compound 364),
    2-((2-bromoethyl)(2-cyano-5-((3-(4-methylpiperazin-1-yl)propyl)carbamoyl)-4-nitrophenyl)amino)ethyl methanesulfonate (compound 365), and
    2-((2-bromoethyl)(2-cyano-5-(methyl(3-(4-methylpiperazin-1-yl)propyl)carbamoyl)-4-nitrophenyl)amino)ethyl methanesulfonate (compound 366).

11. The method according to claim 1, wherein the compound is represented by formula (Ii):

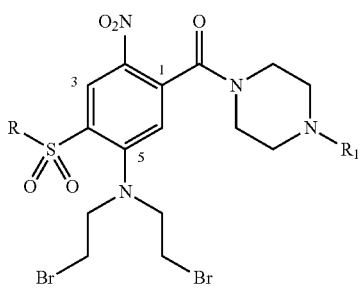

(Ii)

wherein

R represents a lower $C_{1-6}$ alkyl group, $R_1$ represents H, or a lower $C_{1-6}$ alkyl group, or a pharmaceutically acceptable salt of said compound.

12. The method according to claim 11, being a pharmaceutically acceptable salt of said compound, wherein said salt is a methanesulfonate salt.

13. The method according to claim 11, wherein the compound is selected from the group consisting of:
- (5-(bis(2-bromoethyl)amino)-4-(methylsulfonyl)-2-nitrophenyl)(4-methylpiperazin-1-yl)methanone (compound 22),
- (5-(bis(2-bromoethyl)amino)-4-(methylsulfonyl)-2-nitrophenyl)(4-ethylpiperazin-1-yl)methanone (compound 23),
- (5-(bis(2-bromoethyl)amino)-4-(methylsulfonyl)-2-nitrophenyl)(4-isopropylpiperazin-1-yl)methanone (compound 24),
- (5-(bis(2-bromoethyl)amino)-4-(ethylsulfonyl)-2-nitrophenyl)(4-methylpiperazin-1-yl)methanone (compound 25),
- (5-(bis(2-bromoethyl)amino)-4-(ethylsulfonyl)-2-nitrophenyl)(4-ethylpiperazin-1-yl)methanone (compound 26), and
- (5-(bis(2-bromoethyl)amino)-4-(ethylsulfonyl)-2-nitrophenyl)(4-isopropylpiperazin-1-yl)methanone (compound 27).

14. The method according to claim 11, wherein the compound is selected from the group consisting of:
- 5-(bis(2-bromoethyl)amino)-4-(methylsulfonyl)-N-(2-morphohnoethyl)-2-nitrobenzamide (compound 28),
- 5-(bis(2-bromoethyl)amino)-N-methyl-4-(methylsulfonyl)-N-(2-morpholinoethyl)-2-nitrobenzamide (compound 29),
- 5-(bis(2-bromoethyl)amino)-4-(methylsulfonyl)-N-(3-morpholinopropyl)-2-nitrobenzamide (compound 30),
- 5-(bis(2-bromoethyl)amino)-N-methyl-4-(methylsulfonyl)-N-(3-morpholinopropyl)-2-nitrobenzamide (compound 31),
- 5-(bis(2-bromoethyl)amino)-N-(2-(4-methylpiperazin-1-yl)ethyl)-4-(methylsulfonyl)-2-nitrobenzamide (compound 32),
- 5-(bis(2-bromoethyl)amino)-N-methyl-N-(2-(4-methylpiperazin-1-yl)ethyl)-4-(methylsulfonyl)-2-nitrobenzamide (compound 33),
- 5-(bis(2-bromoethyl)amino)-N-(3-(4-methylpiperazin-1-yl)propyl)-4-(methylsulfonyl)-2-nitrobenzamide (compound 34),
- 5-(bis(2-bromoethyl)amino)-N-methyl-N-(3-(4-methylpiperazin-1-yl)propyl)-4-(methylsulfonyl)-2-nitrobenzamide (compound 35),
- 5-(bis(2-bromoethyl)amino)-4-(ethylsulfonyl)-N-(2-morpholinoethyl)-2-nitrobenzamide (compound 40),
- 5-(bis(2-bromoethyl)amino)-4-(ethylsulfonyl)-N-methyl-N-(2-morpholinoethyl)-2-nitrobenzamide (compound 41),
- 5-(bis(2-bromoethyl)amino)-4-(ethylsulfonyl)-N-(3-morpholinopropyl)-2-nitrobenzamide (compound 42),
- 5-(bis(2-bromoethyl)amino)-4-(ethylsulfonyl)-N-methyl-N-(3-morpholinopropyl)-2-nitrobenzamide (compound 43),
- 5-(bis(2-bromoethyl)amino)-4-(ethylsulfonyl)-N-(2-(4-methylpiperazin-1-yl)ethyl)-2-nitrobenzamide (compound 44),
- 5-(bis(2-bromoethyl)amino)-4-(ethylsulfonyl)-N-methyl-N-(2-(4-methylpiperazin-1-yl)ethyl)-2-nitrobenzamide (compound 45),
- 5-(bis(2-bromoethyl)amino)-4-(ethylsulfonyl)-N-(3-(4-methylpiperazin-1-yl)propyl)-2-nitrobenzamide (compound 46),
- 5-(bis(2-bromoethyl)amino)-4-(ethylsulfonyl)-N-methyl-N-(3-(4-methylpiperazin-1-yl)propyl)-2-nitrobenzamide (compound 47),
- 2-(bis(2-bromoethyl)amino)-4-(4-methylpiperazine-1-carbonyl)-5-nitrobenzonitrile (compound 71),
- 2-(bis(2-bromoethyl)amino)-4-(4-ethylpiperazine-1-carbonyl)-5-nitrobenzonitrile (compound 72),
- 2-(bis(2-bromoethyl)amino)-4-(4-isopropylpiperazine-1-carbonyl)-5-nitrobenzonitrile (compound 73),
- 5-(bis(2-bromoethyl)amino)-4-cyano-N-(2-morpholinoethyl)-2-nitrobenzamide (compound 78),
- 5-(bis(2-bromoethyl)amino)-4-cyano-N-methyl-N-(2-morpholinoethyl)-2-nitrobenzamide (compound 79),
- 5-(bis(2-bromoethyl)amino)-4-cyano-N-(3-morpholinopropyl)-2-nitrobenzamide (compound 80),
- 5-(bis(2-bromoethyl)amino)-4-cyano-N-methyl-N-(3-morpholinopropyl)-2-nitrobenzamide (compound 81),
- 5-(bis(2-bromoethyl)amino)-4-cyano-N-(2-(4-methylpiperazin-1-yl)ethyl)-2-nitrobenzamide (compound 82),
- 5-(bis(2-bromoethyl)amino)-4-cyano-N-methyl-N-(2-(4-methylpiperazin-1-yl)ethyl)-2-nitrobenzamide (compound 83),
- 5-(bis(2-bromoethyl)amino)-4-cyano-N-(3-(4-methylpiperazin-1-yl)propyl)-2-nitrobenzamide (compound 84), and
- 5-(bis(2-bromoethyl)amino)-4-cyano-N-methyl-N-(3-(4-methylpiperazin-1-yl)propyl)-2-nitrobenzamide (compound 85).

15. A method according to claim 8, wherein the nitroreductase enzyme
a) is encoded for by the nfsB and/or the nfsA gene of either *E. coli* or by the orthologous genes in other bacterial species; or
b) comprises a mutant nitroreductase.

16. The method according to claim 1, wherein said therapeutically effective amount of a compound of formula (I) is about 20% to 100% of the maximum tolerated dose of said subject.

17. A method according to claim 1, wherein said therapeutically effective amount of a compound of formula (I) is comprised in a pharmaceutical composition further comprising at least one of a pharmaceutically acceptable excipient, adjuvant, carrier, buffer or stabiliser.

18. The method according to claim 1, wherein said composition is formulated for parenteral administration.

19. The method according to claim 1, wherein said composition is formulated in unit dosage form.

20. The method according to claim 1, wherein the method further comprises dissolving the compound of formula (I) in an aqueous solution.

21. The method according to claim 1, wherein the compound of formula (I) is the methanesulfonate salt of the compound.

22. The method according to claim 7, wherein the clostridia-directed enzyme produg therapy comprises use of a *Clostridia* microorganism that is selective for colonising the necrosis found in tumours.

23. The method according to claim 22, wherein the *Clostridia* microorganism is a recombinant microorganism comprising one or more genes expressing a nitroreductase exogenous to the *Clostridia* microorganism.

* * * * *